US 10,456,036 B2

(12) United States Patent
Wong et al.

(10) Patent No.: US 10,456,036 B2
(45) Date of Patent: Oct. 29, 2019

(54) STRUCTURED TAILORING

(75) Inventors: Daniel Wong, Sunnyvale, CA (US);
David Hasker, San Jose, CA (US);
Glenn Brassington, Sunnyvale, CA (US); Stefan Weinert, Pendleton, IN (US); Abhishek S. Soni, Indianapolis, IN (US); Alan Greenburg, Indianapolis, IN (US); Paul J. Galley, Cumberland, IN (US); Ulrich Porsch, Weinheim (DE); Robert E. Reinke, Indianapolis, IN (US); Marco De Polo, San Mateo, CA (US)

(73) Assignee: Roche Diabetes Care, Inc., Indianapolis, IN (US)

(*) Notice: Subject to any disclaimer, the term of this patent is extended or adjusted under 35 U.S.C. 154(b) by 631 days.

(21) Appl. No.: 12/818,930

(22) Filed: Jun. 18, 2010

(65) Prior Publication Data

US 2011/0145747 A1 Jun. 16, 2011

Related U.S. Application Data

(63) Continuation-in-part of application No. 12/643,415, filed on Dec. 21, 2009.
(Continued)

(51) Int. Cl.
*A61B 5/00* (2006.01)
*A61B 5/145* (2006.01)
(Continued)

(52) U.S. Cl.
CPC ........ *A61B 5/0002* (2013.01); *A61B 5/14532* (2013.01); *A61B 5/4833* (2013.01);
(Continued)

(58) Field of Classification Search
USPC .......................................................... 705/2–4
See application file for complete search history.

(56) References Cited

U.S. PATENT DOCUMENTS

| 4,151,845 A | 5/1979 | Clemens |
| 4,731,726 A | 3/1988 | Allen, III |
| (Continued) | | |

FOREIGN PATENT DOCUMENTS

| CN | 1130006 A | 8/1996 |
| DE | 102005041627 A1 | 3/2007 |
| (Continued) | | |

OTHER PUBLICATIONS

Coulston, Ann M., et al., "Nutrition in the Prevention and Treatment of Disease", Elsevier Science, Published Apr. 11, 2008, Edition No. 2, pp. 3-37.*

(Continued)

*Primary Examiner* — Amber A Misiaszek
(74) *Attorney, Agent, or Firm* — Dinsmore & Shohl, LLP

(57) ABSTRACT

Embodiments related to a self-administered, behavior modification program facilitated through a structured tailoring method and system thereof which accelerates and enhances the internalization process of the individual, and which provides help when the individual begins to fail in adhering or continuing with the behavior modification are disclosed. Program instructions that when executed by a processor causes a processor to initiate automatically a schedule of events of a structured tailoring procedure upon entry criteria being met at some unknown time, provide intervention according to the intervention preferences when the adherence criteria for one of the events has not been met, and end automatically the structured collection procedure upon exit criteria being met at some unknown time.

30 Claims, 23 Drawing Sheets

Related U.S. Application Data

(60) Provisional application No. 61/140,270, filed on Dec. 23, 2008.

(51) Int. Cl.
| | | |
|---|---|---|
| *G06F 19/00* | (2018.01) | |
| *G06Q 10/10* | (2012.01) | |
| *G06Q 50/22* | (2018.01) | |
| *G16H 10/20* | (2018.01) | |
| *G16H 40/63* | (2018.01) | |
| *G16H 50/20* | (2018.01) | |
| *A61B 5/021* | (2006.01) | |
| *A61B 5/024* | (2006.01) | |

(52) U.S. Cl.
CPC ........ *A61B 5/7264* (2013.01); *G06F 19/3418* (2013.01); *G06Q 10/10* (2013.01); *G06Q 50/22* (2013.01); *G16H 10/20* (2018.01); *G16H 40/63* (2018.01); *G16H 50/20* (2018.01); *A61B 5/021* (2013.01); *A61B 5/024* (2013.01); *A61B 5/14546* (2013.01); *A61B 5/7275* (2013.01); *A61B 2562/0219* (2013.01)

(56) References Cited

U.S. PATENT DOCUMENTS

| | | | |
|---|---|---|---|
| 4,803,625 A | 2/1989 | Fu et al. | |
| 5,364,346 A | 11/1994 | Schrezenmeir | |
| 5,377,258 A | 12/1994 | Bro | |
| 5,572,421 A | 11/1996 | Altman et al. | |
| 5,576,952 A | 11/1996 | Stutman et al. | |
| 5,665,065 A | 9/1997 | Colman et al. | |
| 5,722,418 A * | 3/1998 | Bro | 600/545 |
| 5,822,715 A | 10/1998 | Worthington et al. | |
| 5,840,020 A | 11/1998 | Heinonen et al. | |
| 5,868,669 A | 2/1999 | Iliff | |
| 5,879,163 A | 3/1999 | Brown et al. | |
| 5,897,493 A | 4/1999 | Brown | |
| 5,971,922 A | 10/1999 | Arita et al. | |
| 6,018,713 A | 1/2000 | Coli et al. | |
| 6,024,699 A | 2/2000 | Surwit | |
| 6,039,688 A | 3/2000 | Douglas et al. | |
| 6,108,665 A * | 8/2000 | Bair et al. | |
| 6,234,964 B1 | 5/2001 | Iliff | |
| 6,241,633 B1 | 6/2001 | Conroy | |
| 6,269,314 B1 | 7/2001 | Itawaki et al. | |
| 6,326,160 B1 | 12/2001 | Dunn et al. | |
| 6,338,039 B1 * | 1/2002 | Lonski et al. | 705/3 |
| 6,352,505 B1 | 3/2002 | Bortz | |
| 6,379,301 B1 | 4/2002 | Worthington et al. | |
| 6,424,847 B1 | 7/2002 | Mastrototaro et al. | |
| 6,425,863 B1 | 7/2002 | Werner et al. | |
| 6,544,212 B2 | 4/2003 | Galley et al. | |
| 6,567,785 B2 | 5/2003 | Clendenon | |
| 6,575,900 B1 | 6/2003 | Zweig et al. | |
| 6,645,368 B1 | 11/2003 | Beaty et al. | |
| 6,656,114 B1 | 12/2003 | Poulsen et al. | |
| 6,691,043 B2 | 2/2004 | Ribeiro, Jr. | |
| 6,770,029 B2 | 8/2004 | Iliff | |
| 6,835,175 B1 | 12/2004 | Porumbescu | |
| 6,879,970 B2 | 4/2005 | Shiffman et al. | |
| 6,923,763 B1 | 8/2005 | Kovatchev et al. | |
| 6,954,662 B2 | 10/2005 | Freger et al. | |
| 7,179,226 B2 | 2/2007 | Crothall et al. | |
| 7,229,430 B2 | 6/2007 | Hickle et al. | |
| 7,241,265 B2 | 7/2007 | Cummings et al. | |
| 7,266,400 B2 | 9/2007 | Fine et al. | |
| 7,278,983 B2 | 10/2007 | Ireland et al. | |
| 7,381,523 B2 | 6/2008 | Efendic | |
| 7,389,133 B1 | 6/2008 | Kotulla et al. | |
| 7,404,796 B2 | 7/2008 | Ginsberg | |
| 7,405,196 B2 | 7/2008 | Rosskamp et al. | |
| 7,413,749 B2 | 8/2008 | Wright et al. | |
| 7,415,447 B2 | 8/2008 | Shiffman et al. | |
| 7,509,156 B2 | 3/2009 | Flanders | |
| 7,523,040 B2 | 4/2009 | Kirchhoff et al. | |
| 7,553,281 B2 | 6/2009 | Hellwig et al. | |
| 7,676,329 B2 | 3/2010 | Garczarek et al. | |
| 7,685,000 B1 | 3/2010 | Petit et al. | |
| 7,734,323 B2 | 6/2010 | Blomquist et al. | |
| 7,761,310 B2 | 7/2010 | Rodgers | |
| 7,766,830 B2 | 8/2010 | Fox et al. | |
| 8,078,592 B2 | 12/2011 | Gejdos et al. | |
| 8,117,020 B2 | 2/2012 | Abensour et al. | |
| 8,606,761 B2 * | 12/2013 | Kenedy et al. | 707/688 |
| 2002/0107476 A1 | 8/2002 | Mann et al. | |
| 2002/0143563 A1 | 10/2002 | Hufford et al. | |
| 2002/0161288 A1 | 10/2002 | Shin et al. | |
| 2003/0028399 A1 | 2/2003 | Davis et al. | |
| 2003/0104982 A1 | 6/2003 | Wittmann et al. | |
| 2003/0130616 A1 | 7/2003 | Steil et al. | |
| 2003/0208113 A1 | 11/2003 | Mault et al. | |
| 2003/0211617 A1 | 11/2003 | Jones | |
| 2004/0078065 A1 | 4/2004 | Kroll | |
| 2004/0122701 A1 * | 6/2004 | Dahlin et al. | 705/2 |
| 2004/0122709 A1 | 6/2004 | Avinash et al. | |
| 2004/0247748 A1 | 12/2004 | Bronkema | |
| 2005/0010416 A1 | 1/2005 | Anderson et al. | |
| 2005/0016844 A1 | 1/2005 | Burke et al. | |
| 2005/0020903 A1 | 1/2005 | Krishnan et al. | |
| 2005/0021372 A1 | 1/2005 | Mikkelsen et al. | |
| 2005/0049179 A1 | 3/2005 | Davidson et al. | |
| 2005/0119540 A1 | 6/2005 | Potts et al. | |
| 2005/0119788 A1 | 6/2005 | Engleson et al. | |
| 2006/0010014 A1 | 1/2006 | Brown | |
| 2006/0010098 A1 | 1/2006 | Goodnow et al. | |
| 2006/0025931 A1 | 2/2006 | Rosen et al. | |
| 2006/0030890 A1 | 2/2006 | Cosentino et al. | |
| 2006/0031094 A1 | 2/2006 | Cohen et al. | |
| 2006/0171503 A1 | 8/2006 | O'Hara et al. | |
| 2006/0173406 A1 | 8/2006 | Hayes et al. | |
| 2006/0195022 A1 | 8/2006 | Trepagnier et al. | |
| 2006/0195029 A1 | 8/2006 | Shults et al. | |
| 2006/0195342 A1 | 8/2006 | Khan et al. | |
| 2006/0253296 A1 | 11/2006 | Liisberg et al. | |
| 2006/0271404 A1 | 11/2006 | Brown | |
| 2006/0287883 A1 | 12/2006 | Turgiss et al. | |
| 2007/0048691 A1 | 3/2007 | Brown | |
| 2007/0055483 A1 | 3/2007 | Lee et al. | |
| 2007/0100659 A1 | 5/2007 | Preiss | |
| 2007/0106135 A1 | 5/2007 | Sloan et al. | |
| 2007/0162304 A1 | 7/2007 | Rodgers | |
| 2007/0198296 A1 | 8/2007 | Pellinat et al. | |
| 2007/0213604 A1 | 9/2007 | Brown | |
| 2007/0253904 A1 | 11/2007 | Gunton et al. | |
| 2007/0282636 A1 | 12/2007 | Sauk et al. | |
| 2008/0025591 A1 | 1/2008 | Bhanot et al. | |
| 2008/0109043 A1 | 5/2008 | Salo et al. | |
| 2008/0125636 A1 | 5/2008 | Ward et al. | |
| 2008/0146895 A1 | 6/2008 | Olson et al. | |
| 2008/0154513 A1 | 6/2008 | Kovatchev et al. | |
| 2008/0172027 A1 | 7/2008 | Blomquist | |
| 2008/0177119 A1 | 7/2008 | Juttu et al. | |
| 2008/0177149 A1 | 7/2008 | Weinert et al. | |
| 2008/0177165 A1 | 7/2008 | Blomquist et al. | |
| 2008/0183494 A1 | 7/2008 | Cuddihy et al. | |
| 2008/0201325 A1 | 8/2008 | Doniger et al. | |
| 2008/0206799 A1 | 8/2008 | Blomquist | |
| 2008/0214919 A1 | 9/2008 | Harmon et al. | |
| 2008/0228056 A1 | 9/2008 | Blomquist et al. | |
| 2008/0234943 A1 | 9/2008 | Ray et al. | |
| 2008/0234992 A1 | 9/2008 | Ray et al. | |
| 2008/0243902 A1 | 10/2008 | Rong et al. | |
| 2008/0255438 A1 | 10/2008 | Saidara et al. | |
| 2008/0262745 A1 | 10/2008 | Polidori | |
| 2008/0269585 A1 | 10/2008 | Ginsberg | |
| 2008/0306353 A1 | 12/2008 | Douglas et al. | |
| 2008/0319384 A1 | 12/2008 | Yodfat et al. | |
| 2009/0006061 A1 | 1/2009 | Thukral et al. | |
| 2009/0018406 A1 | 1/2009 | Yodfat et al. | |
| 2009/0150177 A1 | 6/2009 | Buck et al. | |
| 2009/0150186 A1 | 6/2009 | Cohen et al. | |
| 2009/0164239 A1 | 6/2009 | Hayter et al. | |

(56) References Cited

U.S. PATENT DOCUMENTS

| | | |
|---|---|---|
| 2009/0176692 A1 | 7/2009 | Habermann et al. |
| 2009/0177147 A1 | 7/2009 | Blomquist et al. |
| 2009/0234262 A1 | 9/2009 | Reid et al. |
| 2009/0247836 A1 | 10/2009 | Cole et al. |
| 2009/0253970 A1 | 10/2009 | Bashan et al. |
| 2009/0253973 A1 | 10/2009 | Bashan et al. |
| 2009/0281393 A1 | 11/2009 | Smith |
| 2010/0016700 A1 | 1/2010 | Sieh et al. |
| 2010/0138197 A1 | 6/2010 | Sher |
| 2010/0141656 A1 | 6/2010 | Krieftewirth |
| 2010/0160757 A1 | 6/2010 | Weinert et al. |
| 2010/0174553 A1 | 7/2010 | Kaufman et al. |
| 2010/0184565 A1 | 7/2010 | Avellino |
| 2010/0198142 A1 | 8/2010 | Sloan et al. |
| 2010/0198520 A1 | 8/2010 | Breton et al. |
| 2010/0222765 A1 | 9/2010 | Blomquist et al. |
| 2010/0262434 A1 | 10/2010 | Shaya |
| 2010/0265073 A1 | 10/2010 | Harper |
| 2010/0274497 A1 | 10/2010 | Rush |
| 2010/0330598 A1 | 12/2010 | Thukral et al. |
| 2010/0331650 A1 | 12/2010 | Batman et al. |
| 2010/0331651 A1 | 12/2010 | Groll |
| 2011/0071365 A1 | 3/2011 | Lee et al. |
| 2011/0145747 A1 | 6/2011 | Wong et al. |
| 2012/0226117 A1 | 9/2012 | Lamego et al. |

FOREIGN PATENT DOCUMENTS

| | | |
|---|---|---|
| EP | 1702559 A2 | 9/2006 |
| EP | 1728469 A2 | 12/2006 |
| EP | 1956508 A2 | 8/2008 |
| EP | 2006786 A1 | 12/2008 |
| FR | 2760962 A1 | 3/1997 |
| WO | 94/20916 A1 | 9/1994 |
| WO | 9901836 | 1/1999 |
| WO | 0009007 | 2/2000 |
| WO | 0122343 A2 | 3/2001 |
| WO | 0133314 A2 | 5/2001 |
| WO | 01/52727 A1 | 7/2001 |
| WO | 2003/002258 A1 | 1/2003 |
| WO | 2003/046695 A2 | 6/2003 |
| WO | 2003/082096 A1 | 10/2003 |
| WO | 2004/015539 A2 | 2/2004 |
| WO | 2004/084820 A2 | 10/2004 |
| WO | 2007/081853 A2 | 7/2007 |
| WO | 2007117719 A2 | 10/2007 |
| WO | 2007/149319 A2 | 12/2007 |
| WO | 2007144419 A2 | 12/2007 |
| WO | 2008/091320 A2 | 7/2008 |
| WO | 2008/105859 A1 | 9/2008 |
| WO | 2008/131324 A1 | 10/2008 |
| WO | 2009/009528 A2 | 1/2009 |
| WO | 2009/013637 A2 | 1/2009 |
| WO | 2009/075925 A1 | 6/2009 |
| WO | 2009/146119 A2 | 12/2009 |
| WO | 2010/000266 A1 | 1/2010 |
| WO | 2010/039743 A1 | 4/2010 |
| WO | 2010/075350 A1 | 7/2010 |
| WO | 2010072387 A2 | 7/2010 |
| WO | 2010/089304 A1 | 8/2010 |
| WO | 2010/089305 A1 | 8/2010 |
| WO | 2010/089306 A1 | 8/2010 |
| WO | 2010/089307 A1 | 8/2010 |
| WO | 2010/097796 A1 | 9/2010 |

OTHER PUBLICATIONS

Calvo, Katherine R., et al., "Clinical Proteomics: From Biomarker Discovery and Cell Signaling Profiles to Individualized Personal Therapy", Bioscience Reports, vol. 25, Nos. 1-2, February/April.*
Murff, et al., "Detecting adverse events for patient safety research: a review of current methodologies", Journal of Biomedical Informatics, 36 (2003) pp. 131-143. (Year: 2003).*
Non Final Office Action pertaining to U.S. Appl. No. 12/818,875, dated Apr. 2, 2012.
Non-final Office Action pertaining to U.S. Appl. No. 12/643,338 dated Apr. 26, 2012.
Montani et al., "Integrating Case Based and Rule Based Reasoning in a Decision Support System: Evalation with Simulated Patients", AMIA, Inc., pp. 887-891, 1999.
Montani et al., "Managing diabetic patients through a Multi Modal Reasoning methodology", International Journal of Medical Informatics, vol. 58, Complete, pp. 243-256, Sep. 1, 2000.
Schmidt et al., "Case-based Reasoning for Medical Knowledge-based Systems", Institute for Medical Informatics and Biometry, University of Rostock Rembrandstr. 16/17, D-18055 Rostock, Germany, 2000.
Denis Raccah, "Insulin therapy in patients with type 2 diabetes mellitus: Treatment to target fasting and postprandial blood glucose levels", Insulin 1:158-165, 2006.
Morgan et al., "Uncertainty A Guide to Dealing with Uncertainty in Quantitative Risk and Poly Analysis", Cambridge University Press, pp. 307-310, 1990.
Brand et al., "Updating uncertainty in an integrated risk assessment: Conceptual framework and methods", Risk Analysis 1995 US, vol. 15, No. 6, pp. 719-731, 1995.
Huang Elbert S., "The key to preventing burnout: understanding the burden of diabetes treatment", DiabetesVoice, vol. 53, Issue 3, pp. 33-35, Dec. 2008.
Larimer, et al., "Relapse Prevention, an Overview of Marlatt's Cognitive-Behavioral Model", Alcohol Research & Health, vol. 23, No. 2, pp. 151-160, 1999.
Marlatt, et al., "Clinical Guidelines for Implementing Relapse Prevention Therapy", Addictive Behaviors Research Center/University of Washington, pp. 1-49, Dec. 2002.
International Search Report and Written Opinion completed Oct. 5, 2011, pertaining to International Application No. PCT/EP2011/002924.
Ingersoll, et al., "The Impact of Medication Regimen Factors on Adherence to Chronic Treatment: a Review of Literature", NIH Public Access, Author Manuscript, J Behav Med. Jun. 2008; 31(3): 213-224. doi:10.1007/s10865-007-9147-y; pp. 1-16.
Joslin Diabetes Center & Joslin Clinic, "Clinical Guideline for Pharmacological Management of Type 2 Diabetes", Jan. 12, 2007, pp. 1-9.
Joslin Diabetes Center & Joslin Clinic, "Clinical Guideline for Adults with Diabetes", May 21, 2010, pp. 1-13.
Lustria, et al., "Computer-Tailored Health Interventions Delivered Over the Web: Review and Analysis of Key Components", U.S. National Library of Medicine, National Institute of Health, 2009, p. 1.
Munro, et al., "Association Between Medication Regimen Complexity and Achievement of Therapeutic Goals in Patients with Type 2 Diabetes", School of Pharmacy, The Robert Gordon University, Aberdeen, AB10 1 FR (k.munroe@rgu.ac.uk), pp. 1, 2.
Pollack, et al., "Impact of treatment Complexity on Adherence and Glycemic Control: An Analysis of Oral Antidiabetic Agents", www.jcomjournal.com, vol. 17, No. 6, Jun. 2010, pp. 257-265.
ACCU-CHEK Spirit Pump User Guide, Sep. 2008, pp. 1-201.
ACCU-CHEK Pocket Compass Software with Bolus Calculator User Guide, Oct. 2005, pp. 1-174.
ACCU-CHEK Aviva Blood Glucose Meter Owner's Booklet, Sep. 2008, pp. 1-92.
ACCU-CHEK 360 Diabetes Management System, Aug. 24, 2010, pp. 1-2.
Accu-Chek Smart Pix Device Reader User's Manual, Sep. 2008, pp. 1-92.
De Groen, et al., "Applying World Wide Web Technology to the Study of Patients with Rare Diseases, Annals of Internal Medicine", vol. 129, No. 2, Jul. 15, 1998, pp. 107-113, XP002587966, 1998.
Dassau, et al., "Detection of a Meal Using Continuous Glucose Monitoring", Diabetes Care, vol. 31, No. 2, Feb. 2008, pp. 295-300.
Gerstein et al., "A randomized trial of adding insulin glargine vs. avoidance of insulin in people with Type 2 diabetes on either no oral glucose-lowering agents or submaximal doses of metformin and/or sulphonylureas. The Canadian INSIGHT (Implementing New Strategies with Insulin Glargine for Hyperclycaemia Treatment) Study", Diabetic Medicine, vol. 23, pp. 736-742, 2006.

(56) References Cited

OTHER PUBLICATIONS

Hirsch et al., "A Real-World Approach to Insulin Therapy in Primary Care Practice", Practical Pointers, Clinical Diabetes, vol. 23, Nov. 2, 2005.
Nathan, et al., "Medical Management of Hyperglycemia in Type 2 Diabetes: A Consensus Algorithm for the Initiation and Adjustment of Therapy", Diabetes Care, vol. 31, No. 12: pp. 1-11, Dec. 2008.
Riddle, et al., "The Treat-to-Target Trial, Randomized addition of glargine or human NPH insulin to oral therapy of type 2 diabetic patients", Diabetes Care, vol. 26, No. 11: pp. 2080-3086, Nov. 2003.
Crowe, et al., "Time Synching or Time Sinking?", Diabetes Technology & Therapeutics, vol. 7, No. 5, 2005.
International Search Report, Application No. PCT/EP2009/009170 filed Dec. 21, 2009, completion of ISR dated Sep. 24, 2010, pp. 1-24.
International Search Report, Application No. PCT/EP2009/009171 filed Dec. 21, 2009, completion of ISR dated Jun. 21, 2010, pp. 1-14.
Non-final Office Action pertaining to U.S. Appl. No. 12/818,310 dated Sep. 26, 2012.
Final Office Action pertaining to U.S. Appl. No. 12/818,875 dated Sep. 28, 2012.
Non-final Office Action pertaining to U.S. Appl. No. 12/643,415 dated Sep. 13, 2012.
Non-final Office Action pertaining to U.S. Appl. No. 12/818,930 dated Aug. 27, 2012.
International Preliminary Report on Patentability dated Nov. 13, 2012 pertaining to International Application No. PCT/EP2011/002925.
Final Office Action pertaining to U.S. Appl. No. 12/818,894 dated Nov. 21, 2012.
Final Office Action pertaining to U.S. Appl. No. 12/643,338 dated Dec. 3, 2012.
International Search Report and Written Opinion dated Nov. 24, 2011, pertaining to International Application No. PCT/EP2011/002925.
Non-final Office Action pertaining to U.S. Appl. No. 13/107,436, dated May 31, 2013.
Final Office Action pertaining to U.S. Appl. No. 12/643,415, dated May 17, 2013.
USPTO Non Final Rejection dated Dec. 18, 2013 in reference to co-pending U.S. Appl. No. 12/818,310, filed Jun. 18, 2010.
USPTO Final Rejection dated Feb. 21, 2014 in reference to co-pending U.S. Appl. No. 12/818,894, filed Jun. 18, 2010.
Office Action dated Apr. 19, 2018 pertaining to U.S. Appl. No. 14/252,052, 38 pages.

* cited by examiner

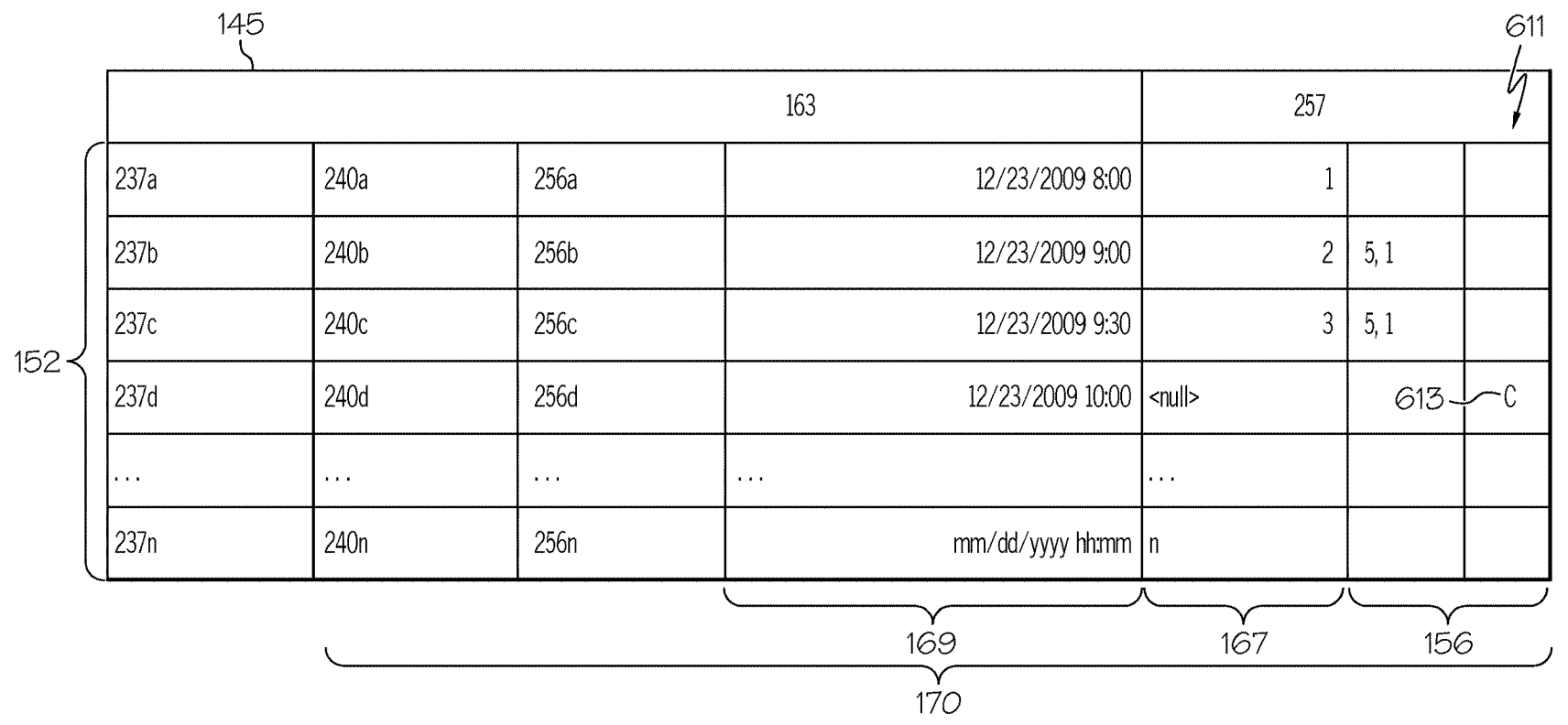

| | 237a | 240a | 256a | 163 | 257 | 611 | | |
|---|---|---|---|---|---|---|---|---|
| | 237b | 240b | 256b | 12/23/2009 8:00 | 1 | | | |
| | 237c | 240c | 256c | 12/23/2009 9:00 | 2 | 5,1 | | |
| | 237d | 240d | 256d | 12/23/2009 9:30 | 3 | 5,1 | | |
| | ... | ... | ... | 12/23/2009 10:00 | <null> | 613 — C | | |
| | 237n | 240n | 256n | mm/dd/yyyy hh:mm | n | | | |

FIG. 4

| PARAMETERS | bG (BIOSENSOR) MEASUREMENT | MEAL SIZE (S, M, OR L) | ENERGY LEVEL (1 - 5) | TIMING | ACCEPTANCE CRITERIA | GUIDANCE | OPTIONS |
|---|---|---|---|---|---|---|---|
| bG LEVEL TRENDING | | | | | | | |
| ENTRY CRITERIA | | | | MM-DD-YYYY | AFFIRMS GUIDANCE, IF NOT ADD 1 DAY TO TIMING | ARE YOU WILLING TO CONDUCT A TEST OVER 3 CONSECUTIVE DAYS? | |
| EXIT CRITERIA | | | | MM-DD-YYYY | ENTRY TIMING + 3 DAYS | | |
| BEFORE BREAKFAST | Y | | Y | HHMM | | PLEASE INDICATE ENERGY LEVEL | 1 |
| $n_1$ HOURS AFTER BREAKFAST | Y | Y | Y | $n_1$ | ± 30 MINUTES OF $n_1$ | PLEASE INDICATE MEAL SIZE & ENERGY LEVEL | |
| BEFORE LUNCH | Y | | Y | | | PLEASE INDICATE ENERGY LEVEL | |
| $n_2$ HOURS AFTER LUNCH | Y | Y | Y | $n_2$ | ± 30 MINUTES OF $n_1$ | PLEASE INDICATE MEAL SIZE & ENERGY LEVEL | |
| BEFORE DINNER | Y | | Y | | | PLEASE INDICATE ENERGY LEVEL | |
| $n_3$ HOURS AFTER DINNER | Y | Y | Y | $n_3$ | ± 30 MINUTES OF $n_1$ | PLEASE INDICATE MEAL SIZE & ENERGY LEVEL | |
| BEFORE BED | Y | | Y | | | PLEASE INDICATE ENERGY LEVEL | |

FIG. 7

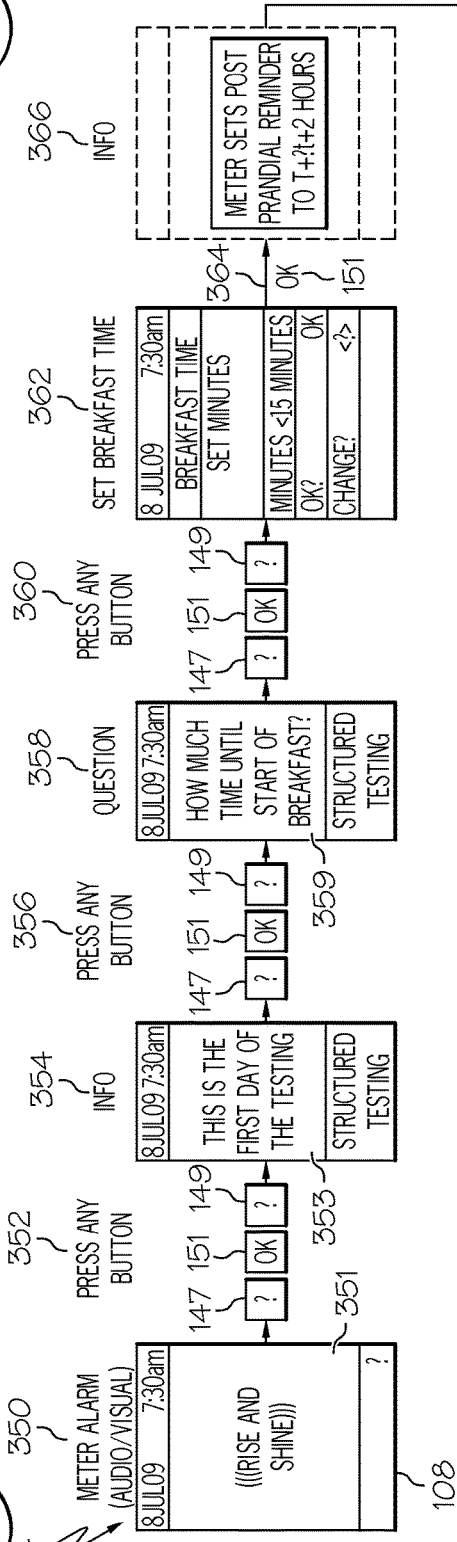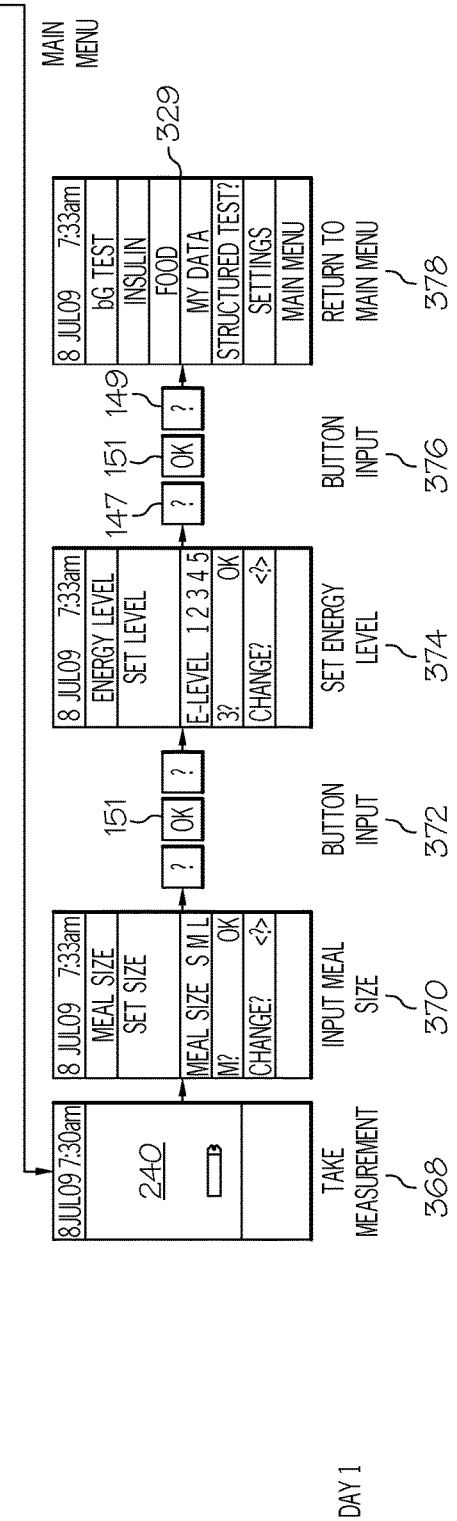
FIG. 8C

| PARAMETERS | bG (BIOSENSOR) MEASUREMENT | MEAL SIZE (S, M, OR L) | ENERGY LEVEL (1 - 5) | TIMING | ACCEPTANCE CRITERIA | GUIDANCE | OPTIONS | VIOLATION |
|---|---|---|---|---|---|---|---|---|
| bG LEVEL TRENDING | | | | | | | | VN(s), t(s) |
| ENTRY CRITERIA | | | | MM-DD-YYYY | AFFIRMS GUIDANCE, IF NOT ADD 1 DAY TO TIMING | ARE YOU WILLING TO CONDUCT A TEST OVER 3 CONSECUTIVE DAYS? | | N |
| EXIT CRITERIA | | | | MM-DD-YYYY | ENTRY TIMING + 3 DAYS | | | N |
| BEFORE BREAKFAST | Y | | Y | HH:MM | | PLEASE INDICATE ENERGY LEVEL | | |
| $n_1$ HOURS AFTER BREAKFAST | Y | Y | Y | $n_1$ | ± 30 MINUTES OF $n_1$ | PLEASE INDICATE MEAL SIZE & ENERGY LEVEL | 1 | Y |
| BEFORE LUNCH | Y | | Y | | | PLEASE INDICATE ENERGY LEVEL | | |
| $n_2$ HOURS AFTER LUNCH | Y | Y | Y | $n_2$ | ± 30 MINUTES OF $n_1$ | PLEASE INDICATE MEAL SIZE & ENERGY LEVEL | | Y |
| BEFORE DINNER | Y | | Y | | | PLEASE INDICATE ENERGY LEVEL | | |
| $n_3$ HOURS AFTER DINNER | Y | Y | Y | $n_3$ | ± 30 MINUTES OF $n_1$ | PLEASE INDICATE MEAL SIZE & ENERGY LEVEL | | N |
| BEFORE BED | Y | | Y | | | PLEASE INDICATE ENERGY LEVEL | | |
| STARTING INFORMATION | | | | | | STARTING INFO & HELP INFO | PATIENT {} HAD VIOLATION | |

"PLEASE CALL CLINICIAN"

"DO YOU UNDERSTAND THE PROCEDURE?"
"DO YOU NEED CLINICIAN TO EXPLAIN?"

FIG. 10

STRUCTURED TAILORING

CROSS-REFERENCE TO RELATED APPLICATIONS

The present application is a continuation in part of U.S. patent application Ser. No. 12/643,415 filed Dec. 21, 2009, which claims priority to U.S. Provisional Application Ser. No. 61/140,270 filed Dec. 23, 2008, both of which are incorporated by reference herein in their entirety.

TECHNICAL FIELD

Embodiments disclosed herein are directed to behavior modification methods and systems and particularly to self-administered, behavior modification facilitated through a structured tailoring method and system thereof.

BACKGROUND

Behavior modification programs are known and typically require an individual to follow a predetermined and/or clinician determined series of steps and/or milestones in order to achieve lifestyle changes necessary to maintain his or her health or recover from ailments or medical procedures. However, changing behavior is difficult. Although many behavior modification programs do an adequate job in setting up goals and suggestions for users to monitor progress, they fall short when the user begins to fail in adhering or continuing through the behavior modification. For many users, changing behavior can only be accomplished once an individual has internalized the behavior needing to be changed.

SUMMARY

It is against the above background that the embodiments of the invention provide a self-administered, behavior modification program facilitated through a structured tailoring method and system thereof which accelerates and enhances the internalization process of the individual, and which provides help when the individual begins to fail in adhering or continuing with the behavior modification.

In one embodiment, a method of performing a structured collection procedure of an individual which helps the individual change a current behavior to a target behavior is disclosed. The method comprises providing a structured collection procedure and program instructions, and executing the program instructions on a device which cause a processor of the device to: personalize the structured collection procedure by requesting goals from the individual to define for events to be accomplished in the structured collection procedure one or more adherence criteria that the processor uses to determine whether each event was accomplished successfully and to define an exit criterion for ending the structured collection procedure; request intervention preferences from the individual; initiate automatically a schedule of the events defined in the structured collection procedure upon one or more entry criteria being met at some unknown time; provide intervention according to the intervention preferences when the one or more adherence criteria for one of the events is not met; and end automatically the structured collection procedure upon the one or more exit criteria being met at some unknown time.

In another embodiment, the program instructions further cause the processor to perform an initial assessment of the individual to tailor both the events as well as the interventions provided by the structured collection procedure. In another embodiment, the initial assessment is based on answers to catalog questions provided to the individual. In another embodiment, the initial assessment cover areas of readiness for change, current health, and activity level of the individual. In another embodiment, the program instructions further cause the processor to provide a recommendation based on the input received from the individual concerning the initial assessment. In another embodiment, the program instructions further cause the processor to use the recommendation as the one or more entry criteria. In another embodiment, the program instructions further cause the processor permit the individual to tailor the recommendation to his or her individual abilities and availability. In another embodiment, the program instructions further cause the processor to permit the individual to define the goals as short term goals, midterm goals, and a long-term goal. In another embodiment, the program instructions further cause the processor to automatically cycle through each of the goals defined by the individual upon successfully completion of a previous goal. In another embodiment, the program instructions further cause the processor to provide a recommendation based on the input received from the individual concerning the initial assessment, and to define one of the goals as a short-term goal that is based on the results from the assessment and the recommendation. In another embodiment, the program instructions further cause the processor to provide upon request an education module which provides education material. In another embodiment, the education material contains health and behavior education in relation to the targeted behavior. In another embodiment, the education material include a skill assessment and skill development activities. In another embodiment, the program instructions further cause the processor to assess if the individual possesses the proper level of skill before moving into a new structured collection procedure. In another embodiment, the program instructions further cause the processor to provide skill development activities for the individual to complete in order to gain the skill for the new structured collection procedure if assess by the processor as not have the proper level of skill. In another embodiment, the program instructions further cause the processor to provide a behavior support assessment to ascertain from the individual what barriers and motivators in the past have assisted in success or failures when it comes to performing the target behavior. In another embodiment, the program instructions further cause the processor to provide a behavior-support intervention module in which the individual picks one or more pre-defined interventions based on the barriers and motivators ascertained from the individual. In another embodiment, the pre-defined interventions are selected from electronic alarms, reminders, messages, and prompting social support networks for help. In another embodiment, the program instructions further cause the processor to provide a validation module which ascertains whether an appropriate level of intervention is assigned due to an associated risk if one of the events fail to meet the one or more adherence criteria. In another embodiment, the schedule of events define how often progress will be monitored by the procedure. In another embodiment, the program instructions further cause the processor to monitor compliancy of the individual with the events by assessing whether the one or more adherence criteria have been met by the individual when performing each one of the events. In another embodiment, the program instructions further cause the processor to check whether there is an indication that the structured collection procedure is not working if the exit criteria are not met. In another embodiment, the indication is provided to the processor by the individual or is shown in collected data associated with each one of the events. In another embodiment, where the indication is present, then the program instructions further cause the processor to query the individual as to whether the individual believes the procedure is working, whether the individual is following the intervention, or whether the individual is lacking in a skill or understanding of how attain the goals. In another embodiment, wherein the program instruction further cause the processor to perform a health and behavior support assessment in order to work through the process of providing a new personalized collection procedure if the collection procedure is indicated as not working, to request again the intervention preferences from the individual if the individual indicates that the intervention is not being followed, and to provide education material or start a skill assessment module if the individual indicates a lack in skill or understanding. In another embodiment, the program instructions further cause the processor to stop the structured collection procedure if the one or more adherence criteria are not met and instructs the individual to contact a clinician.

In still another embodiment, a system for performing a structured collection procedure of an individual which helps the individual change a current behavior to a target behavior is disclosed. The system comprises memory; a processor connected to the memory; and program instructions which when executed by the processor causes the processor to: personalize the structured collection procedure by requesting goals from the individual to define for events to be accomplished in the structured collection procedure one or more adherence criteria that the processor uses to determine whether each event was accomplished successfully and to define an exit criterion for ending the structured collection procedure, and requesting intervention preferences from the individual; initiate automatically a schedule of the events defined in the structured collection procedure upon one or more entry criteria being met at some unknown time, store in the memory data collected in accordance to the schedule; provide intervention according to the intervention preferences when the one or more adherence criteria for one of the events is not met; and end automatically the structured collection procedure upon the one or more exit criteria being met at some unknown time.

In still another embodiment, a method of structured tailoring which assists an individual in addressing a health related behavior is disclosed. The method comprises providing a master protocol comprising sub-protocols of various structured collection procedures and program instructions, each of the various structured collection procedures address a goal that addresses the health related behavior and comprises entry criteria and exit criteria, wherein entry criteria of some of the various structured collection procedures is met upon exit criteria of previous ones of the various structured collection procedures being met; and executing the program instructions on a device which cause a processor of the device to: use the entry criteria of each of the various structured collection procedures to determine which of the various structured collection procedures are first enabled in the master protocol, run the master protocol with first enabled ones of the various structured collection procedures, end each of the first enabled ones of the various structured collection procedures when the exit criteria of each of the first enabled ones of the various structured collection procedures have been met, and run the master protocol with next ones of the various structured collection procedure having their entry criteria met by the exit criteria of the previous ones of the various structured collection procedures being met. It is to be appreciated that by the above method, the master protocol is dynamically designed depending on which exit criterion is met.

In another embodiment, the entry criteria of a sub-protocol comprises at least one of an exit criterion of another sub-protocol and a further entry criterion. In another embodiment, the program instructions further cause the processor to check preferences of the individual as the further entry criterion to determine which of the various structured collection procedures is first enabled in the master protocol. In another embodiment, the program instructions further cause the processor to use calculated skills of the individual as the further entry criteria for one or more of the various structured collection procedures. In another embodiment, the program instructions further cause the processor to use calculated skills of the individual as the further entry criterion for one or more of the various structured collection procedures, wherein each of the one or more of the various structured collection procedures having the entry criteria based on the calculated skill has a different skill level which must be met or exceeded in order to met the entry criteria. In another embodiment, wherein one or more of the various structured collection procedures further comprises adherence criteria, and wherein the program instructions further cause the processor to check the adherence criteria of the structured collection procedures enabled in the master protocol and change which ones of the various structured collection are enabled in the master protocol when the adherence criterion is not met. In another embodiment, the next ones of the various structured collection procedure are automatically run by the processor when their entry criteria are met by the exit criteria of the previous ones of the various structured collection procedures being met. In another embodiment, the program instructions further cause the processor to use calculated skills of the individual as the exit criteria for one or more of the various structured collection procedures. In another embodiment, the program instructions further cause the processor to use calculated skills of the individual as the exit criteria for one or more of the various structured collection procedures, wherein each of the one or more of the various structured collection procedures having the exit criteria based on the calculated skill has a different skill level which must be met or exceeded in order to met the exit criteria. In another embodiment, the exit criterion for one or more of the various structured collection procedures stops their associated structured collection procedure to avoid non-reasonable data input if at least one of an acceptance criterion and an adherence criterion is not met. In another embodiment, the adherence criterion is calculated based on the data related to the behavior of the user and the acceptance criterion is calculated based on data related to the health condition of the user. In another embodiment, at least one of the acceptance criterion and the adherence criterion is calculated based on a single data point or a number of data points. In another embodiment, the exit criterion of a not met acceptance criterion and/or adherence criterion causes the master protocol to run with next ones of the various structured collection procedure having their entry criteria met by that exit criterion and after meeting an exit criterion of that next ones of the various structured collection procedure starting a new protocol or going back to the previous protocol with the exit criterion of a not met acceptance criterion and/or adherence criterion. In another embodiment, after the exit criterion is met for one or more of the structured collection procedures, the program instructions further cause the processor to provide automatically one of a learning tool and a trouble shooting guide before starting the next ones of the structured collection procedures. In another embodiment, the program instructions further cause the processor to present recommended actions and to require active confirmation by the individual for each of the recommended actions. In another embodiment, the device further comprises a user interface in communication with the processor and the active confirmation by the individual is via the user interface. In another embodiment, after the active confirmation by the individual, the program instructions further cause the processor to present automatically one of a web page, or web page link which offers the user selective information with respect to each one of the recommended actions that was confirmed. In another embodiment, the selective information comprises addresses of restaurants located near the individual, sport activities located near the individual, group of people with similar interests located near the individual, training courses located near the individual, or combinations thereof.

In still another embodiment, a method of assisting an individual in changing a health related behavior is disclosed. The method comprises requesting on an electronic device a data input of data related to a health condition of a user; calculating a medical need based on that data; calculating a recommended health related behavior change based on the medical need which will lead to an improved health condition of the user; requesting on the electronic device a data input of data related to preferences of the individual regarding events to be accomplished in order to change the health related behavior; providing a structured collection procedure based the calculated health related behavior change, whereby the structured collection procedure is adapted based on entered ones of the preferences of the individual; and executing program instructions on the electronic device which cause a processor of the device to initiate the adapted structured collection procedure which takes the individual preferences of the user into account.

In another embodiment, the requesting on the electronic device is via providing a catalogue of questions to the individual. In another embodiment, the structured collection procedure is based on answers to the catalogue questions. In another embodiment, the adapted structured collection procedure comprises of at least one of a learning tool and a trouble shooting guide. In another embodiment, the method further comprises requesting a data input of data related to the behavior of the user in the past. In another embodiment, the method further comprises comparing the data related to the behavior of the user in the past with the data related to the preferences of the individual and calculating based on that comparison the willingness of the individual to do events not indicated as a preference by the individual. In another embodiment, a willingness of the individual is calculated by applying pattern recognition of the data related to the behavior of the user in the past, wherein the pattern recognition can be any suitable conventional pattern recognition software. In another embodiment, the method further comprises requesting intervention preferences from the individual. In another embodiment, the method further comprises assessing whether an appropriate level of intervention has been entered by the individual based on associated risk of non-adherence to the structured collection procedure. In another embodiment, if the appropriate level of intervention has not been entered by the individual, the method further comprises presenting for selection appropriate levels of intervention for the associated risk of non-adherence to the structured collection procedure. In another embodiment, if the appropriate level of intervention has not been entered by the individual, the method further comprises having the device select automatically the appropriate level of intervention for the associated risk of non-adherence to the structured collection procedure.

In still another embodiment, a method of assisting an individual in changing a health related behavior is disclosed. The method comprises providing on an electronic device a skill calculation module which calculates the skills of an individual based on a data input of data related to the behavior of the user a structured collection procedure which addresses the health related behavior and comprises an entry criterion having a skill level; receiving on an electronic device a data input of data from the individual related to the behavior of the individual calculating the skill of the individual based on the received input; and permitting the individual access to the structured collection procedure on the electronic device if the entry criterion is met by the calculated skill of the individual meeting or exceeding the skill level.

In another embodiment, the method further comprises the device providing training based on the calculated skill of the individual. In another embodiment, the structured collection procedure further comprises exit criteria having a skill level, and said method further comprises having the device end the structured collection procedure if calculated skill of the individual after the training meets the exit criteria by the calculated skill of the individual meeting or exceeding the skill level of the exit criteria. In another embodiment, the method further comprises the device automatically initiating another structured collection procedure having a higher skill level upon meeting the exit criteria. In another embodiment, the received input is pair testing data, and the calculated skill is based on comparing an estimation values with measured values provided in the pair testing data. In another embodiment, the device calculates the skill level of the individual based on input selected from adherence to structured collection procedure after initiation, adherence of one or more previous initiated structured collection procedures, status of a disease of the individual, a classification of the health related behavior, a self-reported skill level, and combinations thereof.

In still yet another embodiment, a method for performing a structured collection procedure of an individual which helps the individual change a current behavior to a target behavior is disclosed. The method comprises a master protocol comprising sub-protocols of various structured collection procedures and program instructions, each of the various structured collection procedures address a goal that addresses the target behavior and comprises entry criteria and exit criteria, wherein entry criteria of some of the various structured collection procedures is met upon exit criteria of previous ones of the various structured collection procedures being met; and executing the program instructions on a device which cause a processor of the device to: personalize the structured collection procedure by requesting goals from the individual to define for entry criteria to be accomplished in the structured collection procedure, one or more adherence criteria that the processor uses to determine whether each event was accomplished successfully and to define an exit criterion for ending the structured collection procedure, and requesting intervention preferences from the individual; use the entry criteria based on invention preferences from the individual of each of the various structured collection procedures to determine which of the various structured collection procedures are first enabled in the master protocol, run the master protocol with first enabled ones of the various structured collection procedures, end each of the first enabled ones of the various structured collection procedures when the exit criteria of each of the first enabled ones of the various structured collection procedures have been met, and run the master protocol with next ones of the various structured collection procedure having their entry criteria met by the exit criteria of the previous ones of the various structured collection procedures being met.

These and other advantages and features of the various embodiments of the invention disclosed herein, will be made more apparent from the description, drawings and claims that follow.

BRIEF DESCRIPTION OF THE DRAWINGS

The following detailed description of the embodiments of the present invention can be best understood when read in conjunction with the following drawings, where like structure is indicated with like reference numerals.

FIG. 4 shows a depiction in tabular format of a data record embodiment created from using a structured tailoring method on the collection device of FIG. 3 according to the present invention.

FIG. 7 conceptually illustrates one example of a pre-defined structured collection procedure, and a method for customizing the pre-defined structured collection procedure according to an embodiment of the present invention.

FIGS. 8B and 8C show a method of implementing a structured collection procedure via a graphical user interface provided on a collection device according to an embodiment of the present invention.

FIG. 10 conceptually illustrates another example of a pre-defined structured collection procedure, and a method for customizing the pre-defined structured collection procedure according to an embodiment of the present invention.

DETAILED DESCRIPTION

Figure 1:
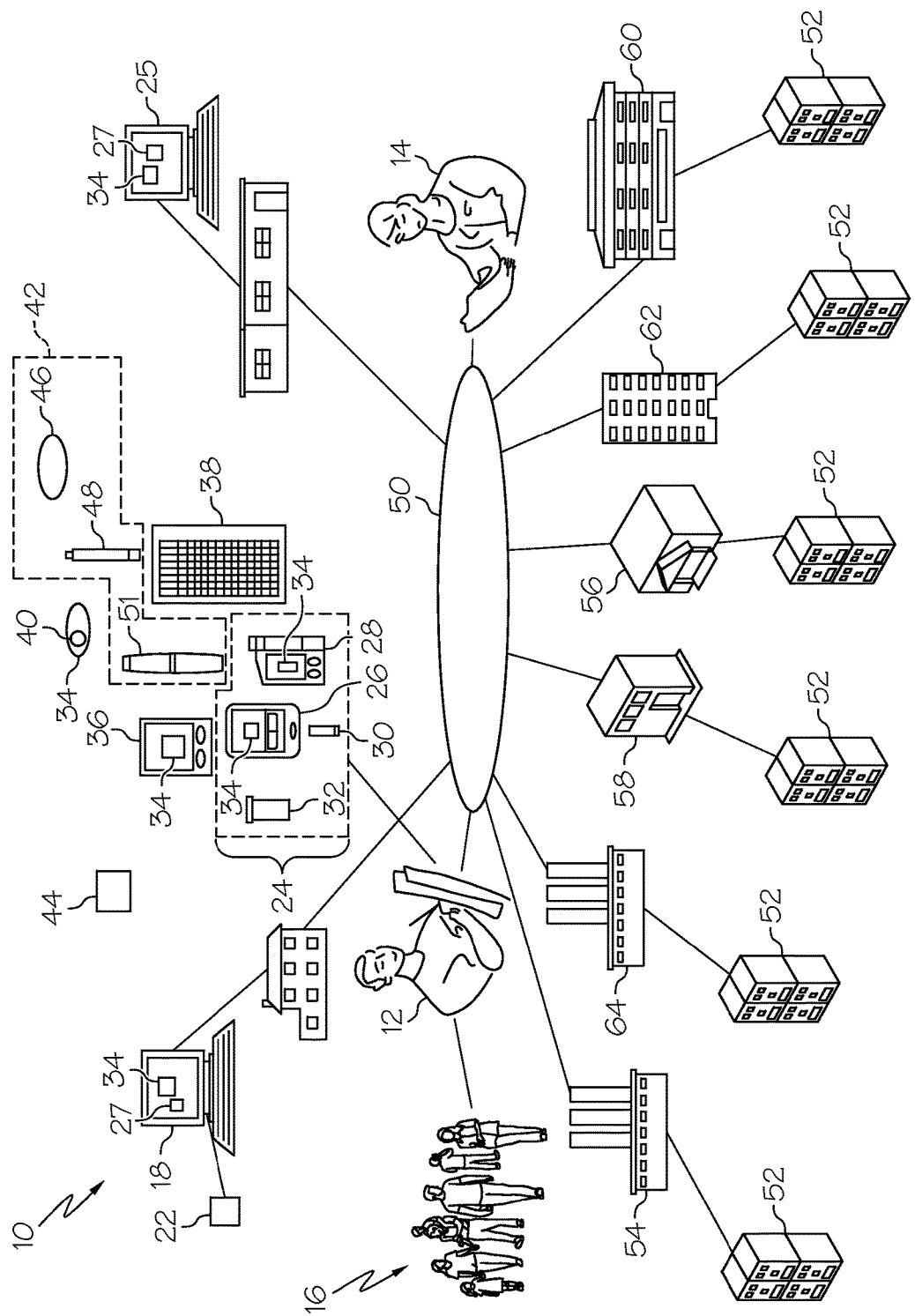
FIG. 1 is a diagram showing a care management system for an individual and a clinician along with others having an interest in the care management of the individual according to an embodiment of the present invention.

The present invention will be described below relative to various illustrative embodiments. Those skilled in the art will appreciate that the present invention may be implemented in a number of different applications and embodiments and is not specifically limited in its application to the particular embodiments depicted herein.

As used herein with the various illustrated embodiments described below, the following terms include, but are not limited to, the following meanings.

The term "biomarker" can mean a physiological variable measured to provide data relevant to an individual such as for example, a blood glucose value, an interstitial glucose value, an HbA1c value, a heart rate measurement, a blood pressure measurement, lipids, triglycerides, cholesterol, and the like.

The term "contextualizing" can mean documenting and interrelating conditions that exist or will occur surrounding a collection of a specific biomarker measurement. Preferably, data about documenting and interrelating conditions that exist or will occur surrounding a collection of a specific biomarker are stored together with the collected biomarker data and are linked to it. In particular, a further assessment of the collected biomarker data takes into account the data about documenting and interrelating conditions so that not only the data as such are evaluated but also the link between data to which it is contextualized. The data about documenting and interrelating conditions can include for example information about the time, food and/or exercises which occurs surrounding a collection of a specific biomarker measurement and/or simultaneously thereto. For example, the context of a structured collection procedure according to an embodiment of the present invention can be documented by utilizing entry criteria for verifying a fasting state with the user before accepting a biomarker value during a Basal titration optimization procedure.

The term "contextualized biomarker data" can mean the information on the interrelated conditions in which a specific biomarker measurement was collected combined with the measured value for the specific biomarker. In particular, the biomarker data are stored together with the information on the interrelated conditions under which a specific biomarker measurement was collected and are linked thereto.

The term "criteria" can mean one criterion or more criteria, and can be at least one or more of a guideline(s), rule(s), characteristic(s), and dimension(s) used to judge whether one or more conditions are satisfied or met to begin, accept, and/or end one or more procedural steps, actions, and/or values.

The term "adherence" can mean that a person following a structured collection procedure performs requested procedural steps appropriately. For example, the biomarker data should be measured under prescribed conditions of the structured collection procedure. If then the prescribed conditions are given for a biomarker measurement the adherence is defined as appropriate. For examples, the prescribed conditions are time related conditions and/or exemplarily can include eating of meals, taking a fasting sample, eating a type of meal with a requested window of time, taking a fasting sample at a requested time, sleeping a minimum amount of time, and the like. The adherence can be defined as appropriate or not appropriate for a structured collection procedure or a single data point in particular of a contextualized biomarker data. Preferably, the adherence can be defined as appropriate or not appropriate by a range of a prescribed condition(s) or by a selectively determined prescribed condition(s). Moreover the adherence can be calculated as a rate of adherence describing in which extent the adherence is given for a structured collection procedure or a single data point in particular of a contextualized biomarker data.

The term "adherence event" can mean when a person executing a structured collection procedure fails to perform a procedural step. For example, if a person did not collect data when requested by the collection device, the adherence is determined as not appropriate resulting in an adherence event. In another example, adherence criteria could be a first criterion for the individual to fast 6 hours and a second criterion for collecting a fasting bG value at a requested time. In this example, if the individual provides the bG sampling at the requested time but fasted only 3 hours before providing, then although the second adherence criterion is met, the first adherence criterion is not, and hence an adherence event for the first criterion would occur.

The term "violation event" is a form of an adherence event in which the person executing the structured collection (testing) procedure (protocol) does not administer a therapeutic at a recommended time, does not administer a recommended amount, or both.

The term "adherence criteria" can include adherence and can also mean a basis for comparison (e.g., assessment) of a measured value, a value related to a measured value and/or a calculated value with a defined value or defined range of the value wherein based on the comparison data are accepted with approval and positive reception. Adherence criteria can take into account time related values and/or adherence in one embodiment, but also can take into account noise in other embodiments, and the like. Furthermore, adherence criteria can be applied to contextualized biomarker data so that a biomarker data is accepted depending on a comparison of the contextualized data about documenting and interrelating conditions that exists or occurs surrounding the collection of the specific biomarker. Adherence criteria can be akin to a sanity check for a given piece of information, or group of information. Preferably, the single data point/information or group of data or information is rejected if the acceptance criterion is not fulfilled. In particular, such rejected data are then not used for further calculations which are used to provide a therapy recommendation. Mainly the rejected data are only used to assess the adherence and/or to trigger automatically at least one further action. For example, such a triggered action prompts the user then to follow a structured collection procedure or a single requested action so that based on that the adherence criteria can be fulfilled.

The term "data event request" can mean an inquiry for a collection of data at a single point in space-time defined by a special set of circumstances, for example, defined by time-related or not time-related events.

The term "decentralized disease status assessment" can mean a determination of the degree or extent of progression of a disease performed by using a biomarker measurement of interest to deliver a value without sending a sample to a laboratory for assessment.

The term "medical use case or question" can mean at least one or more of a procedure, situation, condition, and/or question providing an uncertainty about the factuality of existence of some medical facts, combined with a concept that is not yet verified but that if true would explain certain facts or phenomena. Medical use case or question can be already deposited and stored in the system so that the user can select between different medical use cases or questions. Alternatively, the medical use case or question can be defined by the user itself.

The term "determining" can mean any method that allows a decision to be made such as, foe example, by using an expert solution(s), game theory, quantitatively calculated, extracted from a data source, arrived at by comparison, logically deduced or any other suitable methods of determination.

The terms "software" and "program" may be used interchangeably herein.

FIG. 1 shows a care management system 10 for an individual 12 and a clinician(s) 14 along with others 16 having an interest in the care management of the individual 12. Individual 12, having dysglycemia, may include persons with a metabolic syndrome, pre-diabetes, type 1 diabetes, type 2 diabetes, and gestational diabetes. The others 16 with an interest in the individual's care may include family members, friends, support groups, and religious organizations all of which can influence the individual's conformance with a recommend therapy and/or behavioral change. The individual 12 may have access to a personal computer 18, such as a home computer, which can connect to a public network 50 (wired or wireless), such as the internet, cellular network, etc., and couple to a dongle, docking station, or device reader 22 for communicating with an external portable device, such as a portable collection device 24. An example of a device reader is shown in the manual "Accu-Chek® Smart Pix Device Reader User's Manual" (2008) available from Roche Diagnostics.

The collection device 24 can be essentially any portable electronic device that can function as an acquisition mechanism for determining and storing digitally a biomarker value(s) according to a structured collection procedure, and which can function to run the structured collection procedure and the method of the present invention. Greater details regarding various illustrated embodiments of the structured collection procedure are provided hereafter in later sections. In a preferred embodiment, the collection device 24 can be a self-monitoring blood glucose meter 26 or a continuous glucose monitor 28. An example of a blood glucose meter is the Accu-Chek® Active meter, and the Accu-Chek® Aviva meter described in the booklet "Accu-Chek® Aviva Blood Glucose Meter Owner's Booklet (2007), portions of which are disclosed in U.S. Pat. No. 6,645,368 B1 entitled "Meter and method of using the meter for determining the concentration of a component of a fluid" assigned to Roche Diagnostics Operations, Inc., which is hereby incorporated by reference. An example of a continuous glucose monitor is shown in U.S. Pat. No. 7,389,133 "Method and device for continuous monitoring of the concentration of an analyte" (Jun. 17, 2008) assigned to Roche Diagnostics Operations, Inc., which is hereby incorporated by reference.

In addition to the collection device 24, the individual 12 can use a variety of products to manage his or her diabetes including: test strips 30 carried in a vial 32 for use in the collection device 24; software 34 which can operate on the personal computer 18, the collection device 24, a handheld computing device 36, such as a laptop computer, a personal digital assistant, and/or a mobile phone; and paper tools 38. Software 34 can be pre-loaded or provided either via a computer readable medium 40 or over the public network 50 and loaded for operation on the personal computer 18, the collection device 24, the clinician computer/office workstation 25, and the handheld computing device 36, if desired. In still other embodiments, the software 34 can also be integrated into the device reader 22 that is coupled to the computer (e.g., computers 18 or 25) for operation thereon, or accessed remotely through the public network 50, such as from a server 52.

The individual 12 can also use for certain diabetes therapies additional therapy devices 42 and other devices 44. Additionally, therapy devices 42 can include devices such as an ambulatory infusion pump 46, an insulin pen 48, and a lancing device 51. An example of an ambulatory insulin pump 46 include but not limited thereto the Accu-Chek® Spirit pump described in the manual "Accu-Chek® Spirit Insulin Pump System Pump User Guide" (2007) available from Disetronic Medical Systems AG. The other devices 44 can be medical devices that provide data such as blood pressure, fitness devices that provide data such as exercise information, and elder care device that provide notification to care givers. The other devices 44 can be configured to communicate with each other according to standards planned by Continua® Health Alliance.

The clinicians 14 for diabetes are diverse and can include e.g., nurses, nurse practitioners, physicians, endocrinologists, and other such health care providers. The clinician 14 typically has access to a clinician computer 25, such as a clinician office computer, which can also be provided with the software 34. A healthcare record system 27, such as Microsoft® HealthVault™ and Google™ Health, may also be used by the individual 12 and the clinician 14 on computers 18, 25 to exchange information via the public network 50 or via other network means (LANs, WANs, VPNs, etc.), and to store information such as collection data from the collection device 24 to an electronic medical record of the individual e.g., EMR 53 (FIG. 2A) which can be provided to and from computer 18, 25 and/or server 52.

Figure 2:
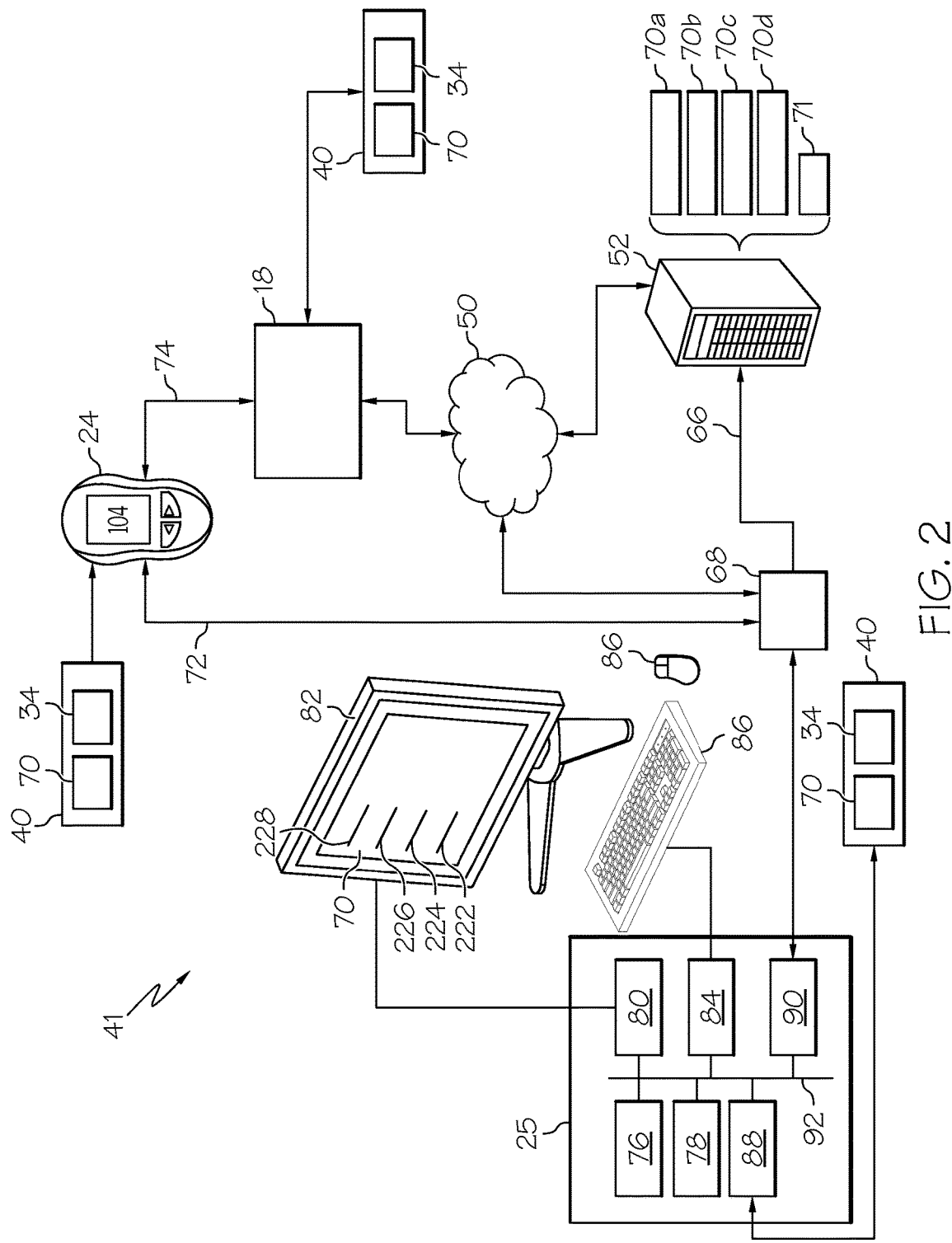
FIGS. 2 and 2A are diagrams showing embodiments of a system suitable for implementing a structured tailoring method according to an embodiment of the present invention.

Most individuals 12 and clinicians 14 can interact over the public network 50 with each other and with others having computers/servers 52. Such others can include the individual's employer 54, a third party payer 56, such as an insurance company who pays some or all of the individual's healthcare expenses, a pharmacy 58 that dispenses certain diabetic consumable items, a hospital 60, a government agency 62, which can also be a payer, and companies 64 providing healthcare products and services for detection, prevention, diagnosis and treatment of diseases. The individual 12 can also grant permissions to access the individual's electronic health record to others, such as the employer 54, the payer 56, the pharmacy 58, the hospital 60, and the government agencies 62 via the healthcare record system 27, which can reside on the clinician computer 25 and/or one or more servers 52. Reference hereafter is also made to FIG. 2.

FIG. 2 shows a system embodiment suitable for implementing a structured tailoring method according to an embodiment of the present invention, which in another embodiment can be a part of the care management system 10 and communicate with such components, via conventional wired or wireless communication means. The system 41 can include the clinician computer 25 that is in communication with a server 52 (e.g., data server, web server, combination thereof) as well as the collection device 24. Communications between the clinician computer 25 and the server 52 can be facilitated via a communication link to the public network 50, to a private network 66, or combinations thereof. The private network 66 can be a local area network or a wide are network (wired or wireless) connecting to the public network 50 via a network device 68 such as a (web) server, router, modem, hub, and the likes.

In one embodiment, the server 52 can be a central repository for a plurality of structured collection procedures (or protocols) 70a, 70b, 70c, 70d, in which the details of a few exemplary structured collection procedures are provided in later sections. The server 52, as well as the network device 68, can function also as a data aggregator for completed ones of the structured collection procedures 70a, 70b, 70c, 70d. Accordingly, in such an embodiment, data of a completed collection procedure(s) from a collection device of the individual 12 can then be provided from the server 52 and/or network device 68 to the clinician computer 25 when requested in response to retrieval for such data.

Figure 2A:
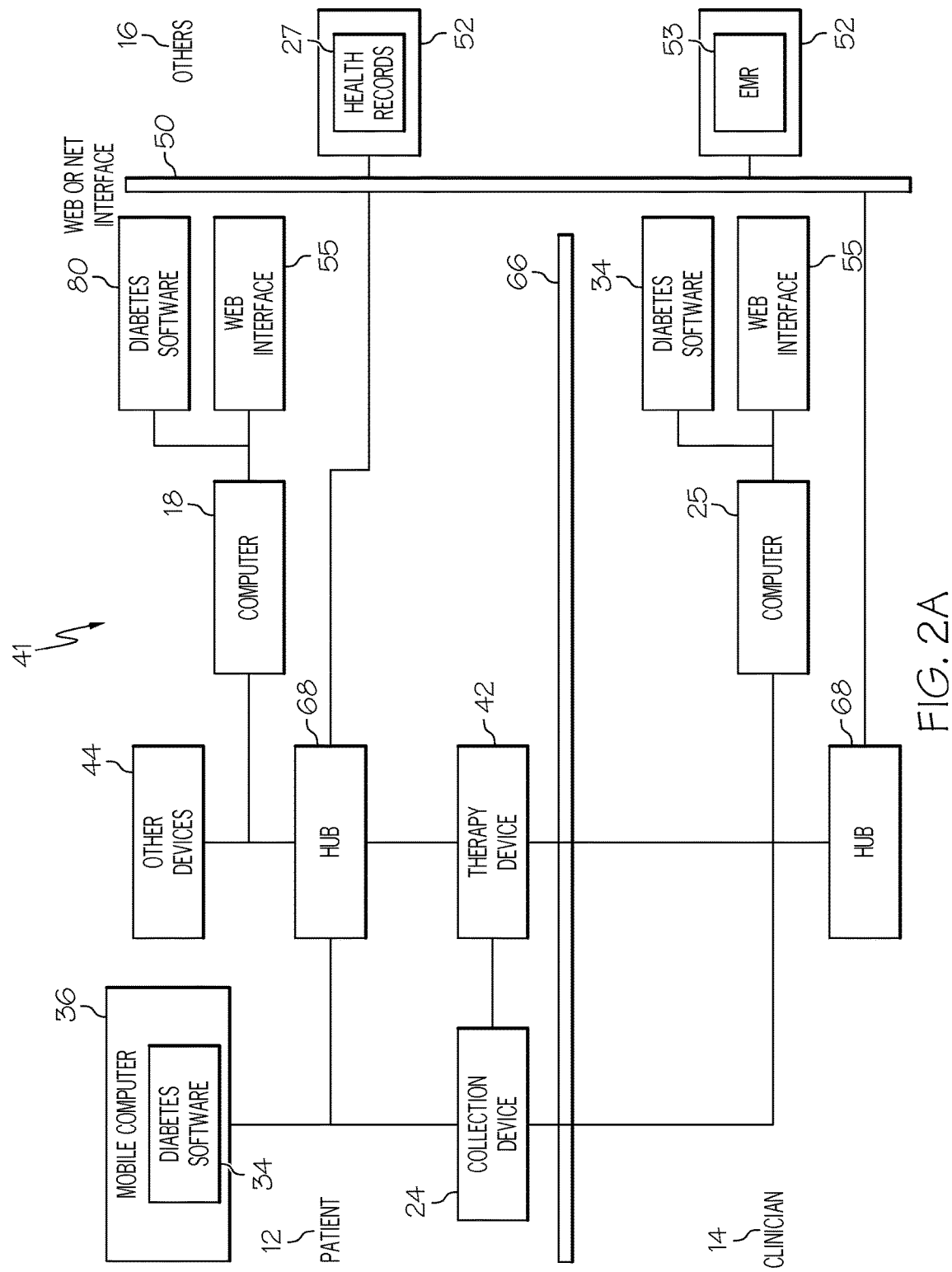

In one embodiment, one or more of the plurality of structured collection procedures 70a, 70b, 70c, 70d on the server 52 can be provided over the public network 50, such as through a secure web interface 55 (FIG. 2A, showing another embodiment of the system 41) implemented on personal computer 18, the clinician computer 25, and/or the collection device 24. In another embodiment, the clinician computer 25 can serve as the interface (wired or wireless) 72 between the server 52 and the collection device 24. In still another embodiment, the structured collection procedures 70a, 70b, 70c, 70d, as well as software 34, may be provided on a computer readable medium 40 and loaded directly on personal computer 18, the clinician computer 25, and/or the collection device 24. In still another embodiment, the structured collection procedures 70a, 70b, 70c, 70d may be provided pre-loaded (embedded) in memory of the collection device 24. In still other embodiments, new/updated/modified structured collection procedures 70a, 70b, 70c, 70d may be sent between personal computer 18, the clinician computer 25, server 52 and/or the collection device 24 via the public network 50, the private network 66, via a direct device connection (wired or wireless) 74, or combinations thereof. Accordingly, in one embodiment the external devices e.g., computer 18 and 25, can be used to establish a communication link 72, 74 between the collection device 24 and still further electronic devices such as other remote Personal Computer (PC), and/or servers such as through the public network 50, such as the Internet and/or other communication networks (e.g., LANs, WANs, VPNs, etc.), such as private network 66.

Figure 3:
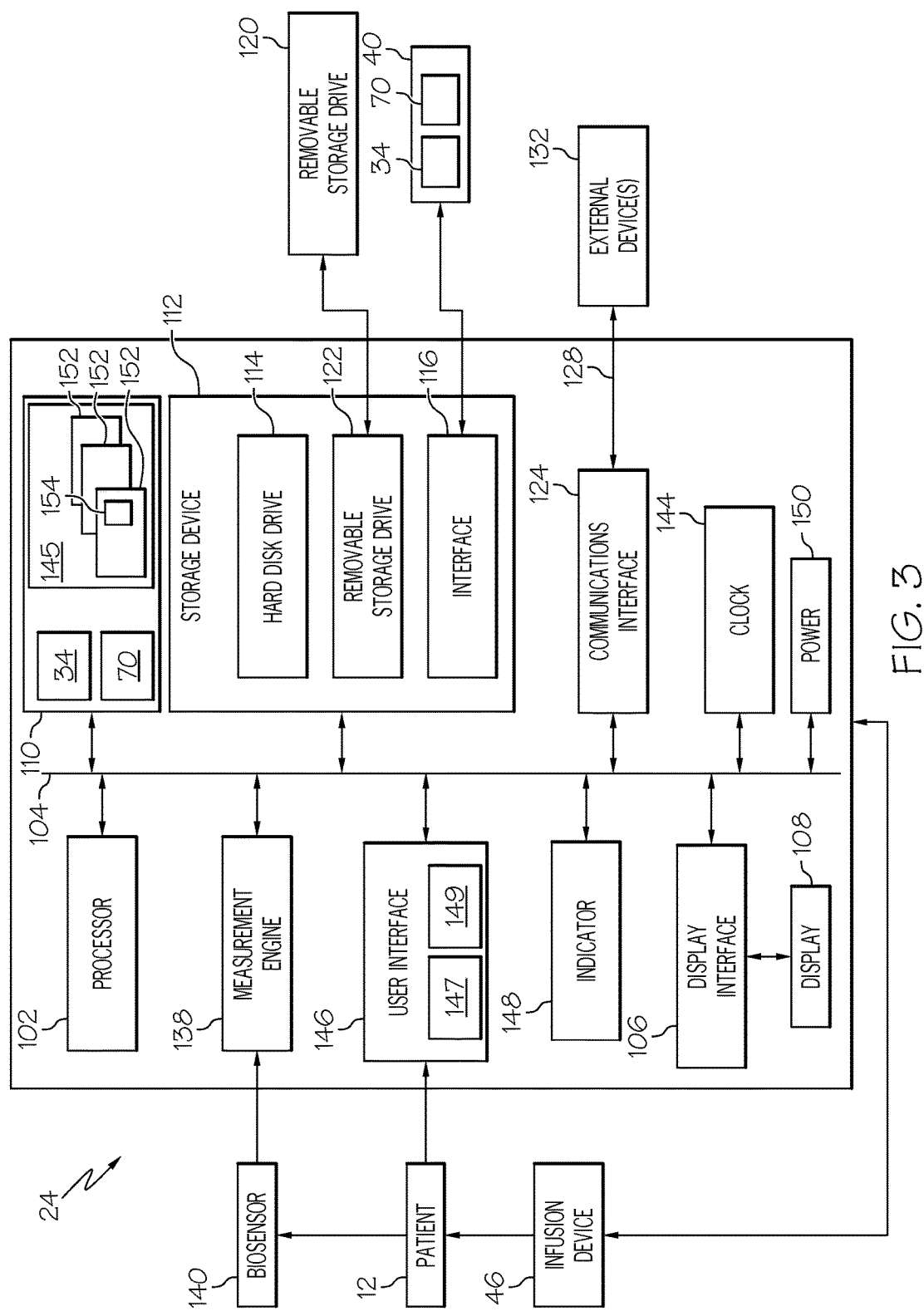
FIG. 3 shows a block diagram of a collection device embodiment according to the present invention.

The clinician computer 25, as a conventional personal computer/workstation, can include a processor 76 which executes programs, such as software 34, and such as from memory 78 and/or computer readable medium 40. Memory 78 can include system memory (RAM, ROM, EEPROM, etc.), and storage memory, such as hard drives and/or flash memory (internal or external). The clinician computer 25 can also include a display driver 80 to interface a display 82 with the processor 76, input/output connections 84 for connecting user interface devices 86, such as a keyboard and mouse (wired or wireless), and computer readable drives 88 for portable memory and discs, such as computer readable medium 40. The clinician computer 25 can further include communication interfaces 90 for connections to the public network 50 and other devices, such as collection device 24 (wired or wireless), and a bus interface 92 for connecting the above mentioned electronic components to the processor 76. Reference hereafter is now made to FIG. 3.

FIG. 3 is a block diagram conceptually illustrating the portable collection device 24 depicted in FIG. 2. In the illustrated embodiment, the collection device 24 can include one or more microprocessors, such as processor 102, which may be a central processing unit comprising at least one more single or multi-core and cache memory, which can be connected to a bus 104, which may include data, memory, control and/or address buses. The collection device 24 can include the software 34, which provides instruction codes that causes a processor 102 of the device to implement the methods of the present invention that are discussed hereafter in later sections. The collection device 24 may include a display interface 106 providing graphics, text, and other data from the bus 104 (or from a frame buffer not shown) for display on a display 108, by which the processor 102 can instruct/provide instructions/information/questions/guidance to a user. The display interface 106 may be a display driver of an integrated graphics solution that utilizes a portion of main memory 110 of the collection device 24, such as random access memory (RAM) and processing from the processor 102 or may be a dedicated graphic processing unit. In another embodiment, the display interface 106 and display 108 can additionally provide a touch screen interface for providing data to the collection device 24 in a well-known manner.

Main memory 110 in one embodiment can be random access memory (RAM), and in other embodiments may include other memory such as a ROM, PROM, EPROM or EEPROM, and combinations thereof. In one embodiment, the collection device 24 can include secondary memory 112, which may include, for example, a hard disk drive 114 and/or a computer readable medium drive 116 for the computer readable medium 40, representing for example, at least one of a floppy disk drive, a magnetic tape drive, an optical disk drive, a flash memory connector (e.g., USB connector, Firewire connector, PC card slot), etc. The drive 116 reads from and/or writes to the computer readable medium 40 in a well-known manner. Computer readable medium 40, represents a floppy disk, magnetic tape, optical disk (CD or DVD), flash drive, PC card, etc. which is read by and written to by the drive 116. As will be appreciated, the computer readable medium 40 can have stored therein the software 34 and/or structured collection procedures 70a, 70b, 70c, and 70d as well as data resulting from completed collections performed according to one or more of the collection procedures 70a, 70b, 70c, and 70d.

In alternative embodiments, secondary memory 112 may include other means for allowing the software 34, the collection procedures 70a, 70b, 70c, 70d, other computer programs or other instructions to be loaded into the collection device 24. Such means may include, for example, a removable storage unit 120 and an interface connector 122. Examples of such removable storage units/interfaces can include a program cartridge and cartridge interface, a removable memory chip (e.g., ROM, PROM, EPROM, EEPROM, etc.) and associated socket, and other removable storage units 120 (e.g. hard drives) and interface connector 122 which allow software and data to be transferred from the removable storage unit 120 to the collection device 24.

The collection device 24 in one embodiment can include a communication module 124. The communication module 124 allows software (e.g., the software 34, the collection procedures 70a, 70b, 70c, and 70d) and data (e.g., data resulting from completed collections performed according to one or more of the collection procedures 70a, 70b, 70c, and 70d) to be transferred between the collection device 24 and an external device(s) 126. Examples of communication module 124 may include one or more of a modem, a network interface (such as an Ethernet card), a communications port (e.g., USB, firewire, serial, parallel, etc.), a PC or PCMCIA slot and card, a wireless transceiver, and combinations thereof. The external device(s) 126 can be the personal computer 18, the clinician computer 25, the handheld computing devices 36, such as a laptop computer, a personal digital assistance (PDA), a mobile (cellular) phone, and/or a dongle, a docking station, or device reader 22. In such an embodiment, the external device 126 may provided and/or connect to one or more of a modem, a network interface (such as an Ethernet card), a communications port (e.g., USB, firewire, serial, parallel, etc.), a PCMCIA slot and card, a wireless transceiver, and combinations thereof for providing communication over the public network 50 or private network 66, such as with the clinician computer 25 or server 52. Software and data transferred via communication module 124 can be in the form of wired or wireless signals 128, which may be electronic, electromagnetic, optical, or other signals capable of being sent and received by communication module 124. For example, as is known, signals 128 may be sent between communication module 124 and the external device(s) 126 using wire or cable, fiber optics, a phone line, a cellular phone link, an RF link, an infrared link, other communications channels, and combinations thereof. Specific techniques for connecting electronic devices through wired and/or wireless connections (e.g. USB and Bluetooth, respectively) are well known in the art.

In another embodiment, the collection device 24 can be used with the external device 132, such as provided as a handheld computer or a mobile phone, to perform actions such as prompt an individual to take an action, acquire a data event, and perform calculations on information. An example of a collection device combined with such an external device 126 provided as a hand held computer is disclosed in U.S. patent application Ser. No. 11/424,757 filed Jun. 16, 2006 entitled "System and method for collecting patient information from which diabetes therapy may be determined," assigned to Roche Diagnostics Operations, Inc., which is hereby incorporated by reference. Another example of a handheld computer is shown in the user guide entitled "Accu-Chek® Pocket Compass Software with Bolus Calculator User Guide" (2007) available from Roche Diagnostics.

In the illustrative embodiment, the collection device 24 can provide a measurement engine 138 for reading a biosensor 140. The biosensor 140, which in one embodiment is the disposable test strip 30 (FIG. 1), is used with the collection device 24 to receive a sample such as for example, of capillary blood, which is exposed to an enzymatic reaction and measured by electrochemistry techniques, optical techniques, or both by the measurement engine 138 to measure and provide a biomarker value, such as for example, a blood glucose level. An example of a disposable test strip and measurement engine is disclosed in U.S. Patent Pub. No. 2005/0016844 A1 "Reagent stripe for test strip" (Jan. 27, 2005), and assigned to Roche Diagnostics Operations, Inc., which is hereby incorporated by reference. In other embodiments, the measurement engine 138 and biosensor 140 can be of a type used to provide a biomarker value for other types of sampled fluids or analytes besides or in addition to glucose, heart rate, blood pressure measurement, and combinations thereof. Such an alternative embodiment is useful in embodiments where values from more then one biomarker type are requested by a structured collection procedure according to the present invention. In still another embodiment, the biosensor 140 may be a sensor with an indwelling catheter(s) or being a subcutaneous tissue fluid sampling device(s), such as when the collection device 24 is implemented as a continuous glucose monitor (CGM) in communication with an infusion device, such as pump 46

(FIG. 1). In still another embodiments, the collection device 24 can be a controller implementing the software 34 and communicating between the infusion device (e.g., ambulatory infusion pump 46 and electronic insulin pen 48) and the biosensor 140.

Data, comprising at least the information collected by the biosensor 140, is provided by the measurement engine 138 to the processor 102 which may execute a computer program stored in memory 110 to perform various calculations and processes using the data. For example, such a computer program is described by U.S. patent application Ser. No. 12/492,667, filed Jun. 26, 2009, titled "Method, System, and Computer Program Product for Providing Both an Estimated True Mean Blood Glucose Value and Estimated Glycated Hemoglobin (HbA1C) Value from Structured Spot Measurements Of Blood Glucose," and assigned to Roche Diagnostics Operations, Inc., which is hereby incorporated by reference. The data from the measurement engine 138 and the results of the calculation and processes by the processor 102 using the data is herein referred to as self-monitored data. The self-monitored data may include, but not limited thereto, the glucose values of a individual 12, the insulin dose values, the insulin types, and the parameter values used by processor 102 to calculate future glucose values, supplemental insulin doses, and carbohydrate supplement amounts as well as such values, doses, and amounts. Such data along with a date-time stamp 169 for each measured glucose value and administered insulin dose value is stored in a data file 145 of memory 110 and/or 112. An internal clock 144 of the collection device 24 can supply the current date and time to processor 102 for such use.

The collection device 24 can further provide a user interface 146, such as buttons, keys, a trackball, touchpad, touch screen, etc. for data entry, program control and navigation of selections, choices and data, making information requests, and the likes. In one embodiment, the user interface 146 can comprises one or more buttons 147, 149 for entry and navigation of the data provided in memory 110 and/or 112. In one embodiment, the user can use one or more of buttons 147, 149 to enter (document) contextualizing information, such as data related to the everyday lifestyle of the individual 12 and to acknowledge that prescribed tasks are completed. Such lifestyle data may relate to food intake, medication use, energy levels, exercise, sleep, general health conditions and overall well-being sense of the individual 12 (e.g., happy, sad, rested, stressed, tired, etc.). Such lifestyle data can be recorded into memory 110 and/or 112 of the collection device 24 as part of the self-monitored data via navigating through a selection menu displayed on display 108 using buttons 147, 149 and/or via a touch screen user interface provided by the display 108. It is to be appreciated that the user interface 146 can also be used to display on the display 108 the self monitored data or portions thereof, such as used by the processor 102 to display measured glucose levels as well as any entered data.

In one embodiment, the collection device 24 can be switched on by pressing any one of the buttons 147, 149 or any combination thereof. In another embodiment, in which the biosensor 140 is a test-strip, the collection device 24 can be automatically switched on when the test-strip is inserted into the collection device 24 for measurement by the measurement engine 138 of a glucose level in a sample of blood placed on the test-strip. In one embodiment, the collection device 24 can be switched off by holding down one of the buttons 147, 149 for a pre-defined period of time, or in another embodiment can be shut down automatically after a pre-defined period of non-use of the user interface 146.

An indicator 148 can also be connected to processor 102, and which can operate under the control of processor 102 to emit audible, tactile (vibrations), and/or visual alerts/reminders to the individual of daily times for bG measurements and events, such as for example, to take a meal, of possible future hypoglycemia, and the likes. A suitable power supply 150 is also provided to power the collection device 24 as is well known to make the device portable.

As mentioned above previously, the collection device 24 may be pre-loaded with the software 34 or by provided therewith via the computer readable medium 40 as well as received via the communication module 124 by signal 128 directly or indirectly though the external device 132 and/or network 50. When provided in the latter matter, the software 34 when received by the processor 102 of the collection device 24 is stored in main memory 110 (as illustrated) and/or secondary memory 112. The software 34 contains instructions, when executed by the processor 102, enables the processor to perform the features/functions of the present invention as discussed herein in later sections. In another embodiment, the software 34 may be stored in the computer readable medium 40 and loaded by the processor 102 into cache memory to cause the processor 102 to perform the features/functions of the invention as described herein. In another embodiment, the software 34 is implemented primarily in hardware logic using, for example, hardware components such as application specific integrated circuits (ASICs). Implementation of the hardware state machine to perform the feature/functions described herein will be apparent to persons skilled in the relevant art(s). In yet another embodiment, the invention is implemented using a combination of both hardware and software.

In an example software embodiment of the invention, the methods described hereafter can be implemented in the C++ programming language, but could be implemented in other programs such as, but not limited to, Visual Basic, C, C#, Java or other programs available to those skilled in the art. In still other embodiment, the program 34 may be implemented using a script language or other proprietary interpretable language used in conjunction with an interpreter. Reference hereafter is also made to FIG. 4.

FIG. 4 depicts in tabular form a data file 145 containing data records 152 of self-monitored data 154 resulting from a structured collection procedure according to an embodiment of the present invention. The data records 152 (e.g., rows) along with the self-monitoring data 154 (e.g., various one of the columns) can also provide associated therewith contextual information 156 (e.g., other various ones of the columns as well as via row and column header information). Such contextual information 156 can be collected either automatically, such as for example via input received automatically from the measurement engine, the biosensor, and/ or any one of the other devices, or via input received from the user interface which was manually enter by the individual in response to a collection request (e.g., a question displayed by the processor 102 on the display 108) during the structured collection procedure. Accordingly, as such contextual information 156 can be provided with each data record 152 in a preferred embodiment, such information is readily available to a physician and no further collection of such information is necessarily needed to be provided again by the individual either manually or orally after completing the structured collection procedure. In another embodiment, if such contextual information 156 and/or additional contextual information is collected after completion of a structured collection procedure according to the present invention, such information may be provided in the associated data file and/or record 145, 152 at a later time such as via one of the computers 18, 25. Such information would then be associated with the self-monitored data in the data file 145, and thus would not need to be provided again orally or manually. Such a process in the latter embodiment may be needed in the situation where the structured collection procedure is implemented as or partly as a paper tool 38 which is used with a collection device incapable of running the software 34 implementing such a structured collection procedure.

It is to be appreciated that the date file 145 (or portions thereof, such as only the self-monitored data 154) can be sent/downloaded (wired or wireless) from the collection device 24 via the communication module 124 to another electronic device, such the external device 132 (PC, PDA, or cellular telephone), or via the network 50 to the clinician computer 25. Clinicians can use software provided on the clinician computer 25 to evaluate the received self-monitored data 154 as well as the contextual information 156 of the individual 12 for therapy results. An example of some of the functions which may be incorporated into the software and which is configured for a personal computer is the Accu-Chek® 360 Diabetes Management System available from Roche Diagnostics that is disclosed in U.S. patent application Ser. No. 11/999,968 filed Dec. 7, 2007, titled "METHOD AND SYSTEM FOR SETTING TIME BLOCK," and assigned to Roche Diagnostics Operations, Inc., which is hereby incorporated by reference.

In a preferred embodiment, the collection device 24 can be provided as portable blood glucose meter, which is used by the individual 12 for recording self-monitored data comprising insulin dosage readings and spot measured glucose levels. Examples of such bG meters as mentioned above previously include but are not limited to, the Accu-Chek® Active meter and the Accu-Chek® Aviva system both by Roche Diagnostics, Inc. which are compatible with the Accu-Chek® 360° Diabetes management software to download test results to a personal computer or the Accu-Chek® Pocket Compass Software for downloading and communication with a PDA. Accordingly, it is to be appreciated that the collection device 24 can include the software and hardware necessary to process, analyze and interpret the self monitored data in accordance with predefined flow sequences (as described below in detail) and generate an appropriate data interpretation output. In one embodiment, the results of the data analysis and interpretation performed upon the stored data by the collection device 24 can be displayed in the form of a report, trend-monitoring graphs, and charts to help individuals manage their physiological condition and support patient-doctor communications. In other embodiments, the bG data from the collection device 24 may be used to generated reports (hardcopy or electronic) via the external device 132 and/or the personal computer 18 and/or the clinician computer 25.

The collection device 24 can further provide the individual and/or his or her clinician with at least one or more of the capabilities comprising: a) editing data descriptions, e.g. the title and description of a record; b) saving records at a specified location, in particular in user-definable directories as described above; c) recalling records for display; d) searching records according to different criteria (date, time, title, description etc.); e) sorting records according to different criteria (e.g., values of the bG level, date, time, duration, title, description, etc.); f) deleting records; g) exporting records; and/or h) performing data comparisons, modifying records, excluding records as is well known.

As used herein, lifestyle can be described in general as a pattern in an individual's habits such as meals, exercise, and work schedule. The individual additionally may be on medications such as insulin therapy or orals that they are required to take in a periodic fashion. Influence of such action on glucose is implicitly considered by the present invention, and the control of which can be the one of the long term goal of the individual.

It is to be appreciated that the processor 102 of the collection device 24 can implement one or more structured collection procedures 70 provided in memory 110 and/or 112. Each structured collection procedure 70 in one embodiment can be stand-alone software, thereby providing the necessary program instructions which when executed by the processor 102 causes the processor to perform the structured collection procedure 70 as well as other prescribed functions. In other embodiments, each structured collection procedure 70 can be part of the software 34, and can be then be selectively executed by the processor 102 either via receiving a selection from a menu list provided in the display 108 from the user interface 146 in one embodiment or via activation of a particular user interface, such as a structured collection procedure run mode button (not shown) provided to the collection device 24 in another embodiment. It is to be appreciated that the software 34, likewise, provides the necessary program instructions which when executed by the processor 102 causes the processor to perform the structured collection procedure 70 as well as other prescribed functions of the software 34 discussed herein. One suitable example of having a selectable structured collection procedure provided as a selectable mode of a collection meter is disclosed by in U.S. patent application Ser. No. 12/491,523, filed Jun. 25, 2009, titled "Episodic Blood Glucose Monitoring System With An Interactive Graphical User Interface And Methods Thereof," assigned to Roche Diagnostics Operations, Inc., which is hereby incorporated by reference.

In still another embodiment, a command instruction can be sent from the clinician computer 25 and received by the processor 102 via the communication module 124, which places the collection device 24 in a collection mode which runs automatically the structured collection procedure 70. Such a command instruction may specify which of the one or more structured collection procedures to run and/or provide a structured collection procedure to run. In still another embodiment, a list of defined medical use cases or medical questions can be presented on the display 108 by the processor 102, and a particular structured collection procedure 70 can be automatically chosen by the processor 102 from a plurality of structured collection procedures (e.g., procedures 70a, 70b, 70c, and 70d) depending on the selection of the defined medical use cases or medical questions received by the processor 102 via the user interface 146.

In still another embodiment, after selection, the structured collection procedure(s) 70 can be provided through the computer readable medium e.g., 40 and loaded by the collection device 24, downloaded from computer 18 or 25, the other device(s) 132, or server 52. Server 52, for example, may be a healthcare provider or company providing such pre-defined structured collection procedures 70 for downloading according to a selected defined medical use case or question. It is to be appreciated that the structured collection procedure(s) 70 may be developed by a healthcare company (e.g. company 64) and implemented via the public network 50 through a webpage which can be accessed via standard browser and run on the device 24 (if web enabled) and personal computer 18 and/or clinician computer 25, and/or made available for downloading on server 52, such as illustrated in FIG. 2. In still other embodiments, notices that a new structured collection procedure 70 is available for use on the collection device 24 to help address a particular use case/medical question that a user (e.g., healthcare provider and patient) may have can be provided in any standard fashion, such for via postal letters/cards, email, text messaging, tweets, and the likes.

In still another embodiment, the software 34 can be implemented on the continuous glucose monitor 28 (FIG. 1). In this manner, the continuous glucose monitor 28 can be used to obtain time-resolved data. Such time-resolved data can be useful to identify fluctuations and trends that would otherwise go unnoticed with spot monitoring of blood glucose levels and standard HbA1c tests. Such as, for example, low overnight glucose levels, high blood glucose levels between meals, and early morning spikes in blood glucose levels as well as how diet and physical activity affect blood glucose along with the effect of therapy changes.

In addition to collection device 24 and software 34, clinicians 14 can prescribe other diabetes therapy devices for individuals 12 such as an ambulatory insulin pump 46 as well as electronically based insulin pen 48 (FIG. 1). The insulin pump 46 typically includes configuration software such as that disclosed in the manual "Accu-Chek® Insulin Pump Configuration Software" also available from Disetronic Medical Systems AG. The insulin pump 46 can record and provide insulin dosage and other information, as well as the electronically based insulin pen 48, to a computer, and thus can be used as another means for providing biomarker data as requested by the structured collection procedure 70 (FIG. 2) according to the present invention.

It is to be appreciated that one or more of the method steps discussed hereafter can be configured as a paper tool 38 (FIG. 1) e.g. as a form, checklist, journal, etc., but preferably all the method steps are facilitated electronically on system 41 (FIG. 2) or on any electronic device/computer, such as collection device 24, having a processor and memory as a program(s) residing in memory. As is known, when a computer executes the program, instructions codes of the program cause the processor of the computer to perform the method steps associated therewith. In still other embodiments, some or all of the method steps discussed hereafter can be configured on computer readable medium 40 storing instruction codes of a program that, when executed by a computer, cause the processor of the computer to perform the method steps associated therewith. These method steps are now discussed in greater detail hereafter with reference made to FIGS. 5A and 5B.

Create a Structured Collection Procedure

Figure 5A:
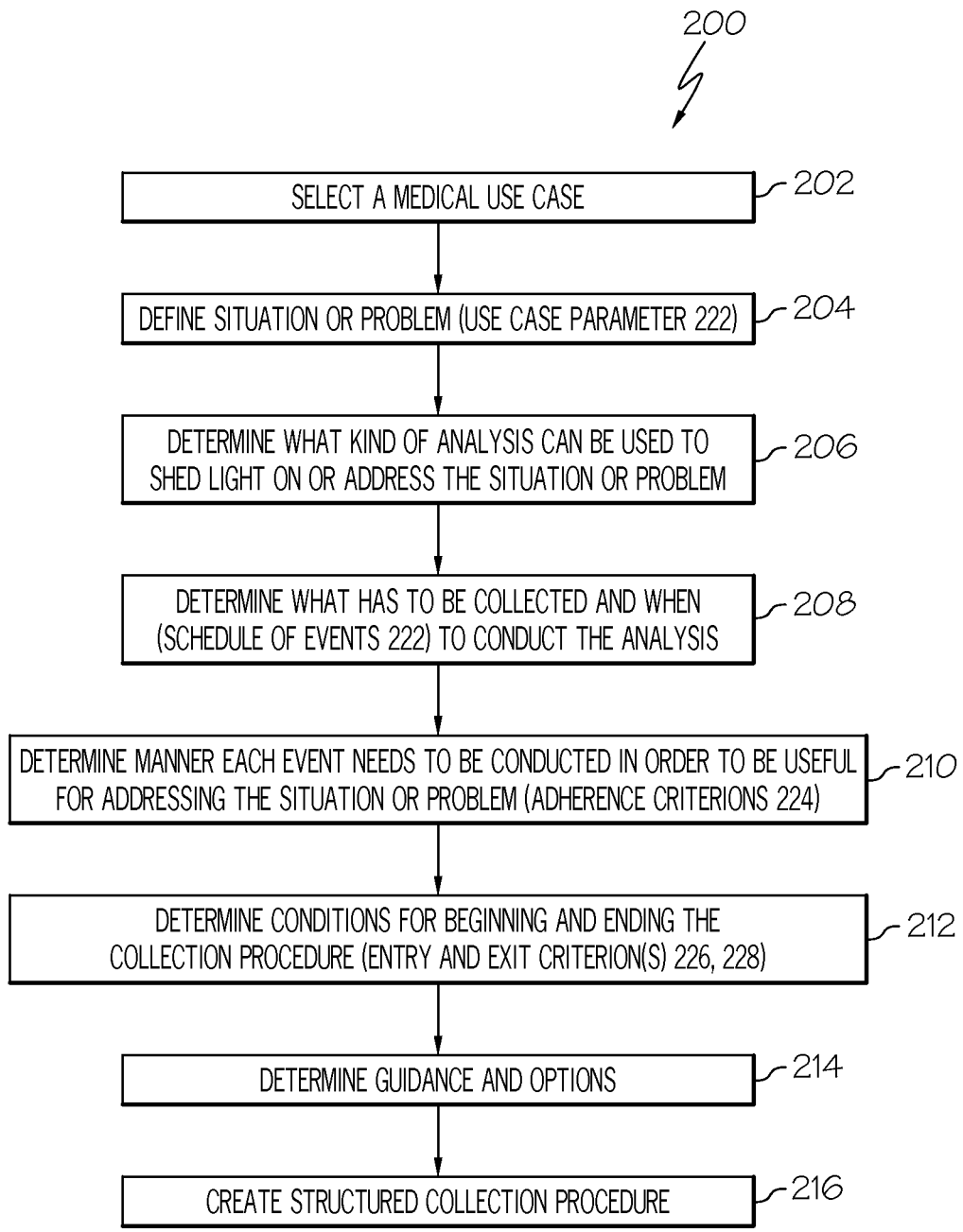
FIG. 5A depicts a method of creating a structured collection procedure.
Figure 5B:
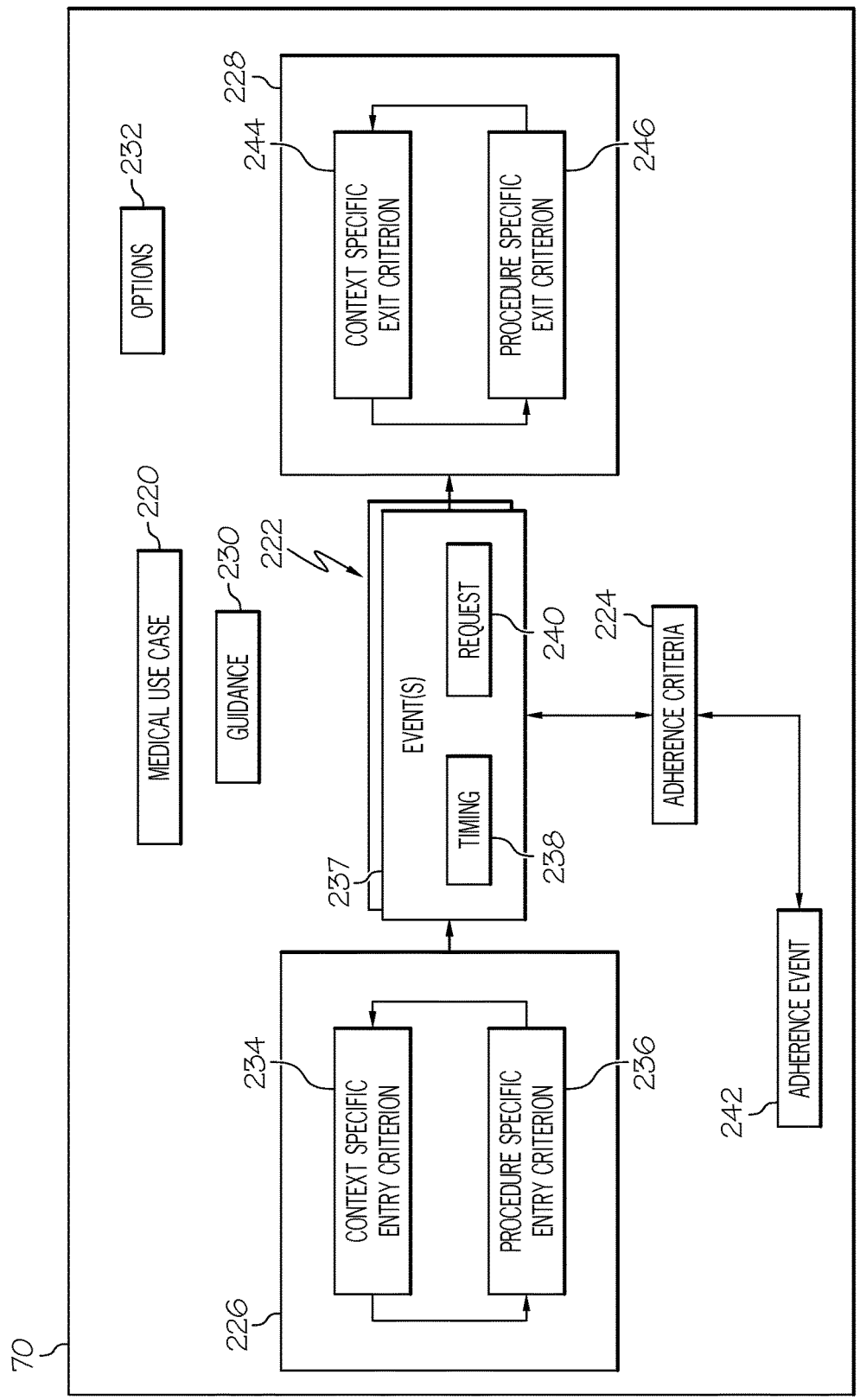
FIGS. 5B and 5C show parameters defining a structured collection procedure and factors which can be considered to optimize an individual's therapy using the structured collection procedure, respectively, according to one or more embodiments of the present invention.

FIG. 5A depicts a method 200 of creating a structured collection procedure 70 illustrated by FIG. 5B for a medical use case or question which may be implemented in any one of the above described devices 18, 24, 25, 26, 28, 36, 52 as stand alone software, as part of the diabetes software 34 or portions there of as part of paper tool 38. In step 202, a medical use case or question, hereafter referred to generally as use case(s), is selected and/or can be defined. It is to be appreciated that a use case may be, for example, one selected from the following medical use cases or questions: a desire to know the effects of eating a particular food; a desire to know the best time to take medication before and/or after with a meal; and a desire to know the effects of exercise on bG levels. Other use cases may be questions concerning finding a diagnosis, how best to initialize therapy for an individual, finding a determination of status of an individual's disease progression, finding the best ways to optimize an individual's therapy, change an individual's current behavior to a targeted behavior, and the like. Still other examples can be providing such structured collection procedures 70 which can be used to help address medical questions regarding fasting blood glucose, pre-prandial glucose values, post-prandial glucose values, and the like. Other medical questions can be to control the biomarker in a predefined context, to optimize the biomarker in a predefined context, related to therapy onset, type of therapy, oral mono-therapy, oral combination therapy, insulin therapy, lifestyle therapy, adherence to therapy, therapy efficacy, insulin injection or inhalation, type of insulin, split of insulin in basal and bolus, and the likes. The selected use case can be assigned to a medical use case parameter 220 depicted in FIG. 5B.

Figure 5C:
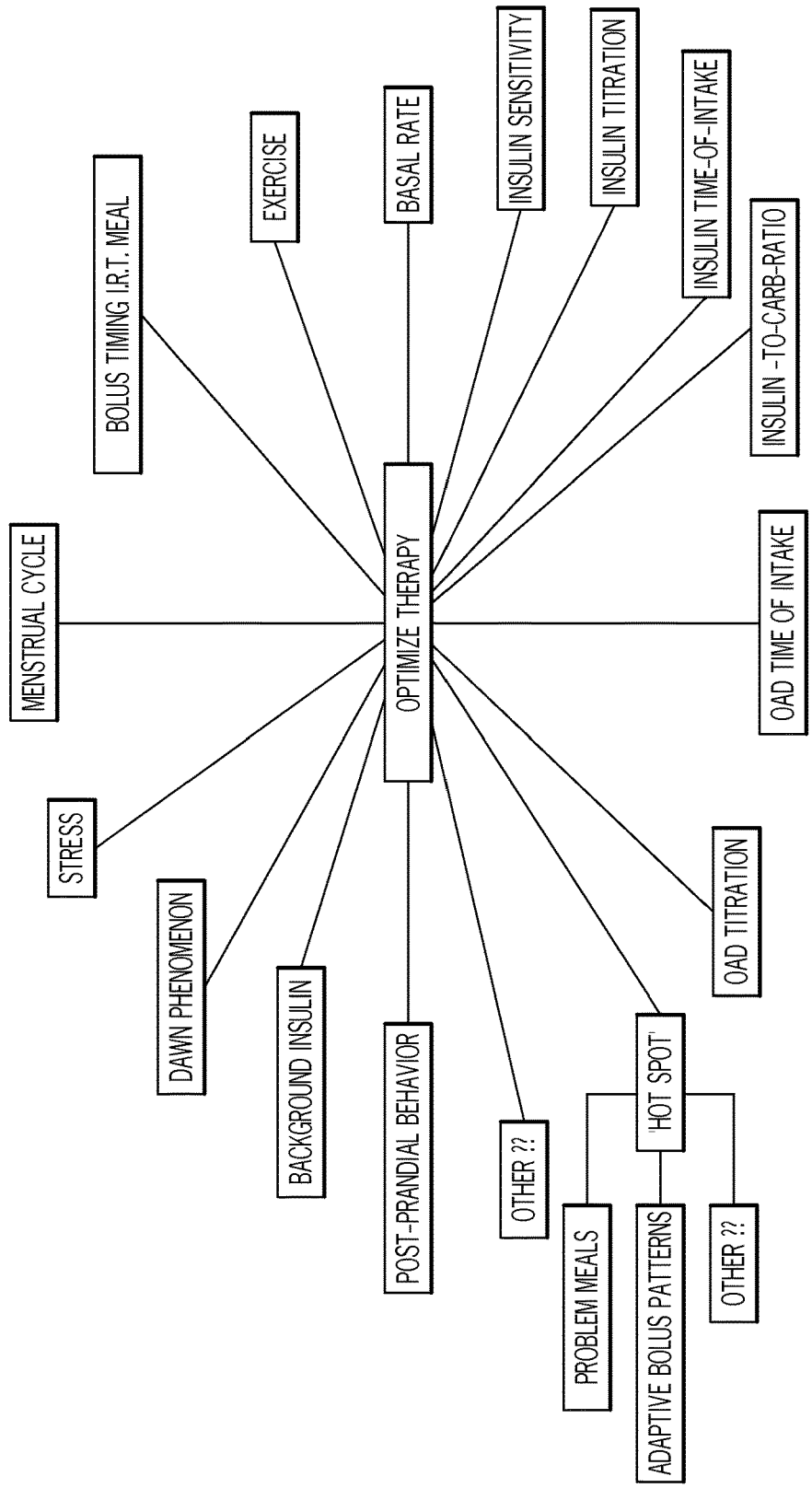

In step 204, the situation or problem surrounding the selected use case can be defined. This can be accomplished via looking at all the factors which may affect a change in the use case. For example, in the use case of desiring to know how best to optimize the individual's therapy and/or to change a current behavior, some factors to look at may include stress, menstrual cycle, pre-dawn effect, background insulin, exercise, bolus timing with respect to a meal, basal rate, insulin sensitivity, post-prandial behavior, and the like such as shown by FIG. 5C.

In step 206, a determination can be made as to what kinds of analysis can be used to address or shed light on the situation or the problem. Such analysis may be, for example, selected from the following: evaluating the change in fasting blood glucose (FPG) values over the course of the collection procedure 70, monitoring one or more particular value over the duration of the collection procedure 70, determining an insulin to carbohydrate (I:C) ratio, determining insulin sensitivity, determining best time for administering a drug with respect to another variable, such as meal(s), and the like. In step 208, a sampling group determination can be made as to which information has to be collected, such as what biomarker(s) and the context(s) in which the biomarkers shall be collected, as well as when this information needs to be collected to conduct the analysis. For example, the sampling group can be defined as a string of data objects, each of which consists of: target type, e.g., time based which can use a target time (e.g., used for an alerting feature), a lower time window bound, an upper time window bound, etc., or data based which defines a data type (single, aggregate, or formula), the conditions for accepting the data (e.g., none, below a value, above a value, a formula, etc.), the type of collection (e.g., user input, sensor, data, etc.), as well as any reminder screen text (e.g., static, and/or dynamic in both formatting and value insertion) for each collection. The result of this process is a schedule of collection events 222 (FIG. 5B) containing one or more events 237. It is to be appreciated that the schedule of collection events 222 of the structured collection procedure 70 for some uses cases can be a simple data collection schedule e.g., one which presents as an event 237 questions to the patient 12 as to whether or not a desire action was accomplished as scheduled, such as in the use case of changing a behavior of the patient to a target behavior, e.g., exercising for a desired period of time per day, not smoking for a period of time each day, not eating particular foods after a certain time of day, eating particular foods at each meal per day, and the likes. For other uses cases, the schedule of collection events 222 in the structured collection procedure 70 can be a complex data collection which requires multiple actions and biomarker inputs from the patient 12 to be accomplished as scheduled.

Next in step 210, the manner in which each event 237 or a group of the schedule of collection events 222 is/are to be conducted in order to be useful for addressing the situation or problem of the selected use case is then determined. This results in one or more adherence criteria 224. In addition to and/or instead of the manner for performing a collection, the adherence criteria 224 may also be based on one or more biomarker values falling into a pre-defined range or is equal to a certain pre-defined value. In other embodiments, the adherence criteria can be a formula (s) which uses a biomarker datum or group of such data to determine if the resulting value falls into the pre-defined range or is equal to a certain pre-defined value.

For example, adherence criteria 224 can describe the parameters around the events 237 that the individual 12 needs to perform such as tests within a certain window, fasting for a given amount of time, sleeping for a given amount of time, exercise, low stress, not menstruating, etc. As such, adherence criteria 224 can establish the context of the information about to be provided. Adherence criteria 224 can also be used as mentioned above previously in another context to provide an assessment of whether the data is acceptable and when used in such a context may be referenced to as "acceptance" criteria. For example, before a sample is taken, the adherence criteria 224 can establish whether steps leading up to taking of the sample are accomplished. For example, the processor 102 in response to a request 240 displays the question, "Have you been fasting for the last 8 hours?", wherein a "Yes" response received by the processor via the user interface 146 meets the adherence criteria 224 for this step. In another example, after the sample is taken, the processor 102 can assess the received data for reasonableness using other adherence (acceptance) criteria. For example, based on prior data, a fasting bG sample should be between 120-180 mg/dl, but the received value was of 340 mg/dl, and thus fails such adherence (acceptance) criteria since being out of the predefined range for an acceptable value. In such an example, an adherence event 242 occurs wherein the processor 102 could prompt for an additional sample. In such a case, if the re-sampling fails too (i.e., not between 120-180 mg/dl), the assessment provided by the processor 102 is that the individual 12 has not fasted, and thus the processor 102 as instructed by the adherence criteria upon a failing of the re-sampling extend automatically the events 237 in the schedule of events 222 accordingly.

Next in step 212, the condition(s) and context(s) in which the schedule of events 222 is to be started and ended can be determined. This results in one or more entry criteria 226 and exit criteria 228 being provided for the schedule of events 222 as well as possibly for a group of other schedule of events to which the schedule of events 222 belongs if providing a package of structured collection procedures, e.g., procedures 70a, 70b, 70c, and 70d, which may run concurrently and/or sequentially one after the other.

For example, the entry criteria 226 can be used to determine whether the individual meets the conditions to use the collection procedure by the processor 102 checking that, for example, the individual 12 meets the entry criteria 226 based on current age being in a range, HbA1c being in a range, that the individual has a particular disease, has had the disease over a minimum period of time, has a Body Mass Index (BMI) in a range, had a Fasting Plasma Glucose (FPG) in a range, had a particular drug sensitivity, is taking a particular drug, taking a particular drug dosage, meets one or more prerequisites of another structured collection procedure, has completed one or more of another structured collection procedure, does not have one or more particular pre-conditions, e.g., pregnant, not fasting, or contraindications, e.g., feeling ill, feverish, vomiting, etc., and combinations thereof. Entry criteria 226 can also initiate the schedule of events 222 by an initiation event such as a time of day, a time of week, meal, taking a meal with a time offset, exercise, and exercise with a time offset, use of a therapeutic drug, use of a therapeutic drug with time offset, physiological circumstances, biomarker range, and biomarker within a predetermined range calculated as an offset from a prior biomarker value. Example of a physiological circumstance can be that entry criteria will be met to start a structured collection procedure when a pre-determined number of a physiological event, e.g., hyperglycemia, hypoglycemia, a certain temperature at a certain of day, and the like, occur within a pre-defined amount of time, e.g., hours, day, weeks, etc. Accordingly, the entry criteria can be used to support the use of need to met prerequisites, indications for usage, and/or contraindications for usage. For example, an entry criteria 226 could define a prerequisite condition which in order for the structured collection procedure 70 to run an Insulin Sensitivity optimization, the processor 102 must verify first that a structured collection procedure for a Basal titration is completed and/or has a desired result and/or as well as another structured collection procedure for an insulin to carbohydrate ratio is completed and/or has a desired result. In another example, an entry criteria 226 could be defined with needing to meet certain indications for usage in which certain structured collection procedures could provide segregated uses for diabetics who are Type 1 vs. Type 2 as well as types of structured collection procedures which can be used to titrate for specific drugs. In another example, the entry criteria 226 could be defined with needing to meet certain contraindications for usage, in which for example, certain structured collection procedures 70 will not run if the individual 12 is pregnant, sick, etc.

Examples of the exit criteria 228 can be based on the processor 102 determining that a particular value is reached, that a mean average of the primary samples values are in a range, that a particular event(s) and/or condition(s) have or have not occurred, and combinations thereof. Other conditions when the procedure may stop can include adverse events such as a hypoglycemic event, the individual is sick, the individual undergoes a therapy change, etc. Additional detail may also by provided by the processor 102 on the display 108 to the individual 12 based on what the specific exit criteria has been met. For example, in one example, if the individual 12 measures a glucose value indicating hypoglycemia, upon exiting the procedure, the processor 102 run automatically another alternative procedure which instructs the individual 12 to ingest carbohydrates and measure his blood glucose value every half an hour until the blood glucose exceeds 120 mg/dL. For this alternative procedure, the individual 12 can also be requested by the processor 102 to document his meals, activity, stress, and other relevant details to ensure that the conditions that led to hypoglycemia are recorded. The individual 12 may also be instructed by the processor 102 to contact the clinician 14 in this and other such special cases as deemed fit. Exit criteria can also include, for example, criteria for ending such as exiting after a successful completion, or exiting after an indeterminate completion, such as expiration of a predetermined timeout (logistical end), e.g., no result after n days, where n=1 to 365 days, or by termination e.g., exit with unsuccessful termination due to a fail-safe. It is to be appreciated that the structured collection procedure 70 can also be defined to end automatically not only based on meeting the exit criteria 228, but also when the individual 12 fails to perform a request to an acceptable level of compliance and/or when an individual's physiological state has changed such that the individual is should not carry out the schedule of events 222, thereby failing adherence criteria 224, wherein the adherence event 242 is to end the structured collection procedure.

In step 214, guidance 230 for the user during collection can be determined as well as any options 232 for customizing the collection. For example, for guidance 230, the clinician 14 can use a default list of messages, or tailor messages to guide the individual 12 during execution of the collection procedure 70. As an example, one message could be provided on a successful data acquisition (i.e., meets the adherence criteria 224) would read, "Thank you. Your next scheduled measurement is at 1230 pm." Alarms, such as provided by indicator 148, can also be associated with the collection procedure 70 that remind the individual 12 to take a measurement and can include a snooze functionality should the individual 12 need additional time to conduct the measurement. The snooze functionality as well as other device features are discussed further in later sections.

The result of steps 208-214 is the structured collection procedure 70 being created in step 216 which associates together the use case parameter 220, the scheduled of events 222, the adherence criteria 224, the entry criteria 226, the exit criteria 228, guidance 230, and the options 232. In one embodiment, at the time of generating a collection procedure 70 the clinician 14 also generates printed material that explains to the individual the following aspects (at a minimum): the purpose of the collection procedure 70 and expected ideal outcome, i.e., setting a goal for the collection procedure 70; the collection procedure 70 design and the number of measurements needed; the entry criteria 226 that the individual 12 must satisfy before initiating the collection procedure 70 and before taking each reading; and the exit criteria 228 under which the individual 12 should cease to continue the collection procedure 70. Such printed material as well as the guidance 230 that can be provided during the execution of the collection procedure 70 ensures that the individual is fully aware of why the data collection procedure is being carried out.

Examples, of the structured collection procedure 70 may be, for example, a structured collection procedure for determining an insulin-to-carbohydrate ratio, for determining bolus timing in respect to meal start, and for determining an exercise equivalent to ingested carbohydrates. In step 218, the structured collection procedure 70 is then made available for implementation and use in the system 41, such as in any of the above discussed manners mentioned with regards to FIGS. 1, 2, and 3. A structured collection procedure 70 accordingly may be provided via the above process, such as by either the medical community or healthcare companies 64, to help the clinician 14 address and/or investigate a defined medical use case or problem.

FIG. 5B shows the interactions of the parameters 222, 224, 226, and 228 of the structured collection procedure 70 for obtaining contextualized biomarker data from a diabetic patient to address a medical use case upon which the structured collection procedure is based. As mentioned above, the use case parameter 220 may be provided to identify the medical use case or question to which the parameters 222, 224, 226, and 228 address. For example, the processor 76 of the clinician computer 25, the processor 102 of the collection device 24, and/or the server 52 may read the medical use case parameters 220 from a plurality of structured collection procedures 70a, 70b, 70c, 70d (FIG. 2), such as provided on these devices and/or within the system 41, and provide a list of the available structured collection procedures, such as on the display 82 of the clinician computer 25 or the display 108 of the collection device 24. Additionally, the clinician computer 25, the personal computer 18, and/or the server 52 can use the medical use case parameter 220 for locating/sorting/filtering such structured collection procedures according to a medical use case(s).

As mentioned above, the entry criteria 226 establishes the requirements for initiating the structured collection procedure 70 to obtain data which includes biomarker data, particularly, collected in a predefined context. In one embodiment, the processor 102 of the collection device 24 can use the entry criteria 226 to determine when an associated structured collection procedure 70 is appropriate for the individual's physiological context and to ensure that all of the necessary inputs to the associated structured collection procedure have been established. Therefore, it is to be appreciated that the start date and/time of a structured collection procedure may dynamically change automatically by the processor 102 of the collection device 24 if the predefined condition(s) of the entry criteria 226 is not satisfied. Accordingly, until the entry criteria 226 is satisfied, the start date and/time of the associated structured collection procedure 70 can be at some unknown time in the future.

For example, in one embodiment, a structured collection procedure 70 can be chosen automatically by the processor 102 from a plurality of structured collection procedures 70a, 70b, 70c, 70d, such as provided in memory 110 of the collection device 24, memory of the computer 18, 25 and/or from server 52, based on satisfying the condition(s) of a defined entry criteria 226 for an associated structured collection procedure. For example, in one embodiment, a first structured collection procedure, such as procedure 70d, is useful for showing trends in blood glucose levels ("bG Level Trending"). Therefore, an entry criteria 226 for the first structured collection procedure 70d may be for the individual to have a bG level mean which has elevated over a defined period (e.g., a past number of days, weeks, and months from the current date) above a certain pre-defined rate. For a second structured collection procedure, such as procedure 70a, its entry criteria 226 may require a particular number of bG measurement for a pre-breakfast measurement over a defined period (e.g., a past number of days, weeks, months, from the current date) being below a pre-defined bG value. In such an example, the processor 102 upon start up in one embodiment when commanded, such as via input received via the user interface, in another embodiment, or at a scheduled time as programmed by the software 34 in another embodiment, can run through the various entry criteria 226 provided by the various structured collection procedures 70a and 70d that are, for example, provided in memory 110 of the collection device 24 and determine whether the stated condition(s) for the entry criteria 226 of a particular procedure 70 is satisfied. In this example, the processor 102 determines that the historical data from past measurements in memory 110 indicate that the individual's bG level mean has been elevating, and that the entry criteria 226 for the first collection procedure 70d has been met, but not the entry criteria for the second collection procedure 70a. In this example, the processor 102 then automatically selects and starts the first structured collection procedure 70d based on the above-mentioned analysis.

It is also to be appreciated that the use of the entry criteria 226 can help to reduce the misallocation of medical expenses by assuring that the indications of use for the structured collection procedure 70 have been met before starting the schedule of collection events 222. The entry criteria 226 as well can help assure that any requests to perform multiple structured collection procedures do not overlap if incompatible, are not unnecessary repeats of each other, or provide a significant burden on the individual. In this manner, many of the noted problems in which an individual may avoid any further attempts to diagnose their chronic disease or to optimize therapy can be both addressed and avoided automatically by the processor 102 of the collection device 24 via use of the entry criteria 226.

As shown by FIG. 5B, the entry criteria 226 can include context specific entry criteria 234, procedure specific entry criteria 236, and combination thereof. Examples of context specific entry criteria 234 can include one or more variables to identify meals, low blood glucose events, insulin type and dosage, stress, and the like. In another example, the context specific entry criteria 234 can be defined such as in the form of a specific question(s), to which the processor 102 requires a specific answer to be received from patient via input from the user interface 146. For example, the processor 102 in executing the entry criteria 226 may display on the display 108 the question of whether the individual is willing and able to perform the structured collection procedure 70 over the required period. If the individual responses affirmatively via the user interface 146, then the entry criteria 226 has been satisfied and the processor 102 continues automatically with performing the collection events 237 according to the their associated timing as defined in the structured collection procedure 70. If the individual responses in the negative to the displayed question, then the processor 102 will not continue with the structured collection procedure 70, and may for example, re-schedule the asking of such a question to a future time, such as if designated by an options parameter.

Examples of procedure specific entry criteria 236 can include one or more variables to identify disease state, disease status, selected therapy, parameter prerequisites, insulin to carbohydrate ratio prior to testing insulin sensitivity, incompatible collection procedures, and the like. The procedure specific entry criteria 236 can be defined such that the processor 102 will continue automatically with the structured collection procedure 70 with one of three initiators—the individual 12, the clinician 14, or data, e.g., if the condition(s) of the entry criteria 226 is satisfied. For example, the procedure specific entry criteria 236 can be satisfy if the clinician 14 has prescribed the structured collection procedure 70, such as via an authorized user entering via the user interface 146 a valid password to unlock the particular structured collection procedure for use, in one embodiment. In another embodiment, the clinician 14 can send the password or an authorization code from clinician computer 25 and/or server 52 to the collection device 24 which prescribes (authorizes) the collection procedure 70 for use by the individual 12 on the collection device 24. It is to be appreciated that one or more structured collection procedure 70 can be provided in memory 110 of the collection device 24 which cannot be used by the individual 12, and which can be also hidden from being viewed on the display 108, such as in a selection list, by the individual until authorized by the clinician 14.

The procedure specific entry criteria 236 can be satisfy by a user for example, by the user selecting a particular structured collection procedure 70 from a listing of structured collection procedures 70a, 70b, 70c, 70d provided on the display 108. An example of a data initiated procedure for criteria 236 would be that a biomarker measurement(s) provided to the processor 102 indicates a certain condition which must have occurred or be present in order for the entry criteria 226 for the particular structured collection procedure to be satisfied. Such a condition, for example, can be the occurrence of a single event, such as a severe hypoglycemic event, or a series of events, such as hypoglycemic events within a given, a predetermined time frame, such as in 24 hours from a start time, in one week from a start time, etc, a calendar date-time, and the like.

Accordingly, the entry criteria 226 can be a single criterion or multiple criteria that establish context and/or condition of the individual's physiology that are relevant to the medical use case being addressed by the structured collection procedure 70. In another embodiment, the entry criteria 226 can be assessed after data has been collected, such as, on historical data.

The schedule of events 222 specifies one or more events 237 which each comprises at least one or more variables defining a performance time 238, the guidance 230 to perform the event, requests 240 for patient actions, which may include a request for information from the individual and/or a request for collection of at least one type of biomarker data from the individual, and combinations thereof. For performance time 238, the schedule of events 222 can specify timing of each event 237, such as for a biomarker sampling at a particular time on three consecutive work days, or one sample at time of wake-up, one sample thirty minutes later, and another sample one hour later.

The guidance 230 for each event 237 and for any criteria 224, 226, 228 may include, for example, providing electronic reminders (acoustic, visual) to start, end and/or wake up at a particular time, to perform a bG collection at a particular time, to ingest a particular meal or food(s) at a particular time, to perform a certain exercise(s) at a particular time, take medication at a particular time, and the like. Guidance 230 may also include information, questions and requests to record particular information about physiology, health, sense of well-being, etc., at a particular time, suggestion to improve compliancy with the collection procedure, encouragement, and positive/negative feedback.

It is to be appreciated that the events 237 define all the steps that are necessary to be preformed in advance of as well as after a biomarker sampling according to a request 240, such that a reproducible set of circumstances, i.e., context before and/or after the sampling, is created in the biomarker data for the biomarker sampling. Examples of such biomarker data, in the context of diabetes, include fasting blood glucose values, pre-prandial glucose values, postprandial glucose values, and the like. Examples of a set of circumstances can include data associated with the biomarker value which identifies collected information in the data about meals, exercises, therapeutic administration, sleep, hydration, and the likes.

Each of the events 237 in the schedule of events 222 can be time-based, event-based, or both. An event 237 can also be a start of a meal, a wake-up time, start of exercise, a therapeutic administration time, a relative offset used with a prior glucose value, or a time indicating movement above or below a predetermined biomarker value threshold. The events 237 can also include any required patient actions necessary to be performed in advance of and during biomarker sampling such that reproducible circumstances are created at the time of biomarker sampling. This can includes one or more of meals, exercise, therapeutic administration, sleep, hydration, and the like. Additionally, the events 237 in the schedule of events 222 can be adjusted (number, types, timing, etc.), to accommodate work schedule, stressors, and the like of the individual 12.

As mentioned above previously, the adherence criteria 224 is used to assess qualitatively whether an event 237 performed according to the schedule of events 222 provided data which is acceptable to addressing the medical use case upon which the structured collection procedure 70 is based. In particularly, the adherence criteria 224 can provide variables and/or values used to validate data from a performed event 237. For example, an adherence criteria 224 can be a check performed by the processor 102 of the collection device 24 that a value collected in response to an event 237 is within a desired range, or is above, below, or at a desired value, wherein the value may be a time, a quantity, a type, and the like. The same or different adherence criteria 224 may be associated with each of the events 237 within the schedule of events 222 as well with the entry criteria 226 in one embodiment, and as being the exit criteria 228 in another embodiment, such as illustrated by FIG. 6D (i.e., "stop exercising when bG back in target range" which defines both the adherence and exit criteria). In one embodiment, one or more events 237 in the schedule of events 222 may be modified (e.g., added, deleted, delayed, etc.) if a particular event or events fail to met the adherence criteria 224 for the particular event or events. In one embodiment, the failure of the adherence criteria 224 can trigger an adherence event 242. In one embodiment, upon occurrence of an adherence event 242 due to the associated adherence criteria 224 for an event 237 not being met or satisfied, the processor 102 may be required one or more additional actions as a consequence. For example, the processor 102 may prompt on the display 108 additional information to the individual, and/or prompt a question to determine whether the individual 12 is sick, stressed, or unable to perform the request e.g., eat the meal, or exercise. If the individual answers "Yes", e.g., via the user interface 146, then as part of the adherence event 242 the processor 102 can provide a delay to the schedule of event (i.e. suspend). In one embodiment, the delay can continue until the individual indicated that he or she is better in response to another question prompter by the processor 102, such as the next day or after a predefined amount of time as also part of the adherence event. For example, the individual 12 is prompted by the processor 102 to administer a drug, but the individual is not at home, such as for example, where his/her insulin is located. The individual 12 can select the delay via the user interface 146, wherein the processor 102 re-prompts the individual after a predetermined amount of time. This delay may also have an upper limit in which if the schedule of events is not re-started within a certain amount of the time, the structured collection procedure 70 in such a circumstance may just end. In another embodiment, another form of an adherence event is a violation event, which results when the person executing a structured collection procedure 70 fails to make a recommended change in response to a request. For example, the request may be for the individual to adjust a drug dosage from 10 U to 12 U, wherein the individual answers in the negative to a question on the displayed on the display 108 asking if the individual will or has complied with such a change. In response to such a violation event, the processor 102 may also send a message and/or provide a delay as previously discussed above concerning the adherence event.

In another example and in one embodiment, a bG measurement must be collected before each meal in order for a structured collection procedure 70 to provide data that is useful in addressing the medical use case or question for which it was designed, such as identified by the use case parameter 220. If, in this example, the individual fails to take a bG measurement for the lunch meal in response to a request 240 for such a collection according to the schedule of the event 222, and hence the adherence criteria 224 for that event 237 fails to be satisfied, the processor 102 in response to the associated adherence event 242 can be programmed according to instructions in the collection procedure 70 to cancel all remaining events 237 in the schedule of events 222 for that day, mark the morning bG measurement stored in the data file (such as data file 145 (FIG. 4) as invalid, and reschedule for the schedule of event 222 for the next day. Other examples of further actions in which the processor 102 may take in response to an adherence event 242 may be to dynamically change the structured collection procedure by switch to a secondary schedule of event, which may be easier for the individual to perform, provide additional events for measurements to make up the missing data, change the exit criteria from a primary to a secondary exit criterion providing modified criterion(s), change the adherence criteria from a primary to a secondary adherence criterion, fill in the missing data for the failing event with (an estimate from) historical data, perform a particular calculation to see if the structured collection procedure 70 can still be successfully performed, send a message to a particular person, such as a clinician, of the failing event, provide a certain indication in the associated data record 152 to either ignore or estimate the missing data point, and the likes. In still another embodiments, the adherence criteria 224 can be dynamically assessed, such as for example, based on one or more biomarker values and/or input received from the user interface in response to one or more questions, via an algorithm which determines whether the collected data provides a value which is useful in addressing the medical use case or case. In this example, if the calculated adherence value is not useful, for example, does not fall into a desired range or meet a certain pre-define value, then further processing as defined by the resulting adherence event would then take place, such as any one or more of the processes discussed above.

The exit criteria 228 as mentioned previously above establishes the requirements for exiting or completing the structured collection procedure 70, so that the structured collection procedure 70 has adequate contextual data to answer the medical question addressed by the structured collection procedure 70. The exit criteria 228 can help increase the efficiency of the structured collection procedure 70 by minimizing the number of required samples needed to address the medical use case. By "addressing", it is meant that sufficient data has been collected in which the clinician 14 may render an assessment to the medical use case. In other embodiments, the assessment may be indicated by a given confidence interval. A confidence interval is a group of discrete or continuous values that is statistically assigned to the parameter. The confidence interval typically includes the true value of the parameter at a predetermined portion of the time.

As with the entry criteria 226, the exit criteria 228 can comprise one or more of context specific exit criteria 244, procedure specific exit criteria 246, and combinations thereof. Examples of context specific exit criteria 244 can include one or more variables to identify mood, desired blood glucose events (i.e., blood glucose level), to indicate stress, illness, contraindications, such as for example, hyperglycemia, hypoglycemia, vomiting, a fever, and the likes. Examples of procedure specific exit criteria 246 can include one or more variables to identify a number of events meeting the adherence criteria, biomarker values being in a desired pre-determined range and/or at a desired pre-determined value, a desired disease state, desired disease status, no change in the biomarker after a pre-determined period, or no significant progress over a pre-determined period to a desired biomarker value, and the like. It is to be appreciated that in one embodiment the exit criteria 228 can establish the condition(s) needed to be met for entry criteria 226 of a second structured collection procedure 70. For example, upon having a suitable Insulin-to-Carbohydrate (I:C) determined with a first collection procedure, such as for example, structured collection procedure 70b (FIG. 6B), running a structured test for determining the best time for administering a bolus in regards to a start of a meal, such as for example, procedure 70c (FIG. 6C), which needs a current I:C ratio, can be conditioned such that the processor 102 can implement automatically a schedule of events of the second structured collection procedure 70c upon meeting the exit criteria of the first structured collection procedure 70b at some unknown time. In other embodiment, for example, the exit criteria 228 of a first structured collection procedure 70 that is being run by the processor 102 according to the schedule of events 222 and the entry criteria 226 of the second structured collection procedure 70 both can be based on the same one or more contraindications, such as mentioned above. In such an embodiment, upon occurrence of a contraindication being provided to and/or detected by the processor 102, such as via the user interface 146 and/or the biosensor 140, respectively, which in this example meets the exit criteria 228 of the first structured collection procedure 70, the processor 102 would automatically start the schedule of events of the second structured collection procedure 70 as the entry criteria 226 of the second structured collection procedure 70 has also been met. An example of such a second structured collection procedure 70 which can be started via exiting a first structured collection procedure can be one which has a schedule of events 222 which requests a biomarker samplings at a routine interval, e.g., every 30 minutes, every hour, every day at a particular time, etc., until the contraindication(s) clears (e.g., biomarker value(s) reaches a desire range or value, individual 12 indicates to processor 102 via user interface 146 no longer having a contraindication(s), expiration of a predefined period, etc.). Such an embodiment is useful if recording the context and values of the events after the occurrence of the contraindication(s) is a desire and in which the first collection procedure should be exited when a contraindication(s) occurs.

The exit criteria 228 can be a single criterion or multiple criteria that establish the conditions to exit the structured collection procedure 70. The conditions are provided in a preferred embodiment such to ensure that adequate contextualized biomarker data has been obtained to answer the medical question being addressed by the collection method. For example, such that a predetermined number of valid samples have been acquired, or that the variability in the samples is below a predetermined threshold. Therefore, it is to be appreciated that the end date and/or time of the collection procedure 70 may be dynamic and be changed automatically by the processor 102 if the predefined condition(s) of the exit criteria 228 is not satisfied. Likewise, the conditions of the exit criteria 228 may be dynamic and be changed automatically be the processor 102 such for example if a particular adherence criteria 224 is satisfied or not satisfied. For example, in one embodiment if adherence criteria 224 for a particular collection event 237 is met, then the processor 102 is instructed to use a first exit criterion and if not met, then the processor 102 is instructed to use a second exit criterion that is different from the first exit criterion. Accordingly, until the exit criteria 228 is satisfied, the end date and/time of the structured collection procedure 70 can be at some unknown time in the future. In another embodiment, the exit criteria 228 can be assessed after data has been collected, such as, on historical data.

It is to be appreciated that the entry and exit criteria 226, 228 together with the adherence criteria 224 can help to reduce both the time to perform the structured collection procedure 70 and the expense associated with the collection by defining one or more of the acceptable conditions, values, structure and context needed to perform the schedule of events 222 in an effort to make every collection event 237 count and/or reduce consumption of test strips 30 with unneeded collections that do not help address the medical use case or question. Hereafter reference is made to FIGS. 6A-6E.

Structured Collection Procedure Examples

FIGS. 6A-E illustrate examples of some structured collection procedures 70a, 70b, 70c, and 70d depicting their functions which can easily be translated by one of ordinary skill in the related art into instruction code which may be implemented on any one of the devices the above described devices 18, 24, 25, 26, 28, 36, 52. Therefore, for brevity, no discussion is provided in regard to pseudo-code or actual code relating to these illustrated functions.

Figure 6A:
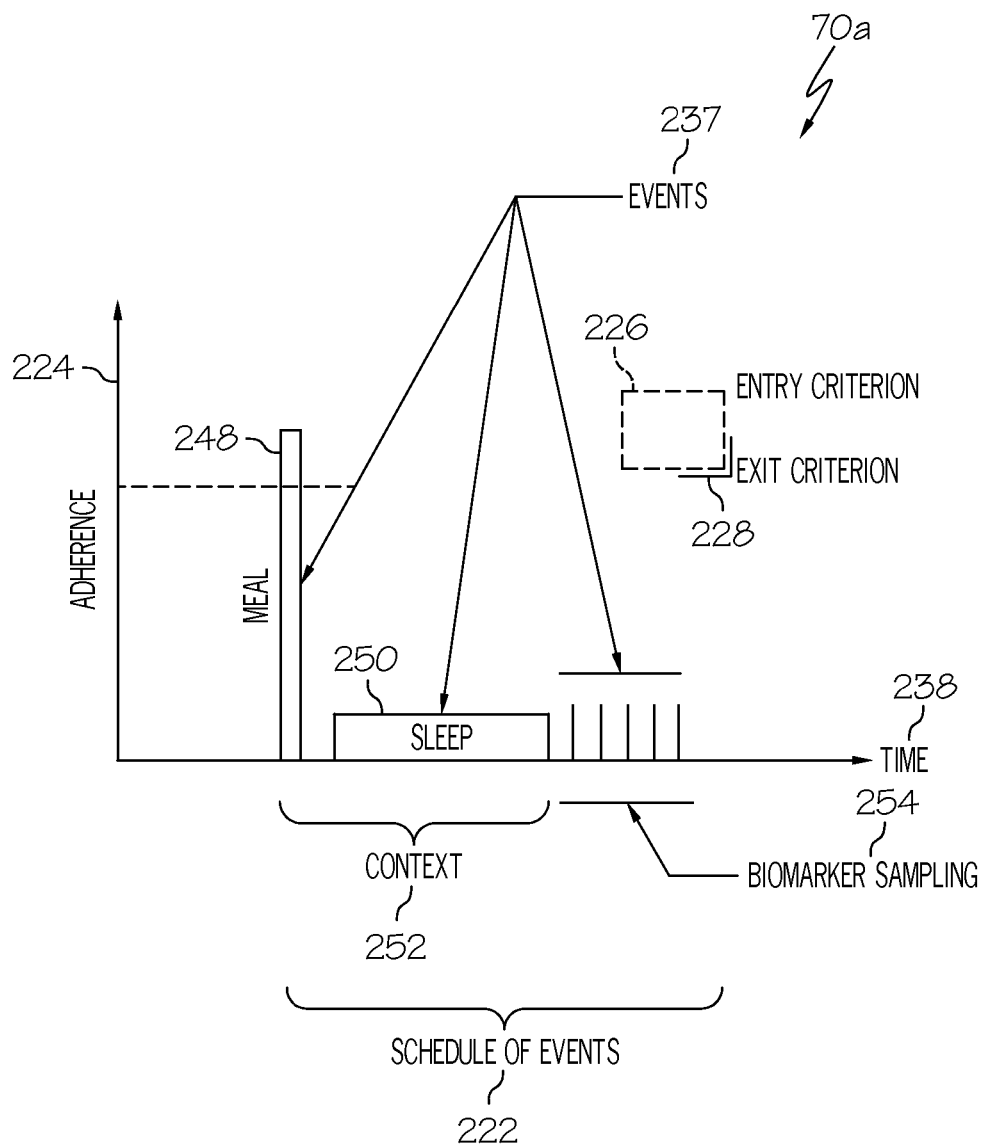
FIGS. 6A, 6B, 6C, 6D, and 6E show various structured collection procedures embodiments defined according to the present invention.

FIG. 6A diagrammatically illustrates an embodiment of a structured collection procedure 70a used to obtain contextualized biomarker data from a diabetic patient. The horizontal axis shows the performance times 238 of the various events 237, and the vertical axis shows adherence criteria 224 without values. In the illustrated embodiment, the events 237 can include recording information regarding a meal 248 and sleep 250 in which to provide context 252 for the five-biomarker samplings 254 also events 237 that are part of the schedule of events 222. In this example, the adherence criteria 224 for the meal 248 can be a value which must be greater than a minimum value, e.g., for a carbohydrate amount. The entry criteria 226, for example, can comprise a biomarker value being above a particular value such as required to meet contextualization requirements to begin the structured collection procedure 70a. The exit criteria 228 as well can comprise a biomarker values being below a particular value such as also required to meet contextualization requirements to end the structured collection procedure 70a. Such a structured collection procedure 70 is useful for helping to address a number of medical use cases.

Figure 6B:
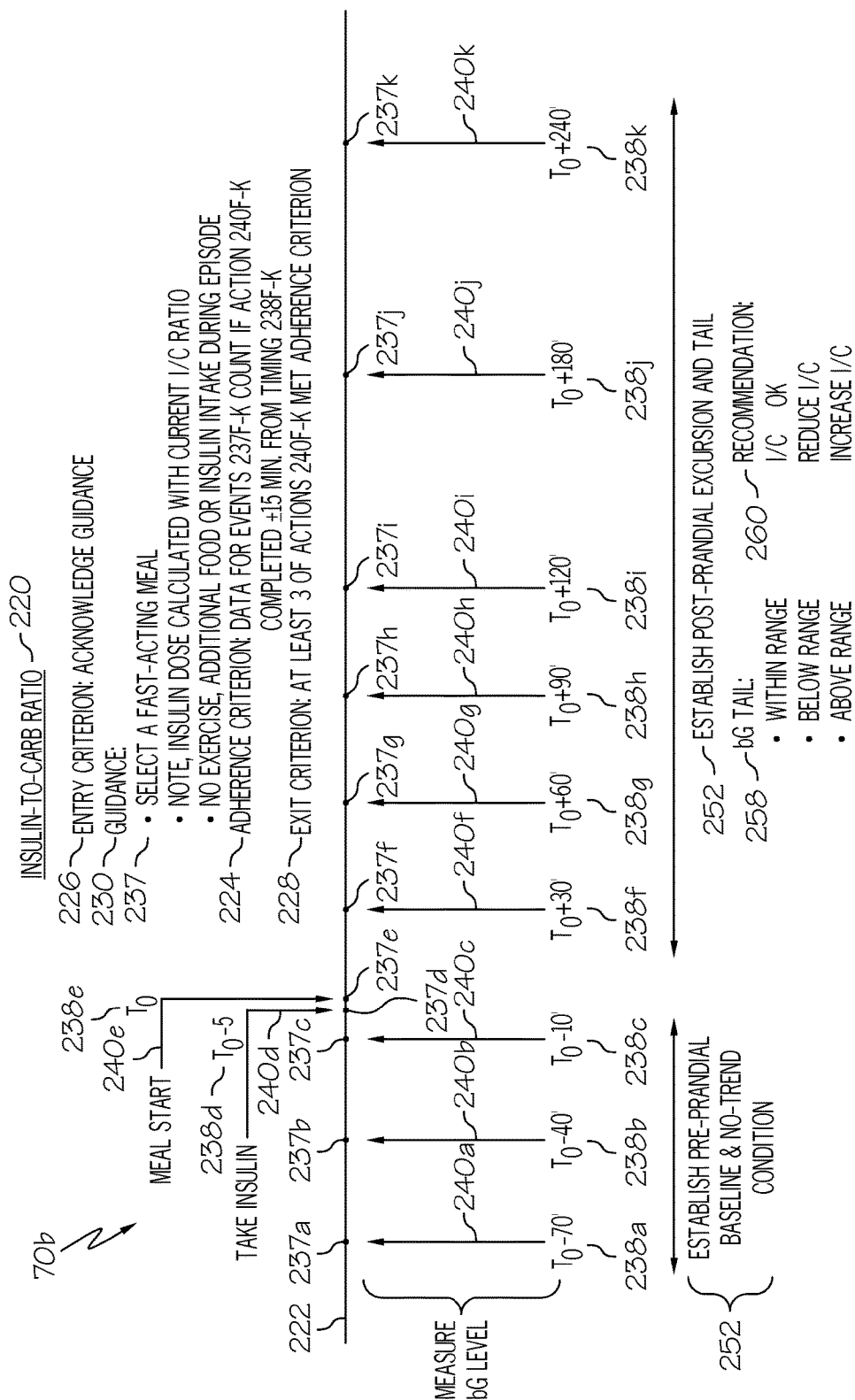

Another example is diagrammatically depicted by FIG. 6B which shows a structured collection procedure 70b which has a defined medical use case parameter 220 indicating that the procedure can be helpful for determining suitability of an insulin to carbohydrate (I:C) ratio. As illustrated, the entry criteria 226 is defined as having the individual simply acknowledge guidance 230 of selecting a fast-acting meal, to note that the insulin dose is calculated with the current I:C ratio as well as agreeing not to exercise, take additional food or insulin during the testing period. For example, the processor 102 can present on the display 108 such guidance 230, which the user can then acknowledge after reading with either a "Yes" or a "No" entered via using the user interface 146 for the desired entry choice. If the user enters "Yes", then the entry criteria 226 is satisfied, and the processor 102 automatically starts the schedule of events 222 defined in the structured collection procedure 70b. In another embodiment, the entry criteria 226 may be or include satisfying a request 237 for selecting a fast-acting meal. For example, the request 237 for selection can be the processor 102 displaying on the display 108 a selection menu providing a listing of fast-acting meals to which input of such a selection via the user interface 146 is needed. For example, selection of a fast-acting meal may be made via a press of one of the buttons 147, 149 or via the touch screen interface if provided by display 108. Such a selection can then be stored in memory 110 of the collection device 24 such as setup data 163 (FIG. 4) which may be part of the data file 145 (FIG. 4) for the structured collection procedure 70*b*. In an alternative embodiment, a particular fast-acting meal may be recommended by the structured collection procedure 70*b*.

As shown, the schedule of events 222 can comprise one or more events, such as the plurality of events 237*a-k* illustrated and with each having associated performance times 238*a-k* and requests for action 240*a-k*. As shown, the requests for action 240*a-c*, and 240*f-k* are requests for the user to take a bG level measurement, request 240*d* is to take an insulin dose, and request 240*e* is to eat the fast acting meal. Also shown is that events 238*f-k* each have an adherence criteria 224, which must be met if the data for events 238*f-k* are to be recorded in the data file 145. In this example, the adherence criteria 224 requires that the actions 240*f-k* be completed within ∀20 minutes of their corresponding performance times 238*f-k* in order for a data record 152 recording the received value(s) for the corresponding event 237*f-k* to count towards completing the collection procedure 70*b*. In one embodiment, the processor 102 will make each of the requests 240*a-k* at their associated performance times 238*a-k* in order to obtain resulting data values e.g., data values 256*a-k* (FIG. 4) at the time the requests are performed.

For example, the processor 102 can prompt the individual 12 with a request 240*a* to take a bG level (biomarker) measurement at performance time 238*a*. The resulting measurement when received by the processor 102, such as automatically from the measurement engine 138 after reading the test strip (biosensor) 140 for the desired biomarker, is then recorded automatically by the processor 102 in the date file 145 as a corresponding data value 256*a* for the associated event 237*a*. For actions 240*d* and 240*e*, at a required time, the processor 102 can automatically prompt the individual 12 to take the prescribed action at the required time, and again automatically prompt the individual thereafter to confirm that the required action has been taken, or that a predefine status has been achieved. A date-time stamp 169 can also be provided in the date record 152 automatically by the processor 102 upon triggering of the requests 240*a-k*, acknowledgement of the requests 240*a-k*, upon completion of the event 237*a-k*, upon receiving a data value 256*a-k* for the event 237*a-k*, and combinations thereof. Additionally, in another embodiment, the individual 12 can record data values 256*a-k* for one or more events 237*a-k* by entering the data directly into the device 24 via the user interface 146, wherein the processor 102 stored the entered data values/information in the associated data record 152 for the event 237*a-k*, or in other embodiments can record a voice message with the information for later transcription into digital data. In still other embodiments, the individual 12 can be guided by the collection device 24 to record data for an event 237*a-k* using a paper tool 38.

As mentioned previously above, each event 237 can be a recording of a biomarker value, or a request for a required patient action that is necessary in order to create a context for the biomarker value, such as for example, meals, exercise, therapeutic administration, and the like. In the illustrated embodiment, the context 252 for completing events 237*a-c* is to establish a pre-prandial baseline and a no-trend condition, and for events 237*f-k* to establish a post-prandial excursion and tail. Such context 252 for these events may also be associated with the corresponding data records 152 for each event as contextual information 156 (FIG. 4). Such information is useful later when reconstructing the data and/or when there is a desire to know the context for which the data record was created.

It is to be appreciated that any patient action taken outside of the required requests for patient actions 240*a-k* can also be recorded by the processor 102 but will not be considered by the processor 102 as part of the collection procedure 70*b*. Data 256*a-k* for events 237*a-k* that are prospective can be identified based on a type of event, the time of the event, the trigger of the event, and combination thereof. Each of the performance times 238*a-k* can be fixed or variable based on prior data. Some of the event 237*a-k* in other embodiments can also be a past, current, or a future event such as for meals, exercise, and the like, or data values such as for hypoglycemic events, hyperglycemic events, or data of a specific value of interest. In some embodiments, the events 237*a-k* can be identified via a paper tool 38 that is procedure based.

As also shown, the structured collection procedure 70*b* will end if the condition of the exit criteria 228 is satisfied. In this example, the exit criteria 228 is satisfied if at least three of the actions 240*f-k* met the adherence criteria 224. For example, the processor 102 may provide a unique identifier (e.g. an incremental count) 167 (FIG. 4) in the data file 145 for each event 237*a-k* performed and to which satisfied the adherence criteria 224 if required. In the illustrated embodiment of FIG. 4, events 237*a-c* and 237*e-k* each receive a unique identifier but not event 237*d*, e.g., <null>, since not satisfying an associated adherence criteria (not shown). In addition, analysis logic 258 and resulting recommendations 260 can also be provided in the structured collection procedure 70*b* which the processor 102 may apply automatically to the data collected upon satisfying the exit criteria 228 in one embodiment.

Figure 6C:
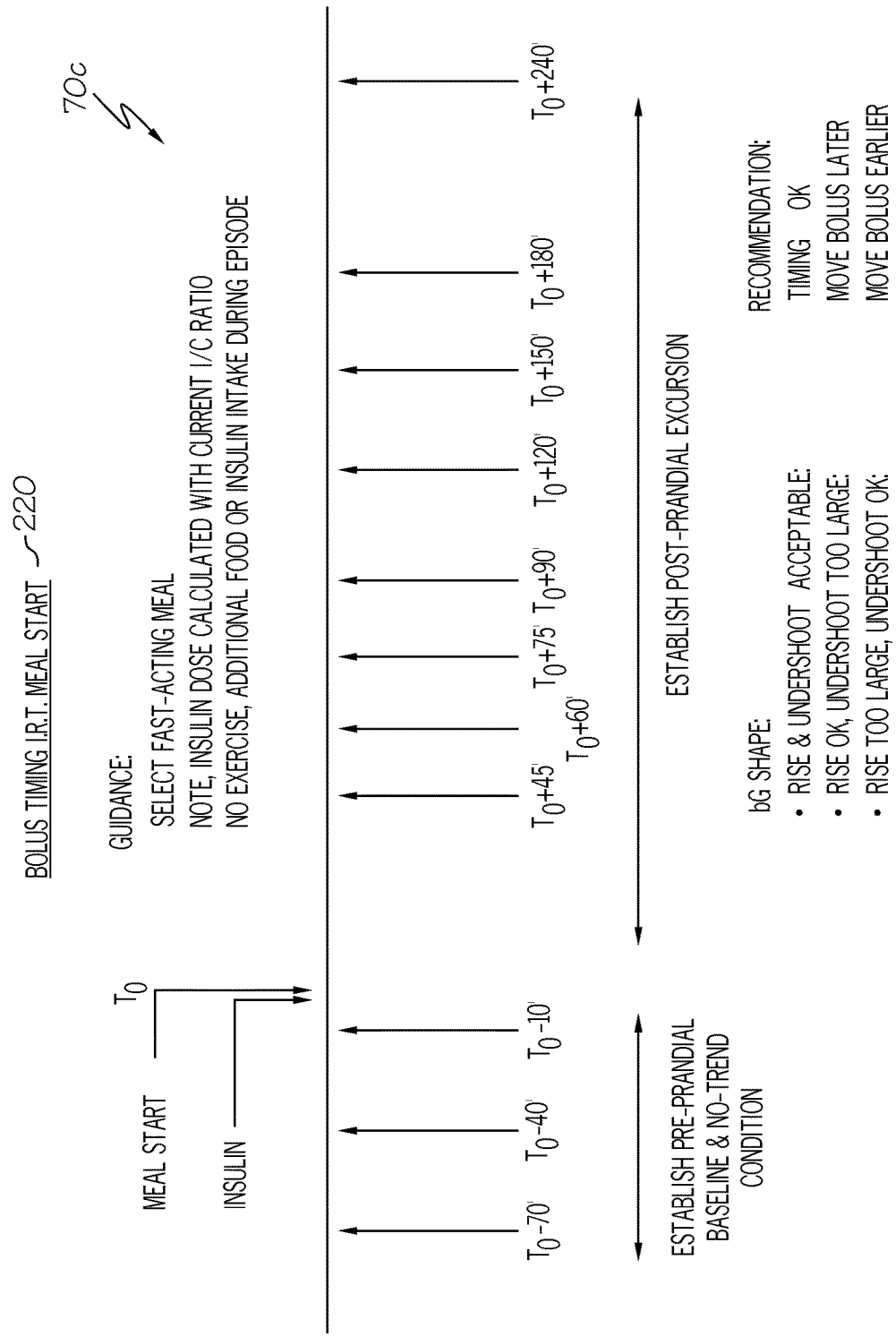
Figure 6D:
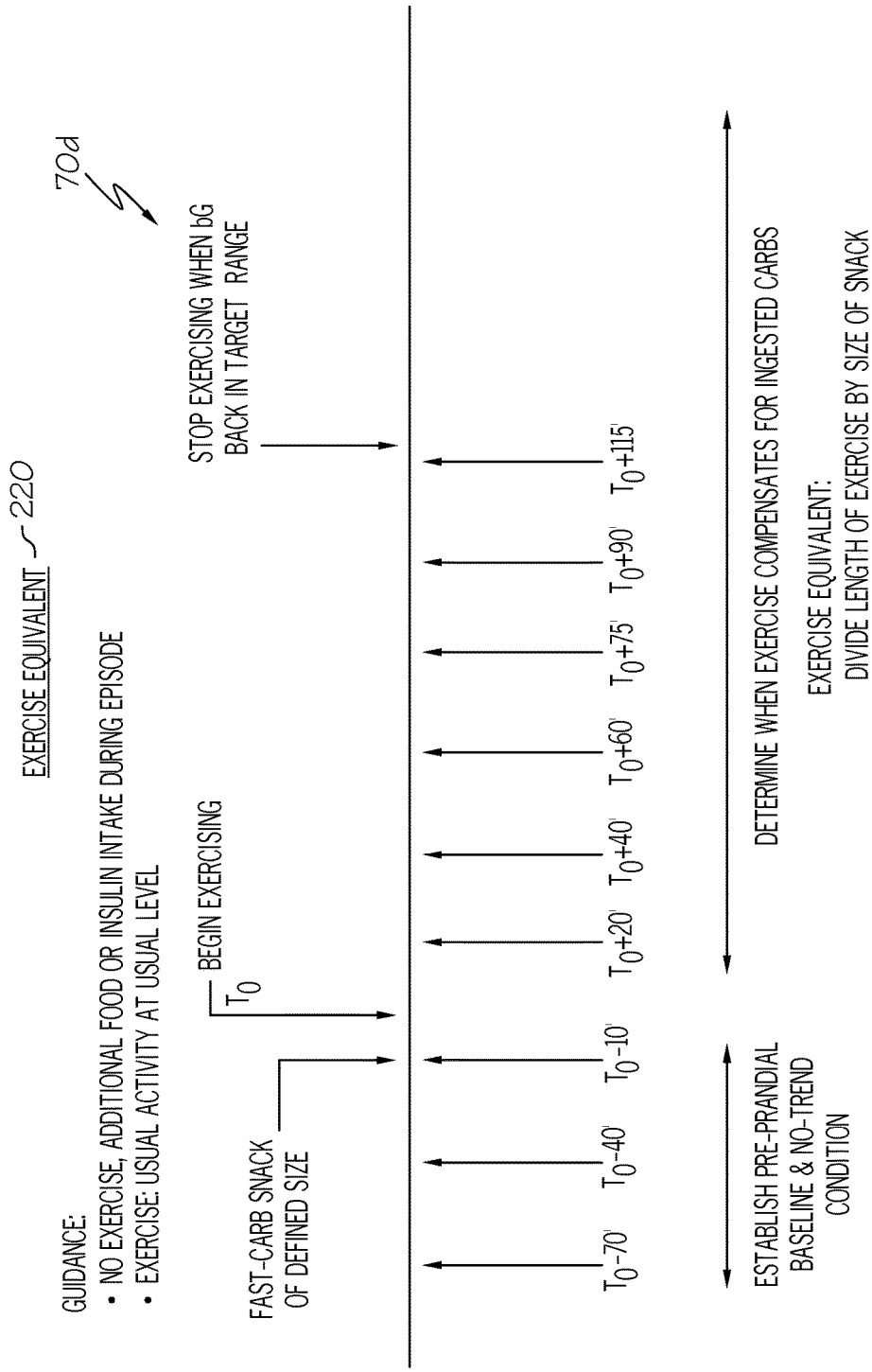

Similar features are also provided in the examples illustrated by FIGS. 6C and 6D, wherein FIG. 6C depicts a structured collection procedure 70*c* which has a defined medical use case parameter 220 indicating that the procedure is helpful for determining suitability of a bolus in regards to a meal start. Likewise, FIG. 6D depicts a structured collection procedure 70*d* which has a defined medical use case parameter 220 indicating that the procedure is helpful for determining suitability of an exercise equivalent to a carbohydrate intake. In addition to the above examples, other such structured collection procedures may be designed to address other various medical use cases such as, for example, the following: determining the effects of eating a particular food on a biomarker level of an individual; determining the best time to take medication before and/or after a meal; and determining the affect of a particular drug on a biomarker level of an individual. Still other structured collection procedures can be provided which may be useful in addressing questions concerning how best to initialize therapy for an individual, finding a determination of status of an individual's disease progression, finding the best ways to optimize an individual's therapy, and the like. For example, the clinician 14 can define and/or use a pre-defined structured collection procedure 70 which looks at factors which may have an effect on the therapy of the individual. Such factors can include, for example, stress, menstrual cycle, pre-dawn effect, background insulin, exercise, bolus timing with respect to a meal, basal rate, insulin sensitivity, post-prandial behavior, and the like.

Figure 6E:
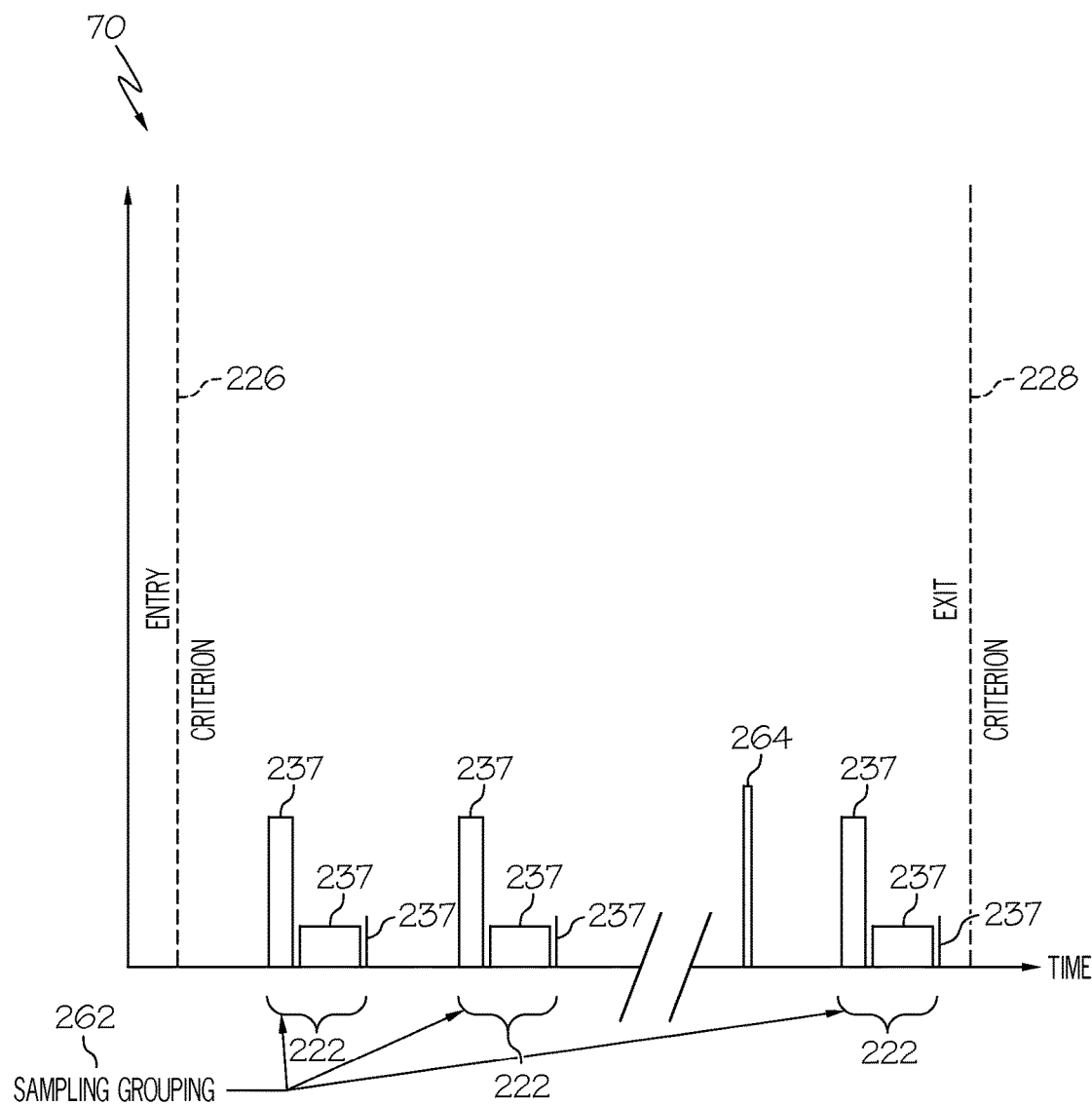

FIG. 6E shows a diagram structured collection procedure 70 comprising one or more multiple sampling groupings 262 each comprising a recurring schedule of events 222 provided between the entry criteria 226 and the exit criteria 228. In this example, the schedule of events 222 comprises one or more events 237 occurring each day at consistent times of day. As the structured collection procedure 70 in the process of obtaining contextualized biomarker data from a diabetic individual 12 can span over multiple days, even week and/or months before the exit criteria 228 is met, one or more checks 264, such as for parameter adjustment, and/or evaluation of whether to re-run the sampling groupings 262, can also be provided between the entry and exit criteria 226, 228 in one embodiment. The duration between such checks 264 can be used for physiological system equilibration, evaluation of treatment efficacy, or convenience. For example, either between each sample grouping 262 or after a pre-defined number such sampling grouping 262 (as shown), an analysis for the check 264 can be performed by the processor 102 to determine whether an adjustment to any parameter in the collection procedure 70 is needed.

For example, such analysis may be either for a parameter optimization or efficacy assessment. For the parameter optimization, the processor 102 can run calculations on the samples provided within a previous schedule of events 222 or sample grouping 262, using information from prior optimizations, clinician set parameters, and a collection or therapy strategy, recommends a new parameter value. For the efficacy assessment, the processor 102 can evaluate data not utilized by the optimization analysis. Additionally, it is to be appreciated that after a group of samples, i.e., sampling group 262, are taken the processor 102 can also evaluate the data from the sampling group 262, such as if such data is need in order to alter/optimize a person's therapy. Adherence criteria 224 can be applied to the perform this evaluation to the data of the sampling group 262. For example, a first adherence criteria 224 can be used by the processor 102 to assess whether a minimum amount of data is provided by the sampling group 262 and if not, for example, the alteration/optimization of the individual's therapy will not take place. Another adherence criteria 224 could permit the processor 102 assess whether the data is acceptable to permit an adjustment called for by the check 264, such as looking at spread of the data, whether these is too much variability (noise), as well as other data attributes to use the data. In this example, if meeting such adherence criteria, then processor 102 has assessed that there is minimum risk that adjusting a parameter of the procedure could readily result in a severe event, e.g., hyper- or hypoglycemic event. Lastly, an adherence criteria can be used by the processor to assess the exit criteria 228 based on the data of sampling group, for example, the exit criterion is met when the data from the sampling group 262 satisfies the adherence criteria, such as for example, discussed above, for the sampling group.

It is to be appreciated that collection or therapy strategies can be categorized into scale based (sliding or fixed) assessments or formula based assessments. As input to the collection or therapy strategy, the processor 102 in one embodiment can utilize the data collected from a predetermined number of prior sample grouping(s) 262. This data can be either used as individual points (only the formula based collection or therapy strategies), or combined with filtering for use in a scale based assessment. In another embodiment, for example, the result of a check 264 performed by the processor 102 can also result in a status or recommendation being provided by the processor 102 automatically. Such status or recommendation may be e.g., a status of continuing with current parameter values, a recommendation to change particular parameters, a recommendation to change the adherence and/or exit criteria, a status that the processor 102 switched to a secondary adherence and/or exit criteria based on the analysis performed on the data from a prior schedule of events or prior sample grouping, or a recommendation to terminate the collection procedure, and the likes.

Customizing a Structured Collection Procedure

FIG. 7 conceptually illustrates one example of a pre-defined structured collection procedure 70, which has a defined medical use case parameter 220 indicating that the procedure is helpful for medical use cases or questions which need to know the trends in blood glucose (bG) levels of an individual and/or the relationships between blood glucose values and time of day, meal size, and energy level. As mentioned above previously, the use case parameter 220 can be used as an identity tag in which the processor 102 may locate the associated structured collection procedure 70 in response to a search query, such as, for entered use case or question. For example, the search query can be entered into the collection device 24 via the user interface 146 and/or received from the clinician computer 25. Such a search query may result from a desire to know which uses case can be addressed by the structured collection procedures 70 currently available on the collection device 24, or to know which structured collection procedure 70 would be useful to address a particular use case or question. Therefore, the use case parameter 220 in one embodiment permits a structured collection procedure 70 to be automatically chosen by the processor 102 from a plurality of structured collection procedures 70a-d, such as provided in memory 110, memory 78, computer readable medium 40, and/or server 52 based on a selection, such as from a displayed list on the display 108 provided by the processor 102, or from input received by the processor 102 from the user interface of a defined medical question. In other embodiments, the use case parameter 220 may also indicate the structured collection procedure 70 is also useful for showing relationships between bG level values and time of day, meal size, and/or energy level.

In one embodiment, the pre-defined parameters of the structured collection procedure 70 can be displayed for modification/customization by the processor 102 of the collection device 24 on the display 108 and/or by the processor 76 of the clinician computer 25 on the display 82 by an authorized user. Such an authorized user may be identified, for example, on the collection device 24 and/or the clinician computer 25 by a password entered via the user interface 146, 86, respectively. In such an embodiment, the pre-define parameters of structured collection procedure 70 can be displayed on the display 108, 82 in which customizable parameters can provide editable or selectable variables via drop-down boxes with various selection choices, radio buttons, check boxes, formatted fields requesting a specific type of information (mm-dd-yyyy, number, letter, etc.), text boxes to enter messages to be displayed, and the likes. The structured collection procedure 70 can be displayed for editing in tabular format (as illustrated) in one embodiment or in a sequential manner listing one parameter at a time in a scroll-through fashion in another embodiment. In still another embodiment, structured collection procedures can be provided which cannot be modified.

As shown by FIG. 7, the structured collection procedure 70 may further comprise parameters defining one or more criteria setting the conditions needing to be met by the individual 12 to start of the structured collection procedure, i.e., entry criteria 226, to end the structured collection procedure i.e., exit criteria 228, and combinations thereof. In one embodiment, the processor 102 of the collection device 24 uses the one or more criteria to automatically start, evaluate, and end the structured collection procedure 70 if the condition(s) defined by the structured collection procedure are met. In still another embodiment, adherence criteria 224, which are the conditions needing to be met in order for the collected datum/data to be accepted, can also be provided in the structured collection procedure 70.

As also shown in FIG. 7, the structured collection procedure 70 further comprise parameters defining one or more (collection) events 237 which together form the schedule of events 222. Each of the events 237 comprises one or more requests 240, e.g., for a measurement from the measurement engine 138 of a biomarker value for a sample provided to the biosensor 140, and/or for information to be entered by the individual via the user interface 146 such as in response to a question presented by the processor 102 on the display 108. In the illustrated embodiment, the requests 240 are for a bG measurement, a meal size indication (S, M, or L), and an energy level indication (1, 2, 3, 4, 5), in which 1 is lowest and 5 is highest. Other such requests 240 can include indicating whether the individual exercised, indicating a particular food that was consumed, indicating which medicine was administered, indicating dosage of the medicine administered, and the like may also be provided in other structured collection procedures 70. In the illustrated embodiment, the collection events can be customized by selecting which request 240 the processor 102 should perform via a yes/no selection box.

The structured collection procedure 70 may also include guidance 230 and timing or performance time 238 associated with each of the collection events 237 as well as with each of the entry, exit, and adherence criteria 226, 228, and 224. Such guidance 230 is provided by the processor 102 to the display 108 upon the occurrence of the associated collection event 237 or other parameters. For example, a collection event 237 for a bG measurement before breakfast may also have a request 240 for an indication of the energy level of the individual. Therefore, in this example, the associated guidance 230 which states, "Please indicate energy level" is provided on the display 108 by the processor 102. It is to be appreciated that the guidance 230 is a text box, field, area, which enables for information to be provided to the individual to help the individual in performance of the structured collection procedure 70. In this example, selection of a number from 1 to 5 may be made via press of one of the buttons 147, 149 or via the touch screen interface if provided by display 108 as a data entry for such a request 237, which is then stored by the processor 102 in memory 110 of the collection device 24 as part of a data file 145 (FIG. 4) for the structured collection procedure 70.

The timing parameter 238 of the structured collection procedure 70 is used to specify for any one of the associated collection event 237, the entry, exit, and adherence criteria 226, 228, 224, either a specific date and/or time (mm-dd-yyyy, hh:mm), or a period (n) after a preceding collection event in which to perform the associated collection event. The periods $n_1$, $n_2$, $n_3$ in the illustrated embodiment for the respective collection events 237 indicate hours, but in other embodiments can be indicated in minutes or seconds. In another embodiment, the timing or performance time parameter 238 for an associated collection event 237 and for the entry, exit, and adherence criteria 226, 228, 224 can be modified by another collection event and/or by the criteria.

For example, in the illustrate embodiment, the entry criteria 226 is modified by the adherence criteria 224 by adding a day if the guidance 230 provided in the form of a question "Are you willing to conduct a test over 3 consecutive days?" is not affirmed by the individual 12 e.g., via a "No" selection provided on the collection device 24. In this illustrated example, the "Affirms guidance" may be a drop down selection provided in a combo box for customizing the adherence criteria 224 of the associated collection event 237, which when selected causes the processor 102 to wait for the accepted/not accepted input (e.g., via buttons 147, 149) before executing the remaining logic ("if not add 1 day to timing") of the adherence criteria 224. Still further in this example, the processor 102 in accordance with the logic provided in the adherence criteria 224 associated with the exit criteria 228, can set the timing or performance time parameter 238 of the exit criteria 228 to the date (mm-dd-yyyy) that is 3 days after completing the entry criteria 226. It is to be appreciated that the various possible combinations of logic statements which may be performed by the structured collection procedure 70 can be pre-defined and selected by a drop down box in order to be customized in one embodiment, and/or logic statements can be built in another embodiment.

The structured collection procedure 70 can also includes an options parameter 232 associated with each of the collection events 237 as well as with each of the entry, exit, and adherence criteria 226, 228, 224. The options parameter 232 can have a customizable value(s) to govern whether the data and/or results of the associated collection event 237 or any of the other parameters e.g., entry, exit, and adherence criteria 226, 228, 224, in the structured collection procedure 70 meets a particular condition such that still further processing may be carried out by the processor 102 if such a condition(s) is meet. For example, such options can be to have the processor 102 automatically send a message to the physician indicating that the individual has started the structured collection procedure 70 via satisfying the entry criteria 226, or to provide a message to the individual and/or the physician if the individual fails a collection event 237 by not satisfying an adherence criteria, or to provide a message to the physician when the individual completes the structured collection procedure 70 when the exit criteria 228 is satisfied, or combinations thereof. For example, such an options parameter 232 can have a global list of such actions which is selected on the display 108, for example, by a selected value from a range of values associated with each option. For example, the options for each parameter can be customized via selecting from a drop down box having option choices (e.g., 1, 2, 3, 4, 5, . . . , A, B, C, etc.) and in which, for example, Option 1 of having the processor 102 provide a message to the physician if the individual fails a collection event 237 (e.g., by not satisfying an adherence criteria), is shown selected for the before breakfast collection event 237. An example in the context of individual 12 being diabetic is provided hereafter to illustrate further such features provided on a collection device 24 according to the present invention.

A typical patient with Type 2 diabetes may measure his/her blood glucose once per day after waking up in the morning. At a routine office visit, the individual's HbA1C result is found to be elevated. The physician recommends that the person goes through three days of intensified glucose monitoring, and selects the structured collection procedure which is useful for this purpose. The structured collection procedure 70 is then customized as discussed above such that during these three days collection events 237 are defined with a number bG measurement requests 240 such that the individual can be requested by the processor 102 to measure his/her blood glucose before and two hours (e.g., $n_1=2$) after breakfast, before and two hours ($n_2=2$) after lunch, before and two hours ($n_3=2$) after supper, and at bedtime. Additionally, the individual 12 can be requested via other associated requests 240 for each collection event 237 to provide an assessment of the relative size of the ingested meals at the appropriate times as well as an indication how he/she feels with regard to energy level. In the illustrate embodiment of FIG. 7B, the processor 102 can request the indication of energy level with each collection event 237 and the assessment of the relative size of the ingested meals every other collection event 237 (i.e., after the meal). Furthermore, the physician has provided a condition via adherence criteria 224 of having to perform the meal assessment within ±30 minutes of period (n) of the associated collection event 237 in order for such information to be useful in the assessment. Such information is useful to contextualize the collected data and for the analysis performed on the collected data.

Additionally, the physician would like to be notified when the individual has failed to complete the "before breakfast" collection event 237. Therefore, to facilitate the notification option, the physician customizes the structured collection procedure 70 by set the options parameter 232 associated with the "before breakfast" collection event, via a drop down box to "Send a message to the physician if adherence criteria fails." All other collection events 237 have their associated options parameter 232 default to indicate that the processor 102 is not to take any additional action with regards to the options parameter. It is to be appreciated that the above described features and arrangements illustrated embodiment of FIG. 7, provides a simply and convenient interface and method for customizing a structured collection procedure.

Implementing and Performing a Structured Collection Procedure

Figure 8A:
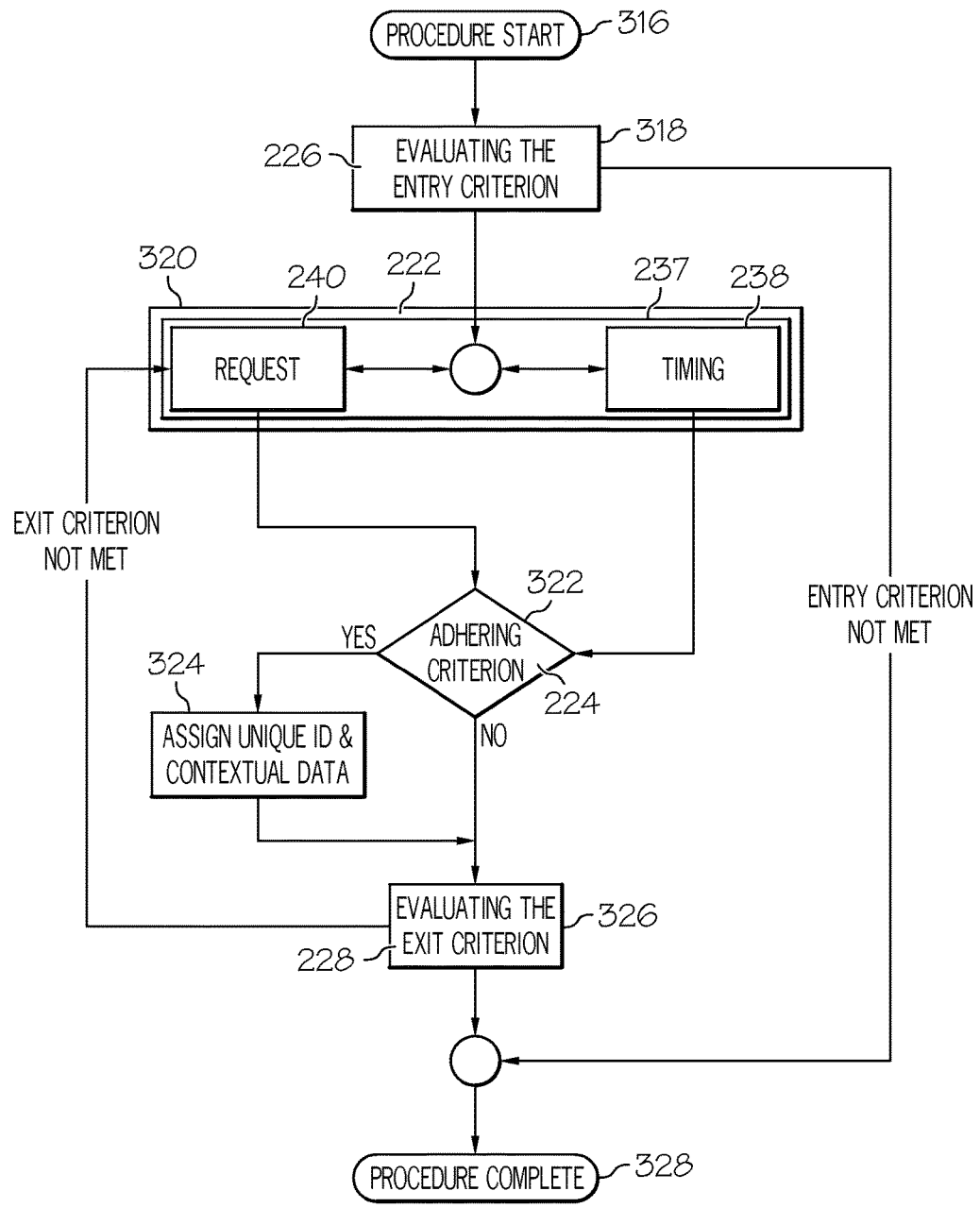
FIG. 8A shows a method for performing a structured collection procedure according to an embodiment of the present invention.

FIG. 8A shows a flowchart of the method for implementing and performing a structured collection procedure 70 to obtain contextualized biomarker data from a individual 12 according to an embodiment of the invention. It is to be appreciated that a number of structured collection procedures 70a-d (FIG. 2) may be stored in memory 110 (FIG. 3) of the device 24 and selected for execution at any desired time. For example, upon pressing a certain combination of the buttons 147, 149, the individual can select a desired structured collection procedures 70a-c and the date when to start a collection i.e., a set mode function. For example, a date range to choose from may be to begin the testing tomorrow and end at today +90 days, which the processor 102 can also recorded in the data file 145 (FIG. 4) as part of the setup data 163. In such an implementation, the processor 102 as instructed by the software 34 reads the setup data 163 for the selected procedure 70 and indicates on the display 108 that the device 24 is the structured tailoring mode, for example, a day before the chosen start date.

It should be appreciated that multiple structured collection procedures 70a-d can be executed sequentially or simultaneously at any given time. However, in one embodiment, the software 34 permits the user only to schedule another structured collection procedure 70 if the start date is later than the end date of the current structured collection procedure 70 being executed. The software 34 also permits the user to override a scheduled date for a structured collection procedure 70. If a structured collection procedure 70 is scheduled and the user enters the set mode function again, the software 34 causes the processor 102 to display the scheduled date on the display 108 as the default date; if the user exits the set mode without modifying the date, the previously scheduled date stays active. If a structured collection procedure 70 has started, the software 34 permits the user to enter the set mode and cause the processor 102 to cancel the current structured collection procedure 70. Upon cancellation, in one embodiment, the software 34 causes the processor 102 to de-tag (e.g., null the unique identifiers 167) the data records 152 in the data file 145 for the data collected for the cancelled structured collection procedure 70.

Upon reaching the procedure start in step 316 (FIG. 8A), the processor 102 evaluates the whether entry criteria 226 is met in step 318 to begin the structured collection procedure 70 selected to obtain biomarker data to address a predefined use case or question (e.g., use case parameter 220). In step 320, the processor 102 specifies requests 240 according to their associated timing 238 for each event 237 in the schedule of events 222 for the structured collection procedure 70. It is to be appreciated that the schedule of events 222 provides a sampling plan for biomarker data collection that is performed by the processor 102 to obtain biomarker data in a predefined context. In performing the schedule of events 222 in step 320, the software 34 causes the processor 102 to assign a unique identifier (e.g. incremental count) 167 in a date record 152 which corresponds to each event 237 in the structured collection procedure 70. Optionally, each criteria 226, 228, 224 may also be provide with a date time stamp 169 to indicate when such criteria was satisfied, if desired.

Adherence criteria 224 is then applied to the input received (e.g., biomarker data or information) in response to an request 240 to determine whether the input received meets the adherence criteria 224. When a structured collection procedure 70 has started, all data collected according to requests 240 in the structured collection procedure 70 and which satisfy the adherence criteria 224, if required in step 322, are then assigned (tagged) in the data file 145 by the processor 102 with the unique identifier 167 in step 324. It is to be appreciated that the unique identifier also serves to associates the collected data e.g., data values 256 with their event 237, the request 240, and a date-time stamp 169 to indicate when the collection in response to the request 240 was received by the processor 102. While a structured collection procedure 70 is being executed, in one embodiment the software 34 permits the user to perform a measurement on the device 24 at any time without interfering with the episode.

In one embodiment, the software 34 permits reminders for biomarker measurements to be 'snoozed' as mentioned above for a period, such as for example, 15 minutes and up to a number of times, for non-critical measurements. In another embodiment, biomarker measurements or data entries that are performed close enough in time to a request 240 in step 320 are designed as valid measurements or data entry for the request 240 by the software 34. As such, the processor 102 will tag the associated data record 152 for the event 237 with the unique identifier 167 for such a biomarker measurement or data entry accordingly. In the case of biomarker measurements, if the measurement is accepted as valid for the request 240, the software 34 causes the processor 102 to prompt the user to input additional information if needed by the structured collection procedure 70 to provide context 252 for data resulting from the request 240. Such additional input, may include, for example, a rating of energy level from 1 to 5, where 1 is low and 5 is high; meal size from 1 to 5 where 1 is small and 5 is large, and exercises from yes or 1 to mean over 30 minutes, and no or 2 to mean less than 30 minutes. Such additional information or contextual information 156 when inputted via the user interface 146 is stored by the processor 102 in the data file 145 associated with the unique identifier 167 for the data event request 240 requiring the additional information also in step 324.

In one embodiment, biomarker measurements determined by the processor 102 as not being close enough in time to the data event request 240 defined by the structured collection procedure 70 will not be tagged with a unique identifier 167 in the data file 145 by the processor 102. Such is illustrated in the shown data file 145 with request 240d and data values 256d not being associated with a unique identifier 167 e.g., <null>. An example of a definition of 'close enough in time to the collection procedure' as instructed by the structured collection procedure 70 and/or software 34 to cause the processor 102 to make such a determination may be defined as being relative to a prescheduled time or a snoozed time. For example, for pre-prandial measurements up to 15 minutes in anticipation is acceptable; for post-prandial measurements, up to 10 minutes in anticipation is acceptable; and for bedtime measurements, up to 15 minutes in anticipation is acceptable. Other definitions may be provided in other structured collection procedures 70 and/or software 34.

In step 326, the processor 102 then evaluates whether the exit criteria 228 for the selected structured collection procedure 70 is satisfied. If not, then the processor 102 continues with performance the schedule of events 222 until the exit criteria 228 is satisfied. Upon satisfying the exit criteria 228, the collection procedure 70 ends in step 328. In one embodiment, the structured collection procedure 70 may also end if in step 318, the entry criteria 226 is also not met.

In some embodiments, the structured collection procedure 70 can be configured for performance as a paper tool 38; diabetes software 34 integrated into a collection device 24 such as a blood glucose meter 26; diabetes software 34 integrated into the computing device 36, such as a personal digital assistant, handheld computer, or mobile phone; diabetes software 34 integrated into a device reader 22 coupled to a computer; diabetes software 34 operating on a computer 18, 25 such as a personal computer; and diabetes software 34 accessed remotely through the internet, such as from a server 52. When diabetes software 34 is integrated into a collection device 24 or a computing device 36, the diabetes software 34 can prompt the individual to record diary information such as meal characteristics, exercise, and energy levels. The diabetes software 34 can also prompt the individual to obtain biomarker values such a blood glucose values.

GUI Interface Providing a Selectable Structured Collection Procedure

Figure 8B:
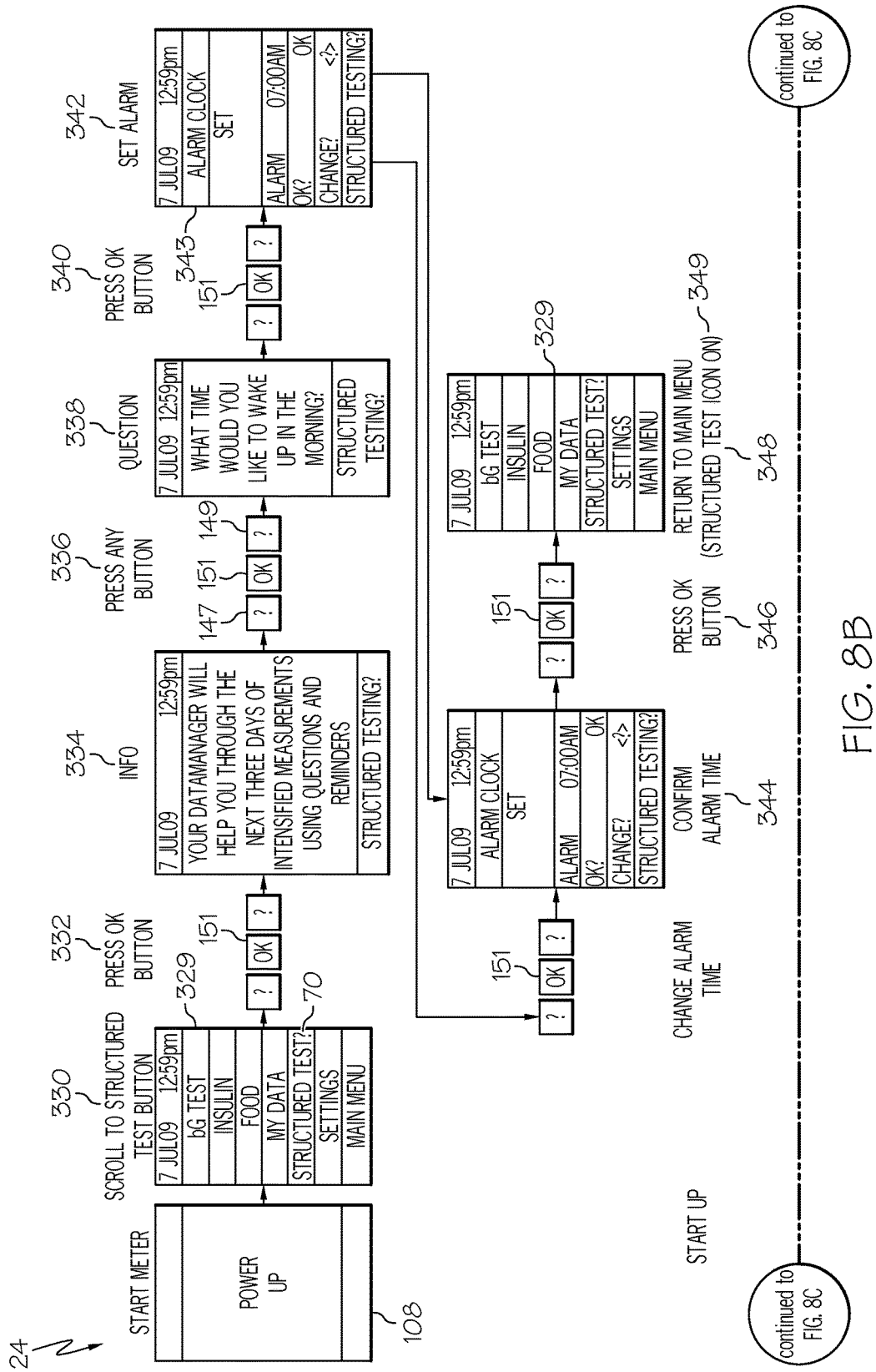

FIG. 8B shows a method of implementing the structured collection procedure via a graphical user interface provided on a collection device 24, which when executed on the collection device, cause the processor 102 to perform the following steps. Upon pressing a certain combination of the buttons 147, 149, the individual 12 can scroll to the structured collection procedure 70 available for selection in a list 329 provided by the processor 102 on the display 108 of the collection device 24 in step 330. If desiring to start the structured collection procedure, the individual 12, for example, selects via pressing an OK button 151 in step 332, the desired structured collection procedure 70. In this example, the entry criteria 226 (FIG. 7) of the structured collection procedure 70 provides information in step 334 which the processor 102 displays to the user on the display 108. After reading the displayed information, the user presses any button in step 336 in which the next procedure in the entry criteria 226 is performed by the processor 102. In this illustrated example, as part of the entry criteria 226, a question is then asked in step 338 by the processor 102. If the individual 12 is still desirous of starting the structured collection procedure, the individual 12 selects the OK button 151 in step 340; otherwise, any other press via button 147, 149 will cause the processor to go back to the list 329, thereby stopping the set-up procedure for the structured collection procedure 70.

After the individual 12 presses the OK button 151, the processor 102 in step 342 will provide on the display 108 an alarm clock 343 for setting the time to begin the selected structured collection procedure 70. It is to be appreciated that all the required events 237 for biomarker sampling, patient information, etc., is automatically schedule by the processor 102 in accordance with the schedule of events 222 for the structured collection procedure 70 in which timing, values, questions, etc., therein may have been adjusted as discussed previously above in reference to FIG. 7. Therefore, other than entering the start time as permitted by the entry criteria 226, no other parameter adjustments in the structured collection procedure 70 is required by the individual 12 (or permitted in one embodiment).

In the illustrated embodiment, the individual in step 344 can adjust the start time of the structured collection procedure for the next day, e.g., Day 1, via buttons 147, 149. Upon confirming the start time in step 346 via pressing the OK button 151, the start time is recorded in memory 110 as part of the setup data 163 in the data file 145 (FIG. 4) for the structured collection procedure 70 by the processor 102. The processor 102 then displays the selection list 329 on the display 108 in step 348, thereby completing the set-up procedure, which satisfies the entry criteria 226, and indicates on the display 108 that the collection device 24 is in a structured tailoring mode 349.

It should be appreciated that in one embodiment multiple structured collection procedures can be executed sequentially or simultaneously at any given time, and hence in one embodiment the mode 349 provided on the display 108 will indicated which structured tailoring is being performed. However, in one preferred embodiment, the software 34 does not permits the user to schedule another structured collection procedure, unless the start date is later than the end date of the current structured collection procedure being executed via the user interface 146. It is to be appreciated that processor 102 may re-schedule the following structured collection procedures automatically if the current structured procedure is still running due to the exit criteria 228 not being met. The software 34 in another embodiment may also permit the user to override a scheduled date for a structured collection procedure. If a structured collection procedure is scheduled and the user enters the set mode function again, the software 34 causes the processor 102 to display the scheduled date on the display 108 as the default date; if the user exits the set mode without modifying the date, the previously scheduled date stays active. If a structured collection procedure has started, the software 34 permits the user to enter the set mode and cause the processor 102 to cancel the current structured collection procedure, if desired.

In step 350, an alarm condition 351 can be provided by the processor 102 the next day (as indicated by the symbol Day1) as was set in the above-mentioned procedure the previous day (as indicted by the symbol Start Up). Upon the user selecting any button 147, 149, 151 in step 352, the processor 102 as instructed by schedule of events 222, provides a first scheduled event 237 which is information 353 to be displayed on display 108 in step 354, which the individual 12 acknowledges with any button 147, 149, 151 being pressed in step 356. Next in step 358, the processor 102 is instructed by the schedule of events 222 to execute a second scheduled event, which is to display on the display 108 a question 359 for the individual, which the individual 12 acknowledges with any button 147, 149, 151 pressed in step 360. In the illustrated embodiment, the individual in step 362 indicates the start time of breakfast in minutes from the wake up alarm 351 previously acknowledged in step 352. Upon confirming the meal start time in step 364 to the processor 102, via pressing the OK button 151, the meal start time is recorded in memory 110. For example, the meal start time is recorded in the data file 144 in the associated data record 152 as data for the event 237 by the processor 102. Additionally, in step 366, the processor 102 displays to the individual 12 the information regarding the timing for the next schedule event as a reminder. In step 368, upon reaching the next scheduled event indicted by the schedule of events 222, the processor 102 provides a request 240 on the display 108 for the individual to take a measurement, e.g., a blood glucose measurement. Additionally, in step 370, the processor 102 also makes a request 240 for information on the size of the meal that is to be ingested as required by the schedule of events 222 in order to provide contextual information 156 to the measurement value.

As mentioned above previously, for each event the software 34 causes the processor 102 to assign a unique identifier (e.g. incremental count) 167 (FIG. 4) to the data of each request 240 provided in the schedule of events 222 which meet the adherence criteria 224 in the associated date record 152 for the event 237. Therefore, while the structured collection procedure is being executed, the software 34 permits the user to perform a measurement on the collection device 24 at any time out side the schedule of events 222. Such a measurement since not being performed according to a request 240 will not be evaluated for the adherence criteria 224, and thus will not be provided with a unique identifier 167 in the date file but will only be provided with a date-time stamp and its measurement value. Such data is still recorded in the data file 145, as such data may still be useful for another analysis.

In another embodiment, the software 34 also permits reminders for biomarker measurements, such as provided in step 238. For example, in one embodiment, the processor 102 provides an alarm and/or alert message for a reminder via the indicator 148 and/or on the display 108, respectively, to provide a measurement. For example, at the time 238 of a particular request 240 for taking a biomarker measurement (or reading), the processor 102 prompts the individual 12 by al least displaying on the display the message, "It is now time for your reading." An audible alarm and/or tactile alarm (vibrations) can be provided by the processor 102 via indicator 148 in another embodiment. For example, in one embodiment, the collection device 24 will provide such a prompt even when already powered on, such as by the individual 12 for another reason, e.g., to conduct a non-scheduled event, when in, for example, a window of time in which to take the requested measurement/reading, or even when powered downed, such as in a standby mode, by waking up to provide the reminder via the prompt. In another embodiment, the provided reminder or prompt can be 'snoozed' for a pre-defined period as mentioned above, that still falls within the window of time in which to take the requested (critical) measurement/reading such as for example, 15 minutes or any other such suitable time that falls in the window of time. It is to be appreciated that the snooze feature for a measurement/reading that is considered critical to the procedure 70, e.g., a measurement/reading needed for helping to address the medical use case or question, needed to meet adherence criteria 224, and/or needed in subsequent analysis for some determination, etc., the snooze feature will not extend the request 240 beyond the window of time provided by the collection procedure 70 via, e.g., adherence criteria 224 for the request 240. For example, in one embodiment one or more events 237 in the schedule of events 222 can be pre-defined as critical as well as being a primary sample via use of the options parameter 232 (FIG. 7) provided in the structured collection procedure 70. For example, an event 237 which is designated as critical is one that cannot be missed, but if missed can be replaced by another sample already in the date file 145. An event 237 which is designated as a primary sample is one that cannot be missed, and which cannot be replaced by another sample, even if available in the date file 145. In still another embodiment, the snoozing can be up to a number of times, for non-critical measurements. For example, certain events 237 in the structured collection procedure 70 could be designated as having a non-critical request 240, which can be snoozed, such as via selecting such an option that is provided as one of the options parameter 232 (FIG. 7). The options parameter 232 in this embodiment could for example provide the snooze option as well as a selectable time interval (e.g., 1-60 minutes, etc.) and a selectable number of times (e.g., 1-5, etc.) that the user is permitted to snooze the request 240. In still another embodiment, the collection device 24 permits for an alarm shut off i.e., the indicator 148 if providing the reminder (audible, vibratory) can be shut off for the entire window of time via the user interface 146, but wherein processor 102 still accepts the measurement/reading as long as it is made in the window of time. In still another embodiment, the collection device 24 provides a skip reading option also received by the processor 102 via a selection entered using the user interface 146, e.g., from a list of selectable options, such as for example, snooze, alarm shut off, skip reading, provided on the display 108, in which again no reminder/prompt will be provided as individual 12 has indicated to the processor 102 that he/she does not want to take that particular requested measurement/reading. It is to be appreciated that selecting the skip reading selection option can result in an adherence event 242 resulting in further processing, such as discussed previously above in early sections, if adherence criteria 224 had been associated with the event 237 prompting the request 240.

In still another embodiment, the adherence criteria 224 can require biomarker measurements to be performed close enough in time to a data event request 240. Therefore, if such biomarker measurements are performed within the period specified by the adherence criteria 224, the processor 102 can indicate that the measurements or data entry for the event is acceptable and tags (i.e., assigns the unique identifier 167) the value of the biomarker measurement or data entry in the data file 145 accordingly. In the case of biomarker measurements, if the measurement is accepted as valid for the data event request 240 (i.e., meets the adherence criteria 224), the schedule of events 222 may causes the processor 102 to prompt the user to input additional information if needed by the structured collection procedure 70, such as mentioned above regarding step 370 to provide contextual information 156 (i.e., context) to the measurement received in response to a request 240.

Such contextual information 156 when inputted via the user interface 146 can be stored by the processor 102 in the data file 145 associated with the unique identifier 167 for the data event request 240 requiring the additional information. Biomarker measurements determined by the processor 102 as not being close enough in time to the data event request 240 as defined by the adherence criteria 224 will not be tagged in the data file 145 by the processor 102. Such is illustrated in the shown data file 145 (FIG. 4) with data event request 240d and data values 256d not being associated with a unique identifier 167. An example of a definition of 'close enough in time to the collection procedure' as instructed by the adherence criteria 224 to cause the processor 102 to make such a determination may be defined as being relative to a prescheduled time or a snoozed time. For example, for pre-prandial measurements up to 15 minutes in anticipation is acceptable; for post-prandial measurements, up to 10 minutes in anticipation is acceptable; and for bedtime measurements, up to 15 minutes in anticipation is acceptable. Other definitions may be provided in other adherence criteria 224 for other events in the schedule of events 222 as well as in other structured collection procedure.

In the illustrated embodiment, the user uses the buttons 147, 149 to scroll to a selection, which is entered by the processor in the data record 152 for the associated request 240 via pressing Okay button 151 in step 372. In one embodiment, the meal size can be indicated via a number range, such as for example, from 1 to 5, where 1 is small and 5 is large. In the illustrated embodiment, additional input for contextual information 156 regarding a rating of energy level from 1 to 5, where 1 is low and 5 is high is requested in step 374, which is entered in the data file 145 as mentioned previously above via the processor 102 receiving input for the request 240 by using the user interface 146 in step 376. In other embodiment, other contextual information 156 may include indicating whether the individual exercised and/or how long. For example, the user interface 146 may be use in which yes or 1 to mean over 30 minutes, and no or 2 to mean less than 30 minutes. In the illustrated embodiment, as the exit criteria 228 is now meet via successfully performing steps 368-376, the structured collection procedure 70 ends in step 378, wherein the processor 102 again displays the list 329, such that the individual 12 may perform other tasks on the collection device 24 if so desired.

Generation, Modification, and Transfer of Collection Procedures

Embodiments of the present invention also enable the generation, modification, and transfer of collection procedures 70 to and from the collection device 24. As the collection procedures 70 stem from and aim to address specific medical use cases or questions, the transfer of the resultant information e.g., data file 145, from one device to another is carried out in a secure manner. Additionally, a method whereby all of the collection procedure related information (e.g., data file 145) for an individual or a group of individuals can be managed in a secure and efficient manner.

It is to be appreciated that the discussion provided hereafter includes aspects related to the interaction between the clinician 14 and the individual 12. In particular, the disclosure hereafter provides details regarding the infrastructure required to manage the generation, transfer, and analysis of the collection procedures 70. Reference hereafter is also made to the system 41 of FIG. 2, as aspects pertaining to the transfer of devices and information (data, reports, etc.) to and from the devices 18, 25 and 52 are provided.

In one illustrated embodiment, the system 41 can comprise server 52 being a web-server that serves as a repository of a plurality of collection procedures 70a, 70b, 70c, 70d, as software 34 that resides on the clinician computer 25, and the collection device 24, such as provided as a blood glucose meter. Henceforth these components are referred to as the "server", "software", and the "meter" respectively. Additionally, the computer 25 where the software 34 resides is termed as the "client".

In one embodiment, the server 52 can serve as a central repository for a number of collection procedures 70a, 70b, 70c, and 70d that address specific medical questions. Accordingly, one or more collection procedures 70 can be downloaded from the server 52 to the clinician computer 25. In such an embodiment, all communications between the server 52 and the client computer 25 is done in a secure and web-based format. Additionally, in another embodiment, there is no full two-way data transfer between the computer 25 and the server 52 such that data can never be transferred to the server 52. Furthermore, in other embodiment, a request for a collection procedure from the server 52 can be made only with a valid identifier. Such an embodiment ensures that only authorized clients are allowed to access the server 52 to download the requested collection procedure(s) 70.

In one embodiment, each collection procedure 70 downloaded from the server 52 can be used only once (e.g., if the completed flag or state is set, the procedure 70 cannot be run again until reauthorized by the clinician 14). Each successive download of the collection procedure 70 requires access from an authorized client user with a valid ID 71 (FIG. 2). The server 52 also provides the client computer 25 with updates thereby ensuring that the software is the most recent version. There also exist restrictions on the communication from the client computer 25 to the server 52. The server 52 can only access information related to the installed version of the software 34. It is not possible for the server 52 to access any data resident in the client database e.g., memory 78. Additionally, the data on the client computer 25 is access controlled so that it cannot be used and accessed without the necessary permissions.

The software 34 residing on the client computer 25 serves as the interface between the server 52 and the meter 24. The software 34 at the front end includes a user-friendly interface that provides the clinician 14 with ready information pertaining to the overall practice. This information may include details about all assigned individuals, details about the individuals the clinician 14 is scheduled to see on a given day, as well as the details about individuals that need extra attention. The software 34 also interfaces with a database that includes relevant data that is arranged by an individual patient ID, such as used by and provided in the healthcare record system 27. The software interface also allows the clinician 14 to access the individual 12 details using the individual identifier. In this manner the software 34 provides the clinician 14 with information about the collection procedure(s) 70 that the individual 12 has already completed (i.e., those with a completed set for the completion flag 257), the associated results, and also the collection procedure(s) 70 that the individual 12 is currently performing. All of the data residing on the client computer 25 is secure and access-controlled. The server 52 has no means to access the data. The clinician 14 can access data from all individuals in the practice. In addition, an individual 12 can access his data, such as from a server of the clinicians, using his/her patient identifier in a secure web-based format. This data is downloaded to the database on computer 25 from the meter 24 and associated to the individual 12 using the individual identifier.

At the time of data download from the meter 24, the software 34 also performs an analysis on the data to ensure that the integrity of the data is maintained and no corruption in the data has taken place at the time of transfer. The client computer 25 with the help of the software 34 can also send emails to the individuals and these emails can contain information about an upcoming appointment, reminders on what the individual is supposed to do after an appointment and reports that are results of a completed collection procedure 70. When the clinician 14 downloads a collection procedure 70 from the server 52 for a particular individual, the collection procedure 70 is associated with the individual identifier. In this way, it is possible to account for what collection procedures 70 are currently underway for each of his patients.

A downloaded collection procedure 70 can also be modified by the clinician 14 and/or by the individual (if permitted by the collection procedure 70 such as discussed hereafter in reference to process 700) using the software 34 to tailor the collection procedure 70 to each individual's needs as previously discussed above in earlier sections (FIG. 7). At the time of modification of the collection procedure 70, the clinician 14 (or individual 12 if so permitted) also has the option to alter the analysis that will be carried out on the modified collection procedure 70. Additionally, even for standard collection procedures 70 that have not been modified, the clinician 14 has the option to add additional options for analysis.

Furthermore, the clinician 14 (or individual 12 if so permitted) can decide and set guidelines as to when the procedure 70 must terminate. For example, the clinician 14, can decide and set how many adherence violations are allowed, i.e., how many measurements can the individual miss, such as via using the options parameter 232 in the collection procedure 70.

Once a collection procedure 70 is introduced into the meter 24 by the clinician 14 (details discussed in the next section), such clinician defined collection procedure 70 cannot be altered by the individual 12, i.e., except for those collection procedures which can be personalized by the individual as discussed hereafter in a later section. Additionally, the collection procedure 70 is associated with both the clinician 14 (the prescriber) and the individual identifiers to ensure accounting of the collection procedure 70 and associated data (e.g., data file 145).

The software 34 also allows the clinician 14 to select the type of report that will be generated once the completed collection procedure 70 has been analyzed. This report is tailored for the device on which it will be viewed. The report could be for a mobile device such as a telephone, a palm device or a meter, or a computer, or a printed format. The software 34 also has the ability to connect with an electronic medical records system to add data and results of analysis performed on the data from a collection procedure 70 to the medical records.

The meter 24 serves as the mechanism by which prospective and contextualized data is collected by the individual 12 as recommended by the collection procedure 70. The meter 24 can be owned by the individual or it can be owned by the clinician 14 and loaned to the individual 12 for the duration of the data collection associated with the collection procedure 70. The clinician 14 can introduce the collection procedure 70 into the meter 24 by a number of mechanisms. For example, the collection procedure 70 can be downloaded from the server 52 and added to the meter 24 via a connecting cable that links the client computer 25 to the meter 24 in one embodiment. The collection procedure 70 can also be obtained in another embodiment on a chip (e.g., computer readable medium 40) that can be inserted into the meter 24. This collection procedure 70 is then loaded into firmware of the meter 24 where it can be initiated by the individual 12. The collection procedure 70 can also be introduced using an RFID tagged chip (e.g., computer readable medium) in still another embodiment.

Along with the downloaded collection procedure 70, the meter 24 also has the ability to display instructions to the individual 12 that guide the individual at the time of data collection. Additionally, as discussed above, the collection procedure 70 can introduce into the meter 24 both the individual identifiers as well as the clinician identifier. Similarly, the data collected from the meter 24 can be associated with the individual identifier and clinician identifier, such as part of setup data 163 (FIG. 4) in the data file 145. Additionally, the setup data 163 in the data file 145 can include information about the meter 24 (i.e., measurement noise, calibration data), as well as strip lot numbers and other information about the strips used for any data collection event 237. Such information may be helpful at the time of data analysis.

At the completion of the collection procedure 70 the meter 24 can be connected to the software 34. At that time data, such as data file 145, is transferred securely and stored by the processor 76 of the client computer 25 according to the software 34 running thereon. Once the analysis performed on the data from the collection procedure is completed by the software 34 on the client computer 25, the device 24 also has the ability to store results of the analysis for later patient reference.

In still other structured collection procedure embodiments, at each aspect of running the collection procedure 70, right from initialization to the end of the execution, some sort of status reporting can be provided in which to aid the individual in executing and completing the structured collection procedure. The types of status reports which can be provided at each of the various aspects of execution of the structured collection procedure 70 is discuss hereafter with reference made to FIG. 9, which depicts another method for performing a structured collection procedure. It is to be appreciated that process steps shown in FIG. 9 having like numbering of process steps discussed in proceeding sections have like function, and thus no further discussion is provided for brevity.

Start of the Structured Collection Procedure.

In one embodiment, starting information 600 can be provided before the individual 12 initiates the structured collection procedure 70, or in another embodiment as part of the procedure start in process step 316 (FIG. 8A). The starting information 600 in one embodiment conveys to the individual 12 the reason(s) why the structured collection procedure should be carried out and also what results can be expected upon successful completion of the collection procedure 70. In other embodiments, the starting information 600 can include information regarding the entry criteria 226 that needs to be met in order to start the collection procedure 70 in process step 318. Additionally, general suggestions regarding the requirements for the adherence criteria 224, e.g., explaining what constitutes a measurement that cannot be used, e.g., not fasting, the requisite time before a fasting reading, etc., as well as encouragement, e.g., "The better the adherence, the better the results as well as the quicker the overall task will be completed," can be provided in still other embodiments of the starting information 600. In still other embodiments, specific information for the clinician 14 can also be included in the starting information 600, e.g., the intended user groups for the collection procedure 70, the burden of the collection procedure 70, and the likes. It is to be appreciated that such starting information 600 can be given as a printed report, can be made available in a secure fashion over the web so that it can be viewed on a computer, such as computer 18, 25 (FIG. 1), and/or displayed on the display 108 of the device 24, or on a display of any other appropriate handheld device. In still other embodiments, the starting information 600 is included as part of the guidance 230 (FIG. 10) provided by the structured collection procedure 70 at startup and/or can be pre-defined in the collection procedure 70 and customized by the clinician 14 as desired.

In still other embodiments, the starting information 600 can provide the anticipated total amount of time required to complete the collection procedure and the number of expected measurements. An example of such information provided by the starting information 600 for the total time and measurements may be a message which states "The anticipated amount time is about 4 weeks to complete the collection procedure which requires 30 fasting pre-breakfast measurements." It is to be appreciated that starting information 600 can be delivered in a number of different ways, in addition to the above mentioned means. For example, a calendar either printed, electronically provided on computer 18, via the web, and/or on device 24 can be provided which contains the days and times at which a measurement is to be made for performing the associated collection procedure 70.

During the Collection Procedure Execution

While the structured collection procedure 70 is being executed, for example, on the device 24, there are a number of indicators that can be provided to the individual 12 as status updates. These indicators help the individual 12 to know how he/she is performing in the execution of the collection procedure 70 and are also useful in providing guidance under special or adverse conditions that the individual 12 might encounter. Such status indicators include, but not limited thereto, the following examples.

Figure 9:
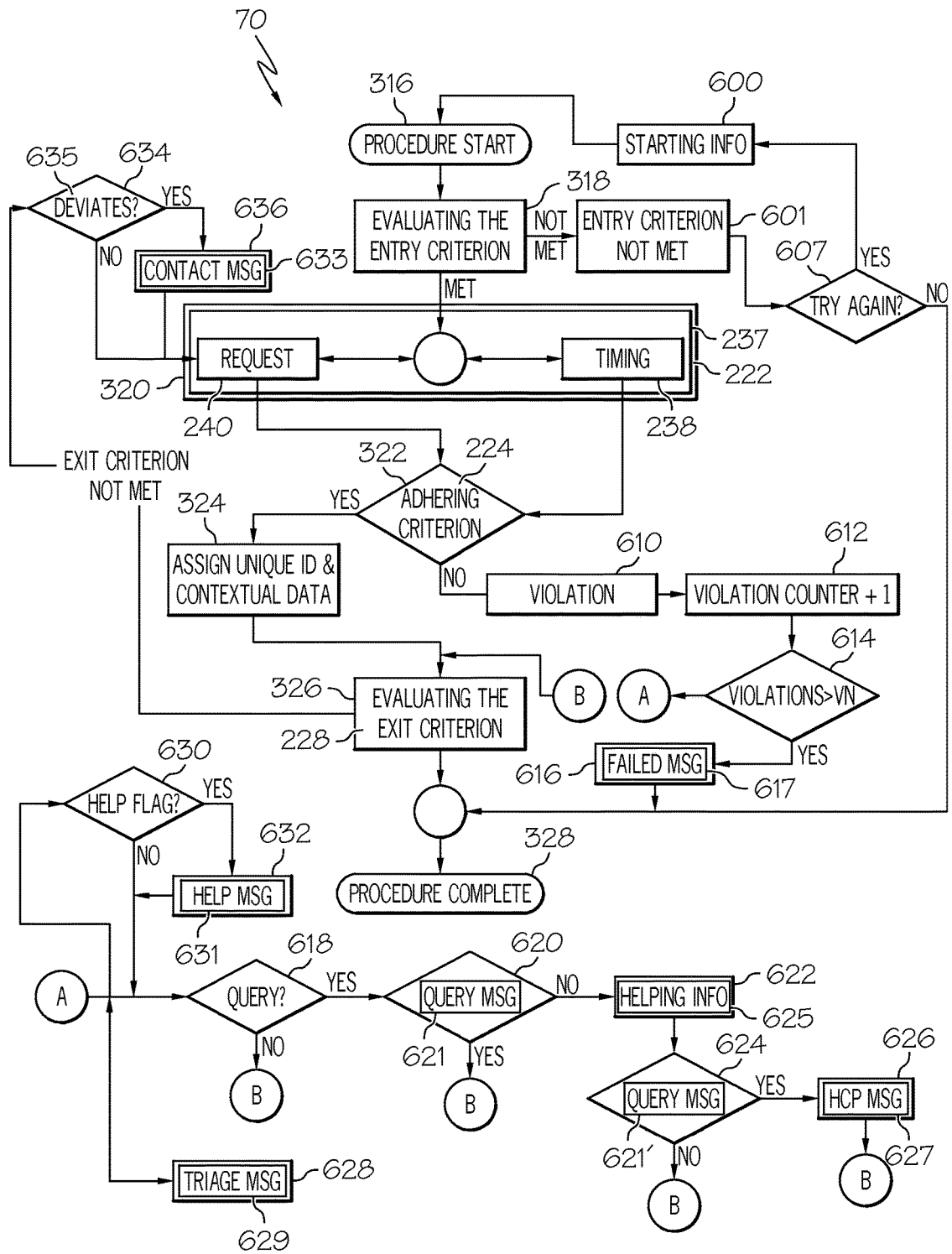
FIG. 9 shows a method for performing a structured collection procedure according to another embodiment of the present invention.

Initially, and as stated above in a previous section, the structured collection procedure 70 may end if in step 318, the entry criteria 226 is also not met. If the entry criteria 226 is not met in step 226, then in this alternative embodiment a message 601 may be provided which notifies the individual 12 of such a fact and which requests in step 607 whether to re-start the procedure by providing the starting information 600 again. In still other embodiments, the individual 12 can be given feedback on the extent of his or her adherence to the collection procedure 70. As shown by FIG. 9, in this alternative embodiment if after process step 322 the adherence criteria 224 is not met, then a violation counter is incremented in process step 612. In another embodiment, a violation message 610 may also be provided by the processor 102 on the display to notify the individual 12 that a violation has occurred. It is to be appreciated further that when a violation occurs, the processor 102 can also record the occurrence of the violation in an embodiment of the data file 145 in a violation field 611 for the associated event 237 as depicted by FIG. 4.

As also depicted by FIG. 4, type codes 613 may be provided in the violation field 611 by the processor 102 to indicate what caused the violation (e.g., "A" event performed before window, "B" event performed after window, "C" event skipped, "D" an event performed incorrectly, to provide context to the violation. For example, event 237*d*, which did not received a unique identifier 167 due to failing the adherence 224, from being skipped. As such the processor 102 recorded a "C" type code 613 in the violation field 611. Such context is information that the clinician and/or a running a process 700 can use in assessing how the collection procedure 70 may be adjusted to better suit the individual 12 in the future.

In process step 614, the number of violations (i.e., violation counter) is checked to see if it exceeds a maximum number of violations permitted (i.e., violation number (VN)) before automatic termination of the collection procedure 70 occurs for excess adherence violations. The violation number (VN(s)) 615 can be preset in the collection procedure 70 as depicted by FIG. 10 and adjusted by the clinician (and/or individual if permitted) as desired. In still other embodiments, a number of violation numbers 615 could also be provided in the collection procedure 70 wherein each violation number would be set for each of the Type Codes 613, such that if the violation counter for each Type Code 613 exceeded the associated violation number, the collection procedure 70 would terminate due to that specific type violation. In still other embodiments, the violation number 615 could represent the number of violations in a pre-defined period of time instead of an absolute number since the start of the collection procedure 70. For example, the pre-defined period time could be designed and adjusted by the clinician 14 (and/or individual if permitted) in the collection procedure by a time parameter (t) 619. For example, in one embodiment the processor 102 in step 612 would also check to see whether the violation counter exceeded the violation number 615 within the associated pre-defined period (t) 619, or in another embodiment any of the violation numbers associated with each Type Code 613 within their associated pre-defined period (t) 619. In the illustrated embodiment of FIG. 9, if the violation number (VN) 615 is exceeded in process step 614, i.e. the violation counter "Violations" is greater than the violation number (VN), then a failed message 617 is provided in process step 616 and the procedure ends in process step 328 as discussed previously above in an earlier section. The failed message 617 can be pre-defined in the collection procedure 70 as depicted by the FIG. 10 and customized by the clinician 14 as desired. The failed message 617 can be provided on the display 108 of the device 24 and/or to the clinician 14 via communication interface 124.

In one embodiment, the individual 12 can be told how many further adherence violations he/she can have before he/she might be forced to quit the structured collection procedure 70, such as part of the messages provided in the calendar embodiment. For example, the message may be "You have {Violation Counter} of {VN} permitted violations," or "You have {VN-Violation Counter} permitted violation remaining," where { } indicates the current parameter value. In other embodiments, after each violation which does not result in termination (e.g., Violation Count<VN in process step 614), the device 24 can check to see if the user should be queried, for example, in process step 618. If the result of process step 618 is no, such as in the case where no query message(s) 621 (FIG. 10) is defined in the structured collection procedure 70, then the process proceeds to process step 326. If the result of the process step 618 is yes, then in process step 620 the query message 621 is provided to the individual 12 on display 108 of the device 24. The query message 621 can be pre-defined in the collection procedure 70 as depicted by the FIG. 10 and customized by the clinician 14 (and/or individual if permitted) as desired.

For example, in one embodiment, the query message 621 may be a question asking the user if he/she understands the structured collection procedure 70. In the illustrated embodiment depicted by FIG. 9, the user may answer the query message 621 via selecting either a "yes" or "no", e.g., via the user interface 146 (FIG. 3). If "yes", then the collection procedure 70 would continue, such as at process step 326 (FIG. 9). If "no", then the device 24 provides helping information 625 in process step 622. Such helping information 625 may include re-displaying the starting information 600 pertaining to purpose of the collection procedure 70 and the requirements on how the collection procedure needs to be conducted and/or educational material as defined herein after in a later section. If after such information is displayed to the user e.g., on display 108, the device 24 in other embodiments can query the user further in process step 624 via presenting another query message 621'. The query message 621' can be, e.g., a request to see if the individual may need feedback from the clinician 14 to better understand why the violation occurred, to which the individual may answer yes or no via the user interface 146. If "no", then the collection procedure 70 would continue, such as at step 326, and if "yes", the device 24 could then send a message 627 in process step 626, e.g. via communication interface 124, to the clinician 14 to contact the individual due to an adherence violation. The query message 621', the helping information 625, and the clinician message 627 likewise can be pre-defined in the collection procedure 70 as depicted by the FIG. 10, and customized by the clinician 14 as desired.

It is to be appreciated that the above mentioned type of querying may help to get the individual 12 back on track with the collection procedure 70 due to minor misunderstandings. In still another embodiments, the adherence violation in process step 628 results in a triage message 629 being sent automatically (e.g., from device 24 to clinician computer 25 via network 50) to the clinician 14 to help the clinician 14 identify which individual 12s are at risk of not completing the structured collection procedure 70. Such messaging may prompt the clinician 14 to contact the individual 12 to provide information and further motivation.

In still other embodiments, the collection procedure 70 can provide possible ways to reduce the number of accumulated adherence violations through closer adherence. For example, the clinician 14 may at some point during the collection procedure 70 reset the violation counter and/or change the violation number 615. In still other embodiments, the device 24 can provide a way the individual 12 earns adherence credits based on a successfully completing a period of adherence that would cancel accumulated violations, and/or to earn a reduction in the pending violations by opting into a form of the procedure that provides more guidance on the aspects of the procedure that are the source of the violations. In still another embodiment, the device 24 can permit an individual who is having problems with testing at the correct time, to opt into a version of the procedure 70 that provides more prompting with the upcoming test, such as a reminder at the time of the test and another shortly before the end of the grace period for that test if it has not been performed. In still other embodiments, the number of accumulated adherence violations can be reduced by providing reminders at mealtime of taking post-prandial measurement, by indicating at measurement time, the time/details about next measurement, as well as by providing encouragement during protocol execution.

In still other embodiments, when an adherence violation occurs in a particular portion of the collection procedure 70, the device 24 can recommend that the user seeks help, such as to contact the clinician 14 to gain possible insight or motivation, and/or can provide particular information on where to seek such help. For example, the clinician could designed by the options parameter 232 for which particular events 237 such information is to be provided if a violation occurs. For such an embodiment, the processor 102 in process step 630 then checks to see whether such a designation has been made in the collection procedure 70 via help flag "*" being provided in the options parameter 232 for the event 237, e.g., for the "N1 hours after breakfast" event as depicted by FIG. 10, which in this case caused the violation. If such a help flag "*" is provided, then a help message 631 is in process step 632. For example, the information provided in the help message 631 can be included in the helping information 625, and can include, but not limited thereto, web addresses of online help content, and names and numbers of social support networks. The individual 12 in still other embodiments such information may also include suggestions on how to deal with the situation (s) where an adherence violation had occurred. For example, suggestions on what to do when a value of a physiological measurement collected in response to a collection event is out of the expected range can be provided. Such suggestions can be provided as a listing of frequently asked questions (FAQ) and answers. Still other suggestions can ask the individual 12 to make assessments as to whether the violation is a recurring pattern, or a singular data point attributed to a particular acute issues, such e.g., the individual is on vacation and therefore explainable, or chronic where nothing has changed, thereby possibly indicating that something physiological or medicinally has changed, and therefore a change may be needed before continuing.

As discussed in the previous sections provided above, when the individual 12 encounters a severe hypoglycemic event, the recommendation provided by the device 24 would be to contact the clinician 14. However, in still other embodiments, additional guidance can be provided to ensure that such an adverse event does not persist, e.g., eat some carbohydrates, measure again after some time, and the likes.

In still other embodiments, after the evaluating the exit criteria 228 in process step 326 (FIG. 9), the processor 102 then checks to see in process step 634 if a defined deviation(s) 635 from an expected behavior is occurring in the execution of the collection procedure 70, and if so, then the device 24 can suggest that the individual 12 contacts the clinician 14 via displaying a contact message 633 in process step 636. In one embodiment, the contact message 633 can be the same message as the failed message 617, or in another embodiment, it can be a customizable message (such as defined by the clinician and/or patient) in the collection procedure 70. Also, one example of when an individual's behavior deviates greatly from what is expected is as follows. When the individual 12 undergoes a titration structured collection procedure 70, if the processor 102 notes that data values 256 of the measured value for blood glucose in the data file 145 (FIG. 10) do not show any lowering of fasting bG values over a pre-defined period of time in spite of increasing dosages of insulin, the contact message 633 will be sent. Other such deviation examples can be pre-defined via logical operations (e.g., Boolean and conditional logic) provided in a deviation parameter 635 (FIG. 10) provided in the options of the collection procedure 70 and which can be customized by the clinician 14 (or individual in some embodiments when permitted by a process for providing a personalized collection procedure, such discussed hereafter in later sections) as desired.

Structured Tailoring

Figure 11:
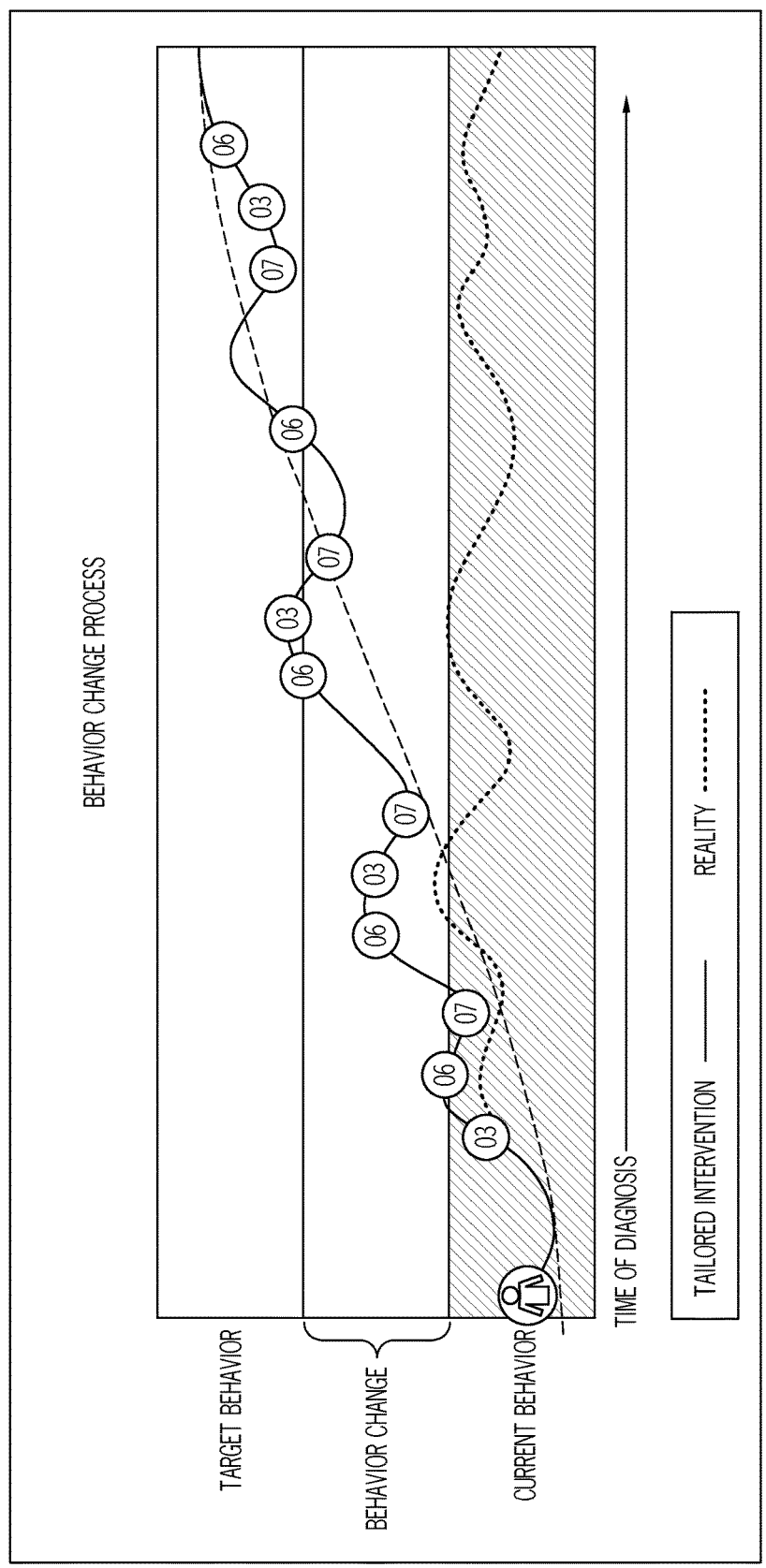
FIG. 11 depicts graphically a behavior change process according to an embodiment of the present invention.
Figure 12:
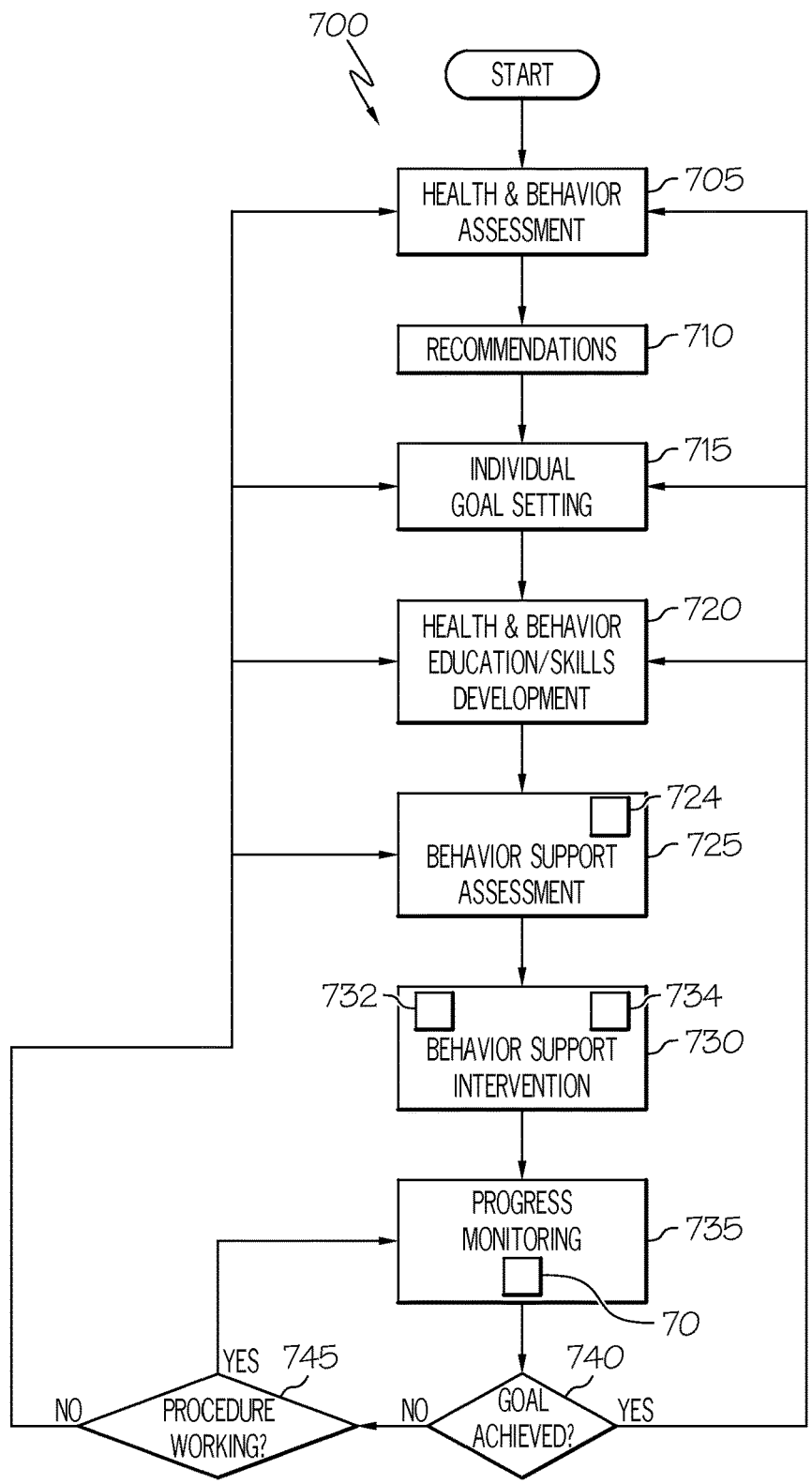
FIG. 12 shows a method for performing a structured tailoring process according to an embodiment of the present invention.
Figure 13:
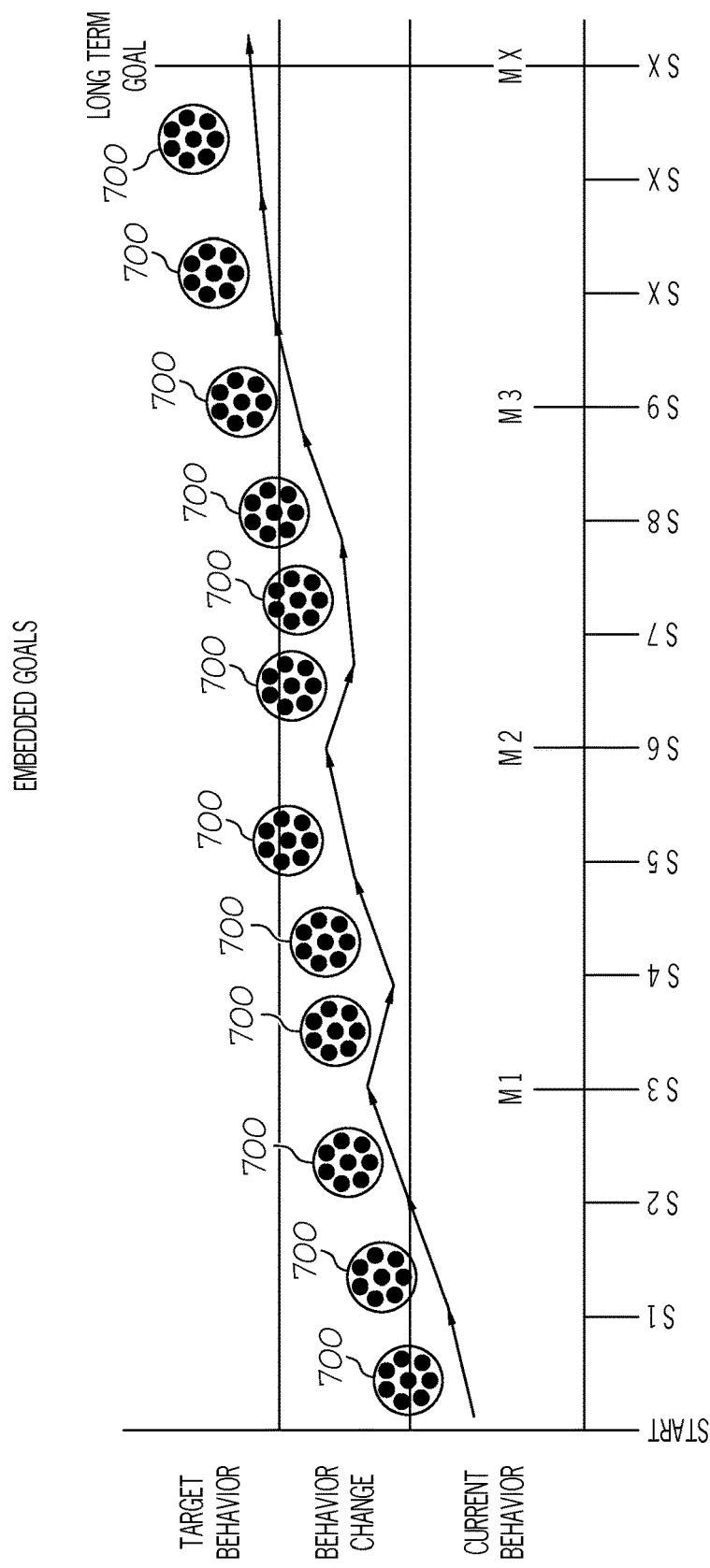
FIG. 13 depicts graphically embedded goals of the structured tailoring process according to an embodiment of the present invention.
Figure 14:
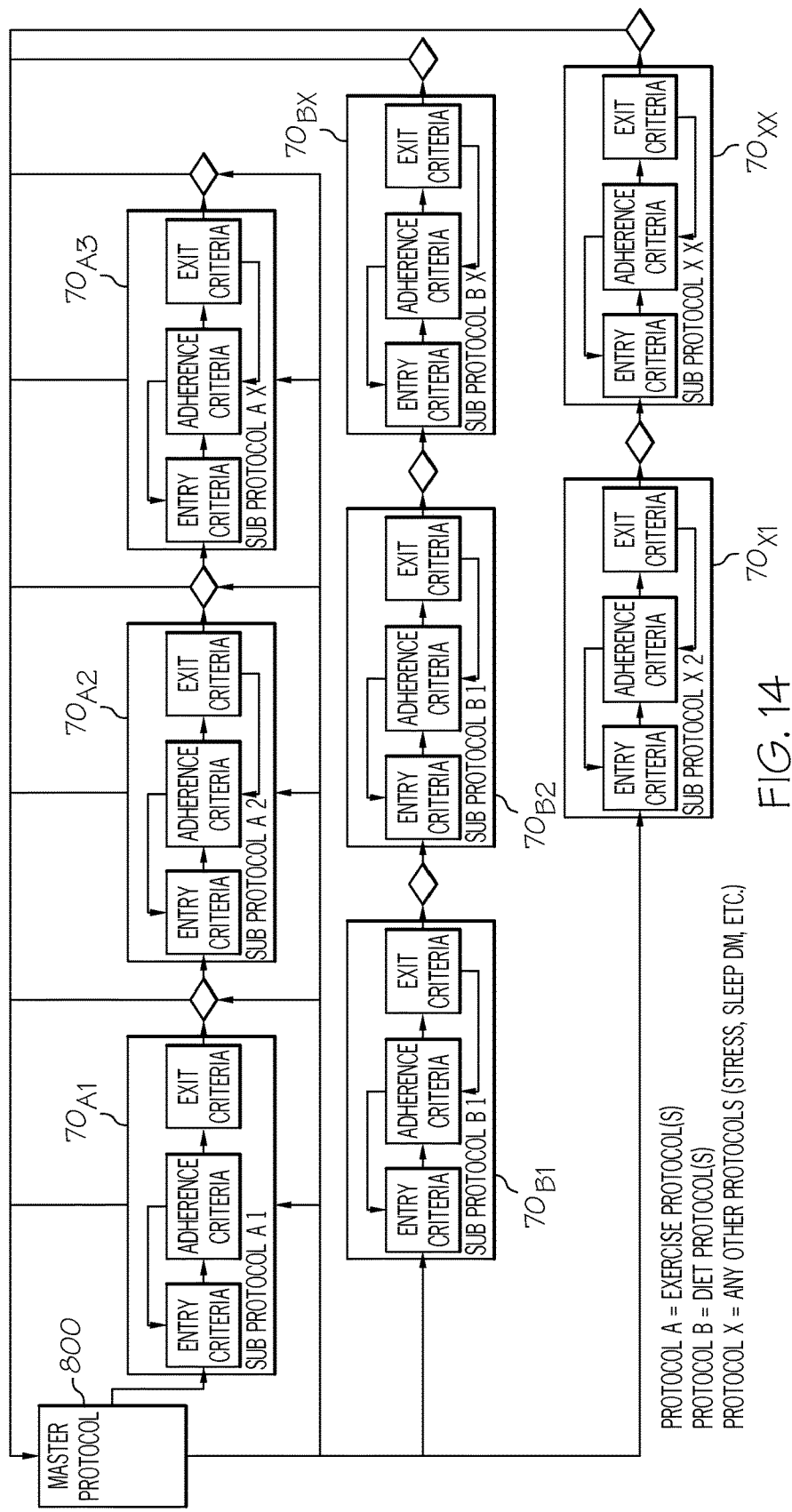
FIG. 14 depicts a master protocol of a structured tailoring process according to an embodiment of the present invention.

In still other embodiments, the structured collection procedure 70 can be further expanded to include structured tailoring in order to help improve the success of the individual 12 changing and maintaining health related behavior by individualizing behavior change action plans through the use of the entry, exit, and adherence criteria. It is to be appreciated that structured tailoring is a communication strategy for enhancing the efficacy of health and behavior change messaging. In particular, structured tailoring provides a framework to design and construct a patient specific system of education and action that can maximize the potential benefits for each individual. Structured tailoring uses a combination of relevant content that is intended to reach one specific individual, based on characteristics that are unique to that individual, and derived from an individual assessment. In particular, structured tailoring to assist in behavior change deals with improving the behavior change process (BCP). This is done by monitoring the users success in their behavior change process in terms of the input criteria to events 237, adherence criteria 224 and exit criteria 228. As depicted by FIG. 11, the idea is that many BCP programs do an adequate job in setting up goals and suggestions for users to monitor progress, but they fall short when the user begins to fail in adhering or continuing through the BCP. The BCP according to a process of the present invention discussed hereafter, provides a structured tailoring processes which systematically and automatically provides goal setting (symbol "03"), coaching through interventions (symbol "06"), and monitoring of the process (symbol "07"), in a cyclical fashion which provides incremental changes with each cycle that the individual 12 has personalize to help internalize acceptance or "buy in" into the BCP. With such internalized acceptance and support provided by the process, the individual then has the willingness and help to attain the desired target behavior. With reference made to FIGS. 12-14, an exemplary embodiment of a structured collection procedure suitable for structured tailoring is discussed hereafter.

As depicted by FIG. 12, a structured tailoring process 700 providing for a behavior change via tailored invention is disclosed, and which can be implemented as software instructions or program which will cause a processor or computer to carry out the following steps. The process 700 starts from the initial assessment 705 of the individual 12 to begin to tailor both the activities as well as the interventions provided to the individual when running the structured collection procedure 70 on the device 24 and/or computer 18 that has been personalized for structured tailoring of the individual. The initial assessment 705 can, for example, cover areas of readiness for change, current health, and activity level of the individual. Next, in process step 710 and in this example, based on the individual's readiness and current health, suggestions are made for the individual's particular protocol. For example, if the individual isn't ready, education, information and skill development (see process step 720) and messaging will be suggested and/or provided by the process for further contemplation and preparation for change. If it is deemed that the individual 12 is ready to change their behavior, the process 700 can recommend a starting point based on preselected use cases. This recommendation could be used as the entry criteria 226 of the procedure 70 in one embodiment.

Next, in process step 715, the individual 12 will then take the recommendation resulting from process step 710 and tailor it to his or her individual abilities and availability. Goals are setup in multiple levels from short term (e.g., S1, S2, S3, S4, S5, S6, S7, S8, S9, . . . , SX) to midterm (e.g., M1, M2, M3, . . . , MX), and then to a long-term goal as depicted by FIG. 13. The individual 12 can begin with just short-term goals, but as the individual continues to cycle through the process 700, they will eventually develop midterm and long-term goals. For example, short term goals S1, S2 and S3 could be intended just to start the change of the individual 12 in a positive direction towards an actual behavior change, in which the short term goals adjust the requirements for reaching the behavior change incrementally or progressively with each cycle of the process 700. In such an example, a first mid-term goal e.g., M1 as depicted by FIG. 13, can be that by the end of the third cycle of the process 700, i.e., that successful completion of the short time goals S1, S2, S3, the individual 12 is progressing with the necessary behavior change that will eventually result in the target behavior over a period of time. As depicted, a number of such mid-term goals can be formed of one or more short-term goals, and wherein in the above example, the additional mid-term goals M2 and M3 could be that the individual 12 continues with the desired behavior change, via the series of further short term goals (e.g., S4-S9), such that at the end of third mid-term goal, the individual 12 has accomplished the target behavior. Upon reaching the target behavior, the long term goal could be that the individual 12 has demonstrated the target behavior for at least X cycles of the process 700. It is to be appreciated that other variations and combinations of such short term, mid term, and long-term goals can be provided, other than what has been depicted in the illustrative embodiment of FIG. 13, as such goals will be customized by the individual to their own preferences via the reiterative nature of the process 700.

At the start of each cycle of the process 700, each short-term goal will be based on the results from the earlier associated assessment and recommendation processes 705, 710, respectively. For example, in the context of wanting to have the individual exercise more as the behavior change, a typical beginning short-term goal, e.g., S1, may be to have the individual just keep track of how much activity he or she is doing for the first week. The next short-term goal, e.g., S2, then set by the individual may be to walk for X number of minutes for X number of days. For the next series of short term goals, the minutes and days can increase in duration or the activity could increase in intensity overtime. Such individual defined goals are then used as the adherence criteria 224 e.g., exercising X minutes per day, and the exit criteria 228 e.g., have exercised X minutes per day for X number of days, for the collection procedure 70.

In process step 720, an education module 724 can be provided by the process 700 which provides education material, and which in other embodiments also can be accessed at any time (from any process step) during execution of the process 700. The education material may contain any type of health and behavior education in relation to exercise including, benefits of exercise, safety, making time to exercise, making exercise fun, how to do certain exercise, etc., and can be provided by the process 700 as electronic text, images, sounds as well as combinations thereof. The education material can also include a skill assessment as well as skill development activities. For example, the skill assessment permits the process 700 to check and assess if the individual possesses the proper level of skill before moving into a new activity and/or protocol, i.e., a different collection procedure 70. If not, then the process 700 then provides/recommends the skill development activities for the individual 12 to complete in order to gain the necessary skill level for the new activity and/or collection procedure 70.

Next, in process step 725, once the individual 12 identifies their goals, the process 700 then begins a behavior support assessment to ascertain from the individual 12 what barriers and motivators in the past have assisted in success or failures when it comes to performing the target behavior, for example, exercising, not smoking, not drinking, etc. These can be psycho-social like being bored (barrier), or having a partner to exercise with (motivator), etc., they can also be physical like being too tired or sick (barriers), or they can be environmental like inclement weather or safety concerns (barriers), or walking in a nice park outdoors (motivators). These motivators and barriers are self selected and configured by the individual based on their experience.

In process step 730, once the individual 12 has completed the behavior support assessment in process step 725, the process 700 then provides a behavior-support intervention module 732 in which the individual 12 picks a pre-defined intervention(s) based on their individual motivators and/or barriers. These interventions can take multiple forms from basic electronic alarms, reminders, messages, such as those discussed above in previous sections, as well as to elaborate social support networks utilizing GPS (such as when device 24 is a GPS enable device) to recommend available friends to exercise with or suitable places to exercise that are near to the individual. These interventions are self selected and configured by the individual 12 based on his or her preferences. The process 700 also provides a validation module 734 to ascertain that the appropriate level of intervention is assigned due to the associated risk of non-adherence. In one embodiment, if the validation module 734 determines that an appropriate level of intervention has not been assigned, suggested levels of interventions can be presented to the individual for selection, and/or selected for the individual if no other choices are available. Once the individual 12 has designated the desired intervention(s) in step 735 (or which has been automatically assigned by the validation module 734 as previously explained), events 237 which define a plan of action (i.e., the schedule of events 222) in the collection procedure 70 for the individual 12 are generated by the process 700. For example, the events 237 will define how often progress will be monitored (daily/multiple times a week in the beginning). The individual 12 can then customize and/or accept the plan of action (i.e., the schedule of events 222) defined by the events 237. Next, after accepting the plan of action, the individual 12 will then start the procedure 70 with all the agreed upon interventions (alarms, reminders, messages, etc.) upon meeting the entry criteria 226, e.g., indicating to the device 24 a readiness to change the associated behavior by using the now personalized procedure 70 providing tailored events and interventions for accomplishing a short term goal of changing a current behavior of the individual to a targeted behavior.

Next, in process step 735, the device 24 or computer 18 running the personalized procedure 70 monitors compliancy of the individual with the plan of action i.e., schedule of events 222, such as discussed previously above with reference to FIG. 9, as further modified as discussed hereafter. If activities (i.e., events 237) are on track (i.e., adherence criteria 224 is met), then the process 700 checks to see if the defined goal has been achieved by seeing if the exit criteria 228 is met in step 740, which is similar to step 326 in FIG. 9. Likewise, if the goal is not met i.e., exit criteria 228 is not met, then in process step 745, the process 700 checks to see whether the personalized collection procedure 70 is working which is also similar to process step 634 i.e., checking for a deviation 635, shown in FIG. 9.

For example, for this illustrative embodiment of structured tailoring, a deviation 635 used in process step 745 in one embodiment can be an indication provided to the process 700 by the individual (e.g., via a user interface 146) and/or a showing in the collected data that the weight of the individual and/or some other physiological value (blood pressure, heart rate, etc.) of the individual is not trending toward an expected predefined value after a predetermined period of time. Still other examples of such a deviation simply may be a question presented to the individual (e.g., via the display 108 or on computer 18) asking the individual 12 as to whether the individual believes that the process 700 is working, whether the individual 12 is following their own intervention, or whether the individual 12 is lacking in a skill and/or understanding of how reach/attain the goal.

If the personalized procedure 70 is not working to support a positive change in behavior (i.e., a deviation 635 has occurred) a contact message (i.e., message 633) can optionally be sent (i.e., process step 636), but unlike the collection procedure 70 depicted by FIG. 9, in this illustrative embodiment of FIG. 12, the individual will be requested by the process 700 to go back to an earlier process step based on the type of deviation. In particular, if the result and/or the procedure 70 are not working in step 745, then the process 700 will take the individual 12 back to the appropriate area e.g., Health and Behavior Assessment (are they ready for change?), goal setting (input criteria), Education/skills development (are they capable?), or behavior support (are there more barriers or motivators plans necessary for success?), so the individual 12 can re-set the procedure 70 to ensure success.

For example, if the personalized collection procedure as a whole is indicated (by either the individual or the collected data) as not working, the process 700 loops to process step 705, i.e., for another health and behavior support assessment in order to work through the process of providing a new personalized collection procedure 70. If, however, one or more of the set goals of the procedure 70 are indicated (either by the individual or the collected data) as not working, the process 700 loops back to process step 715 to permit the individual to reset the goal(s) previously recommended. If, however, a skill or understanding of the how to achieve the set goal(s) of the procedure 70 is indicated (either by the individual or the collected data) as lacking, the process 700 loops back to process step 720 to provide the education material and/or start the skill assessment module 724. If, however, the intervention of the procedure 70 is indicated (either by the individual or the collected data) as not working, the process 700 loops back to process step 725 such that the individual 12 can reassess their barriers and motivators in order to try to develop a better intervention plan/strategy.

If, however, in process step 745 the procedure 70 is working, then the process 700 continues with monitoring the procedure 70 in step 735. If, however, in process step 740, the goal has been achieved (i.e., exit criteria 228 is met), the process 700 permits the individual 12 to go back to set a new goal(s) that was previously recommended or continue progressing on the originally set goal(s) once again, or to go back to the to process step 705 for a new health and behavior assessment in order to develop a new personalized collection procedure 70 for attaining a new goal(s). Additionally, the process 700 permit the individual 12 to go to process step 720 to access the education information module 724, if desired.

Once the individual 12 has successfully gone through the personalized procedure 70 (i.e., exit criteria 228 has been met, wherein the individual 12 has achieved the short-term goal, the process 700 permits the individual 12 to continue to a next level of the BCP, i.e., short term goal S2. As the individual 12 progresses and the targeted behavior become part of the individual's daily life, in one embodiment the process 700 also permits the individual to choose and add different protocols to a master protocol 800 as depicted by FIG. 14.

As depicted, the master protocol 800 is a collection of the procedures 70 which the individual 12 can select upon progressing successfully through various short term, midterm, and/or long term goals. For example, if the individual successfully completes the short term goal for procedure $70_{A1}$, then the process 700 proceeds automatically to procedure $70_{A2}$ and also permits the individual to select procedure $70_{B1}$, which can be a mid-term goal e.g., adding another type of procedure, i.e. procedure $70_{B1}$, to perform simultaneous with the second level procedure $70_{A2}$. Continuing with this example, should the individual successfully complete procedure $70_{A2}$ and $70_{B1}$, then the process 700 proceeds automatically to procedure $70_{AX}$, $70_{B2}$, as well as permitting the individual to select new procedure $70_{X1}$, in which selecting one or both of the procedures $70_{B2}$, $70_{X1}$ e.g., can be a second mid-term goal, and so on. In this manner, the master protocol 800 provides the individual 12 with a customizable plan by which to progress through various levels and types of procedures 70 (e.g., automatically upon meeting the exit criteria of the previous level), such as those directed to exercise, e.g., procedures $70_{A1}$, $70_{A2}$, . . . , $70_{AX}$, diet e.g., procedures $70_{B1}$, $70_{B2}$, . . . , $70_{BX}$, and any other procedures e.g., $70_{X1}$, $70_{X2}$, . . . , $70_{XX}$, directed to reducing stress, improving sleep habits, and the likes providing for a behavior change. It is to be appreciated that with each new level and type of procedure 70, the individual personalizes the procedure 70 via being presented and performing process steps 705-730. An example of a structured tailoring use case is now discussed hereafter.

Structured Tailoring Use Case

An example of a structured tailoring use case would be a person wanting to begin an exercise program. The process 700 as mentioned above is used for short term, midterm and long term goals. In this use case example, the short term goal is defined as something that can be accomplished with in a few days or a week. For example, in this described exercise example, a starting short term goal could be to begin walking 1 day for 10 minutes the first week. The next week could be 2 days for 10 minutes, the second short term goal, the next could be two days for 15 minutes, the third short term goal, and so on. A series of such short term goals can then constitute a midterm goal. In another example, a first mid term goal could be that in the next 3 months I want to walk on average at least 2 times a week for 30 minutes. After that the first mid term goal, the next (second) midterm goal could be on average 4 times a week for 30 minutes, and so on. The long term goal then could be walking consistently 5 times a week for 30 minutes at a certain pace. Accordingly, it is to be appreciated that the short term goals are embedded in midterm goals which are embedded in long term goals.

Continuing with the use case example, the individual 12 will use the process 700 to personalize a first procedure 70 e.g., procedure $70_{A1}$, of the master protocol 800 via completing an initial assessment, setting an individual goal (say walk 30 minutes a day 3 days a week), identify barriers (too tired at the end of the day) and motivators (I like walking with my spouse), and set a plan for success (walk M-W-F in the morning with my wife). The individual 12 will then start the now personalized procedure 70, and when meeting the entry criteria (e.g., indicating physically ready and willing to carry out the plan), the process 700 begins monitoring progress of the procedure 70 in step 735 as described above.

In this example, if goal is met in step 740, the individual 12 is asked (e.g., by the processor 102 prompting on the display 108) "Do you want to continue this (procedure) or set a different exercise goal (walk 45 minutes 4 times a week), or do something else (work on eating healthier)?" If the goal is not met (e.g., the individual 12 walked only 2 times for 30 minutes), the process 700 in this example will ask the individual in step 745 (e.g., via the processor 102 prompting on the display 108) "Is the procedure working?" If the individual 12 indicates (e.g., via the user interface 146) that the process 700 is working (i.e., the individual 12 is on track, but hasn't reached the goal yet), the process 700 continues to monitor progress i.e., for each event 237 meeting the adherence criteria 224 (e.g., walk 30 minutes M-W-F w/spouse in the morning) in process step 735. If the result and/or the process are not working well (i.e. adherence criterion is not met, affecting exit criteria), then in this example, the process 700 checks whether the individual 12 is correctly utilizing the support intervention correctly (i.e. I wanted to walk with my spouse, but I never asked her).

If the process 700 determines that there truly is an adherence issue, it will stop the procedure 70, and send the individual 12 back to the appropriate area as mentioned previously above in previous section. For example, in response to answering the question "Are you ready for change?" provided by the process in process step 745 (or process step 634 (FIG. 9, checking for a deviation 635), in which the individual indicated that "Perhaps their health is preventing them from walking" from an answer selection menu presented by the process 700 (e.g., on display 108), the process 700 loops to process step 705 in an attempt to re-personalize a new procedure 70 which takes into account the current health of the individual. In another example, if the individual response to the question about wanting to change the goal to another recommended goal, e.g., 2 times a week for 10 minutes, the process 700 loops back to process step 715 to reset the goal. In still another example, if the individual indicated that the procedure 70 is not fully understood and/or that he or she is not sure of the skill level needed, the process 700 loops to the process step 720 such that the individual views educational information learning how to begin the subject exercise program, or to process step 725 to provide behavior support if the individual indicated that he or she needs a reminder to walk, or that their spouse doesn't want to walk (in which case they may want to walk with someone else).

As the individual 12 continues the BCP, the process 700 then allows for other levels and types of procedures to be initiated in the master protocol 800 which go either into more depth or breadth of exercise or into a new BCP area such as diet, diabetes management, sleep, stress management, etc., as previously discussed above in reference to FIG. 14. In this example, each of these additional procedures $70_{A1\ldots X}$, $70_{B1\ldots X}$, $70_{X1\ldots X}$, etc., can be run individually (linearly) or the individual 12 could have multiples ones of such procedures running in parallel, depending on the skill and motivation of the individual 12. Examples of typical questions and interventions for exercise (physical activity) which the process 700 can provide in process steps 705, 725 and along with an answer selection menu (such as provided on computer 18 and/or device 24) by which the individual and process personalizes the procedure 70, is provided hereafter.

In process step 705, some general considerations that the individual 12 selects are: I prefer to do one type of exercise program for a long period of time; I enjoy changing my exercise routine frequently; I am more successful changing one intervention at a time; and I am more successful when I change multiple behaviors at the same time. The process 700 uses the selected consideration(s) to provide recommendations in step 710. In process step 725, the process 700 can present in one embodiment, the following question "What are things that typically stopped/prevented or discouraged you in the past or you could imagine may stop you in the future from participating in physical activity?" The individual 12 can then select from a presented answer list that explorers the individual 12 road blocks to achieving change.

In one example, a set of questions each with an answer list which the individual 12 can select from, explorer the internal road blocks and type of tailored intervention desired. Such questions and answer lists are as follows:

a. "When I experienced negative emotions, e.g. sad, afraid or angry"—
  I would like to meet or to connect with people to support me in dealing with my negative emotions
    I will connect to My Social Network (that is created on the same web-site) to designated "supporters" for the list (Action)
      Intervention: message will be sent to the "supporter" as a text message "Bob is staring an exercise program, are you willing to support him?" and then offer to schedule times to talk and call and schedule and appt in the supporter's calendar to call Bob at a certain time, with a reminder
    I will call my friend _____ (name)
      Intervention: type in the name of the person and make the call
  I would like to receive more information and techniques on how to change my negative thinking
    Intervention: connect to the CBT training/intervention site, built in the web-site or a separate site
  I would like to receive encouraging messages
    Intervention: automated text messages to
      cell phone
      voice mail
      email
      pedometer
b. "When I felt tired or sluggish"—
  I would like to receive information/tips on increasing my energy.>connect to helpful hints (check your sleep, eating consistently throughout the day, caffeine intake, sick/illness, exercise, stress, time management)
c. "When I don't think I am benefiting"—
  I would like to receive information on the benefits of exercise for people like me
    Intervention: tailored research messages sent based on profile (age, weight, fitness level, etc)
    Intervention: receive stories showing good outcomes from people like me (based on profile)
  I would like to be reminded by emails/messages about the benefits of exercise
    Intervention: automated affirmation text messages based on initial outcome expectations to
      cell phone
      voice mail
      email
      pedometer
d. "When I am not enjoying the activity"—
  I would like to receive support to increase enjoyment in exercise
    Intervention: list of alternate physical activities based on goal settings (time, frequency, calories burned)
    Intervention: chose a buddy to call (select or type in) to exercise with you
    Intervention: use or change music, redirect to the Company™ website to download motivating, stimulating music (recommended titles: Show me the money, Caress my motivation etc)
    Intervention: Change time and frequency of exercise
    Intervention: Competition: connect to Exercise Buddy Network site and set up/sign up competitions
    Intervention: exercise in the bright colored Company™ spandex
    Intervention: combine old and new activities: watch The Biggest Loser or read magazines while exercising (on stationary bike)
    Intervention: DVD game boy, Wii to vary exercise routine
    Intervention: exercise in a nicer place (project images of beautiful scenarios, exercise in virtual reality headgear and suit)
e. "When I don't plan and prioritize my activities well"—
  I would like to receive info on time management and prioritization
f. "When I experience physical activity as boring or uninteresting"—
  Mindfulness and acceptance education (boring is not necessary bad, no need to feel good constantly)

In another example, a set of questions each with an answer list which the individual 12 can select from, explorer the social road blocks and type of tailored intervention desired. Such questions and answer lists are as follows:

a. When I don't have someone to encourage me to exercise
  Intervention: I would like to receive encouraging messages from Company X
    voice mail
    cell phone
    email
    pedometer
  Intervention: I will ask _____ (name) to take me to exercise (matching names from Contact list will automatically pop up to select the appropriate contact)
  Intervention: I would like to encourage messages from _____ (name) from My Social Network, that will trigger messages from the person (as above)
  Intervention: video clips from virtual friends
  Intervention: grandkids recording encouraged messages that are played for encouragement
  Intervention: virtual puppy whines until one gets up for a walk
b. When I don't have someone to exercise with me
  Intervention: connect to My Social Network
c. When my friends and family discourage me by words and example
  Intervention: connect to My Social Network In another example, a set of questions each with an answer list which the individual 12 can select from, explorer the environmental road blocks and type of tailored intervention desired. Such questions and answer lists are as follows:

a. When I don't have anywhere pleasant to exercise
  I would like to receive information on women-only gyms (Curves in the area)
    Intervention: receive a list of gyms and park within walking distance from my house (based on ZIP code)
    Intervention: suggestions where to exercise in inclement weather (connect with mall walkers in the area
    Intervention: Connect with outers who exercise outdoors improve safety/reduce crime. Connect with Neighborhood Watch and monitor crime activity while exercising, while improving safety in neighborhood
    Intervention: exercise group at the church or community center (search by ZIP code for locations)—also ties in with community/social
b. When I don't have the equipment to exercise
  Low budget solutions (mall walkers with canned groceries, church
c. When I don't have transportation to get to exercise (addressed under social, "take me to the park")

In another example, a similar set of questions each with an answer list which the individual 12 can select from, can be provided which explorers the things that typically supported, enabled or encouraged the individual to exercise in the past or which could be possibly helpful in the future in which to help the individual decide on the type of tailored intervention desired. Such questions could be as follows:

Internal:
a. When I feel strong and confident
b. When I have a clear plan or routine
c. When I believe I can do it
d. When it makes me feel good
e. When I am playing game
f. When I feel I am benefiting
g. When I reward myself for exercising
h. When I think about how this will benefit my friends and family Social:
a. When others encourage me to exercise and compliment me on my improvements
b. When someone rewards me for my accomplishments
c. When I see or hear about other people like me who benefited from exercise
d. When I have a buddy to exercise with me
e. When I exercise alone with some instructions
f. When I am competing with other people or with a goal
g. When I have someone to take me to exercise Environmental
a. When I can exercise on my own terms
b. When I can find safe neighborhoods
c. When I put reminders in my home or work environment
d. When I change my environment to encourage physical activity, such as use public transportation, park farther away from the building or take the stairs
e. When I know that what I am doing is helping the environment or I become an advocate for social change Accordingly, by the above structured tailoring disclosure, in one embodiment, a system implementing the process 700 can help to enhance the success of behavior change of a individual 12 by helping the individual 12 to personalize a collection procedure as well as running and monitoring the personalized collection procedure(s) 70. The system can be computerized, such as implemented on device 24, personal computer 18, and/or web based such as hosted by a server 52 which is accessible by the device 24 and/or personal computer 18 as well as clinician computer 25 via a standard web browser and network 50 (FIG. 1).

Although not limited thereto, some of the noted advantages provided by such a structured tailoring based system are: an increase in the personal relevance of health messages, which consequently assist in creating an ideal environment in which persuasion and behavior change can occur; and enhancing the creation of the tailored messages by facilitating the collection and assessment of individual data and then using evidence-based decision rules to create individualized health messages, strategies and action plans.

Thus, by the above disclosure embodiments concerning systems and methods managing the execution, data collection, and data analysis of collection procedures running simultaneously on an electronic device are disclosed for the purposes of helping the individual change a current behavior to a target behavior, and/or assisting the individual in addressing/changing a health related behavior. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A method of performing a self-administered, behavior modification program on a blood glucose meter which comprises facilitating a structured collection procedure for an individual which helps the individual change a current behavior to a target behavior and improves compliancy with the structured collection procedure, said method comprising:
   providing the blood glucose meter loaded with the structured collection procedure and program instructions;
   downloading the structured collection procedure from a server onto a client device, wherein software on the client computer serves as an interface between the server and the meter, wherein the server can only access information related to the installed version of the software and the server cannot access data in a database residing on the client device, wherein subsequent downloads of the particular structured collection procedure onto the client require access from an authorized client user;
   measuring a biomarker comprising a blood glucose level with the blood glucose meter according to the structured collection procedure; and
   executing the program instructions on the blood glucose meter causing a processor of the blood glucose meter to:
      personalize the structured collection procedure by requesting goals from the individual to define for events to be accomplished in the structured collection procedure one or more adherence criteria that the processor uses to determine automatically whether each event was accomplished successfully and to define one or more exit criteria for ending the structured collection procedure, and requesting intervention preferences from the individual;
      initiate automatically a schedule of the events defined in the structured collection procedure upon one or more entry criteria being met;
      provide intervention automatically according to the intervention preferences when the one or more adherence criteria for one of the events is not met;
      end automatically the structured collection procedure upon the one or more exit criteria being met, wherein the processor continues automatically with the next one of the events in the structured collection procedure until the one or more exit criteria is met; and
      assign a unique identifier to the events, when the one or more adherence criteria are met, which corresponds to the events in the structured collection procedure; and wherein the unique identifier is not assigned when the biomarker measurement is determined by the processor as not being close enough in time to a data event request based on a prescheduled time so as to facilitate the structured collection procedure and improve the compliancy with the structured collection procedure of a management system; and
      providing a microprocessor, a memory, a power source, and an indicator, the indicator connected to the processor and which can operate under the control of the processor to emit audible, tactile, or visual alerts to the individual of daily times for the biomarker measurement; and sending a message from the blood glucose meter to a physician when the individual fails to complete one of the one or more adherence criteria, wherein a communication link between a computer of the physician and the blood glucose meter can be established upon connection via the server.

2. The method according to claim 1 wherein the program instructions further cause the processor to perform an initial assessment of the individual to tailor both the events as well as the interventions provided by the structured collection procedure.

3. The method of claim 2, wherein the initial assessment is based on answers to catalog questions provided to the individual.

4. The method according to claim 2 wherein the initial assessment cover areas of readiness for change, current health, and activity level of the individual.

5. The method according to claim 2 wherein the program instructions further cause the processor to provide a recommendation based on the input received from the individual concerning the initial assessment.

6. The method according to claim 5 wherein the program instructions further cause the processor to use the recommendation as the one or more entry criteria.

7. The method according to claim 5 wherein the program instructions further cause the processor permit the individual to tailor the recommendation to his or her individual abilities and availability.

8. The method according to claim 1 wherein the program instructions further cause the processor to permit the individual to define the goals as short term goals, midterm goals, and a long-term goal.

9. The method according to claim 8 wherein the program instructions further cause the processor to automatically cycle through each of the goals defined by the individual upon successful completion of a previous goal.

10. The method according to claim 2 wherein the program instructions further cause the processor to provide a recommendation based on the input received from the individual concerning the initial assessment, and to define one of the goals as a short-term goal that is based on the results from the assessment and the recommendation.

11. The method according to claim 1 wherein the program instructions further cause the processor to provide upon request an education module which provides education material.

12. The method according to claim 11 wherein the education material contains health and behavior education in relation to the targeted behavior.

13. The method according to claim 11 wherein the education material include a skill assessment and skill development activities.

14. The method according to claim 1 wherein the program instructions further cause the processor to assess if the individual possesses the proper level of skill before moving into a new structured collection procedure.

15. The method according to claim 14 wherein the program instructions further cause the processor to provide skill development activities for the individual to complete in order to gain the skill for the new structured collection procedure if assess by the processor as not have the proper level of skill.

16. The method according to claim 1 wherein the program instructions further cause the processor to provide a behavior support assessment to ascertain from the individual what barriers and motivators in the past have assisted in success or failures when it comes to performing the target behavior.

17. The method according to claim 16 wherein the program instructions further cause the processor to provide a behavior-support intervention module in which the individual picks one or more pre-defined interventions based on the barriers and motivators ascertained from the individual.

18. The method according to claim 17 wherein the pre-defined interventions are selected from electronic alarms, reminders, messages, and prompting social support networks for help.

19. The method according to claim 17 wherein the program instructions further cause the processor to provide a validation module which ascertains whether an appropriate level of intervention is assigned due to an associated risk if one of the events fail to meet the one or more adherence criteria.

20. The method according to claim 1 wherein the schedule of events define how often progress will be monitored by the procedure.

21. The method according to claim 20 wherein the program instructions further cause the processor to monitor compliancy of the individual with the events by assessing whether the one or more adherence criteria have been met by the individual when performing each one of the events.

22. The method according to claim 1 wherein the program instructions further cause the processor to check whether there is an indication that the structured collection procedure is not working if the one or more exit criteria are not met.

23. The method according to claim 22 wherein the indication is provided to the processor by the individual or is shown in collected data associated with each one of the events.

24. The method according to claim 23 wherein where the indication is present, then the program instructions further cause the processor to query the individual as to whether the individual believes the procedure is working, whether the individual is following the intervention, or whether the individual is lacking in a skill or understanding of how attain the goals.

25. The method according to claim 24 wherein the program instruction further cause the processor to perform a health and behavior support assessment in order to work through the process of providing a new personalized collection procedure if the collection procedure is indicated as not working, to request again the intervention preferences from the individual if the individual indicates that the intervention is not being followed, and to provide education material or start a skill assessment module if the individual indicates a lack in skill or understanding.

26. A method for performing a self-administered, behavior modification program of a management system on a blood glucose meter which comprises facilitating a structured collection procedure for an individual which helps the individual change a current behavior to a target behavior, said method comprising:
    providing the blood glucose meter loaded with the structured collection procedure and program instructions, the blood glucose meter comprising;
        a memory which stores the structured collection procedure; and
        a processor connected to the memory; and
    measuring a biomarker comprising a blood glucose level with the blood glucose meter and digitally storing the biomarker value in the memory of the blood glucose meter according to the structured collection procedure;
    executing the program instructions on the blood glucose meter causing the processor of the blood glucose meter to:
        personalize the structured collection procedure by requesting goals from the individual to define for events to be accomplished in the structured collection procedure one or more adherence criteria that the processor uses to determine automatically whether each event was accomplished successfully and to define one or more exit criteria for ending the structured collection procedure, and requesting intervention preferences from the individual;

initiate automatically a schedule of the events defined in the structured collection procedure upon one or more entry criteria being met;

store in the memory data collected in accordance to the schedule;

provide intervention automatically according to the intervention preferences when the one or more adherence criteria for one of the events is not met;

end automatically the structured collection procedure upon the one or more exit criteria being met, wherein the processor continues automatically with the next one of the events in the structured collection procedure until the one or more exit criteria is met;

assign a unique identifier to the events, when the one or more adherence criteria are met, which corresponds to the events in the structured collection procedure; and wherein the unique identifier is not assigned when the biomarker measurement is determined by the processor as not being close enough in time to a data event request based on a prescheduled time so as to facilitate the structured collection procedure and improve the compliancy with the structured collection procedure of the management system; and providing a microprocessor, a power source, and an indicator, the indicator connected to the processor and which can operate under the control of the processor to emit audible, tactile, or visual alerts to the individual of daily times for the biomarker measurement; and sending a message from the blood glucose meter to a physician when the individual fails to complete one of the one or more adherence criteria, wherein a communication link between a computer of the physician and the blood glucose meter can be established upon connection via a web server.

27. A method for performing a self-administered, behavior modification program on a blood glucose meter which comprises facilitating a structured collection procedure for an individual which helps the individual change a current behavior to a target behavior and improves compliancy with the structured collection procedure, the method comprising:

providing the blood glucose meter loaded with a master protocol comprising sub-protocols of various structured collection procedures and program instructions, each of the various structured collection procedures address a goal that addresses the target behavior and comprises entry criteria and exit criteria, wherein entry criteria of some of the various structured collection procedures is met upon exit criteria of previous ones of the various structured collection procedures being met; and measuring a biomarker comprising a blood glucose level with the blood glucose meter and digitally storing the biomarker value in a memory of the blood glucose meter according to the structured collection procedure; and executing the program instructions on the blood glucose meter causing a processor of the blood glucose meter to:

personalize the structured collection procedure by requesting goals from the individual to define for entry criteria to be accomplished in the structured collection procedure, one or more adherence criteria that the processor uses to determine automatically whether each event was accomplished successfully and to define an exit criterion for ending the structured collection procedure, and requesting intervention preferences from the individual;

use the entry criteria based on invention preferences from the individual of each of the various structured collection procedures to determine automatically which of the various structured collection procedures are first enabled in the master protocol, run the master protocol with first enabled ones of the various structured collection procedures, end each of the first enabled ones of the various structured collection procedures when the exit criteria of each of the first enabled ones of the various structured collection procedures have been met, run automatically the master protocol with next ones of the various structured collection procedure having their entry criteria met by the exit criteria of the previous ones of the various structured collection procedures being met; and assign a unique identifier to the each event, when the one or more adherence criteria are met, which corresponds to the each event in the structured collection procedure; and wherein the unique identifier is not assigned when the biomarker measurement is determined by the processor as not being close enough in time to a data event request based on a prescheduled time so as to facilitate the structured collection procedure and improve the compliancy with the structured collection procedure of a management system; and providing a microprocessor, a power source, and an indicator, the indicator connected to the processor and which can operate under the control of the processor to emit audible, tactile, or visual alerts to the individual of daily times for the biomarker measurement; and sending a message from the blood glucose meter to a physician when the individual fails to complete one of the one or more adherence criteria, wherein a communication link between a computer of the physician and the blood glucose meter can be established upon connection via a web server.

28. The method according to claim 21 wherein the program instructions further cause the processor to stop the structured collection procedure if the one or more adherence criteria are not met and instructs the individual to contact a clinician.

29. The method of claim 1 further comprising executing the program instructions on the device causing the processor of the device to de-tag data records by nullifying the unique identifiers in a data file for data collected for a cancelled structured collection procedure.

30. The method of claim 1 wherein the data event request is designated as critical or non-critical, and time for the biomarker measurements for the critical request is extendible by the individual for pre-defined periods within the prescheduled time, and the time for the biomarker measurements for the non-critical request is extendible beyond the prescheduled time.

* * * * *